United States Patent
Yeh

(10) Patent No.: US 7,179,650 B1
(45) Date of Patent: Feb. 20, 2007

(54) COMPOSITIONS AND USES FOR A NOVEL CELL-DEATH-PROTECTING PROTEIN

(75) Inventor: Edward T. H. Yeh, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 09/484,964

(22) Filed: Jan. 18, 2000

Related U.S. Application Data

(62) Division of application No. 08/964,162, filed on Nov. 4, 1997, now abandoned.

(60) Provisional application No. 60/030,302, filed on Nov. 5, 1996.

(51) Int. Cl.
*C12N 15/63* (2006.01)
*C12N 15/74* (2006.01)
*C12N 5/00* (2006.01)

(52) U.S. Cl. .................... 435/455; 435/325; 435/320.1

(58) Field of Classification Search ............. 435/320.1, 435/325, 455; 514/44
See application file for complete search history.

(56) References Cited

U.S. PATENT DOCUMENTS

| | | | |
|---|---|---|---|
| 4,196,265 A | 4/1980 | Koprowski et al. ............. | 435/2 |
| 4,554,101 A | 11/1985 | Hopp ...................... | 260/112.5 |
| 4,683,195 A | 7/1987 | Mullis et al. .................. | 435/6 |
| 4,683,202 A | 7/1987 | Mullis ......................... | 435/91 |
| 4,757,011 A | 7/1988 | Chaleff et al. ............ | 435/172.1 |
| 4,769,061 A | 9/1988 | Comai ........................... | 71/86 |
| 4,940,835 A | 7/1990 | Shah et al. .................. | 800/205 |
| 4,965,188 A | 10/1990 | Mullis et al. ................... | 435/6 |
| 4,971,908 A | 11/1990 | Kishore et al. ........... | 435/172.1 |
| 5,176,995 A | 1/1993 | Sninsky et al. ................. | 435/6 |
| 5,384,253 A | 1/1995 | Krzyzek et al. .......... | 435/172.3 |

FOREIGN PATENT DOCUMENTS

WO    WO 95/31544    11/1995

OTHER PUBLICATIONS

Orkin et. al.; Report and Recommendations of the Panel to Assess the NIH Investment in Research on Gene Therapy, 1995.*
Lieberthal et. al.; Mechanisms of apoptosis and its potential role in renal tubular epithelial cell injury, 1996, Invited Review : F477-F488.*
Lavin et. al.; Role of protein kinase activity in apoptosis, 1996, Experiential 52:979-994.*
Marshall; Gene Therapy's Growing Pains, 1995, Science, vol. 269: 1050-1055.*
Verma et. al.; Gene therapy- promises, problems and prospects, 1997, Nature vol. 389: 239-242.*
Boddy et al., "PIC 1, a novel ubiquitin-like protein which interacts with the PML component of a multiprotein complex that is disrupted in acute promyelocytic leukemia", Oncogene, 13:971-982, 1996.

Cenciaelli et al., "T cell antigen receptor ubiquitination is a consequence of receptor-mediated tyrosine kinase activation," *J. Biol. Chem.*, 271(15):8709-8713, 1996.
Chinnaiyan et al., "FADD, a novel death domain-containing protein, interacts with the death domain of Fas and initiates apoptosis," *Cell*, 81:505-512, 1995.
Chinnaiyan et al., "FADD/MORT1 is a common mediator of CD95 (Fas/APO-1) and tumor necrosis factor receptor-induced apoptosis," *J. Biol. Chem.*, 271(9):4961-4965, 1996.
Chu et al., "A Fas-associated protein factor, FAF1, potentiates Fas-mediated apoptosis," *Proc. Natl. Acad. Sci. USA*, 92:11894-11898, 1995.
Coux et al., "Structure and functions fo the 20S and 26S proteasomes," *Annu. Rev. Biochem.*, 65:801-847, 1996.
Darnay et al., "Identification of a protein kinase associated with cytoplasmic domain of the p60 tumor necrosis factor receptor," *J. Biol. Chem.*, 269(32):20299-20304, 1994.
Finley et al., "Inhibition of proteolysis and cell cycle progression in a multiubiquitination-deficient yeast mutant," *Mol. Cell. Biol.*, 14(8):5501-5509, 1994.
Görlich et al., "Nucleocytoplasmic transport," *Science*, 271:1513-1518, 1996.
Göttlicher et al., "Interaction of the Ubc9 human homologue with c-Jun and with the glucocorticoid receptor," *Steroids*, 61:257-262, 1996.
Hateboer et al., "mUBC9, a novel adenovirus E1A-interacting protein that complements a yeast cell cycle defect," *J. Biol. Chem.*, 271(42):25906-25911, 1996.
Hsu et al., "TRADD-TRAF2 and TRADD-FADD interactions define two distinct TNF receptor 1 signal transduction pathways," *Cell*, 84:299-308, 1996a.
Hsu et al. "TNF-dependent recruitment of the protein kinase RIP to the TNF receptor-1," *Immunity*, 4:387-396, 1996b.
Kamitani et al., "Characterization of NEED8, a developmentally down-regulated ubiquitin," *J. Biol. Chem.*, 272(45):28557-28562, 1997b.
Kamitani et al., "Preferenctial modification of nuclear proteins by a novel ubiquitin-like molecule," *J. Biol. Chem.*, 272(22):14001-14004, 1997.
Kho et al., "Degradation of E2A proteins through a ubiquitin-conjugating enzyme, UbcE2A," *J. Biol. Chem.*, 272(6):3845-3851, 1997.
Kischkel et al., "Cytotoxicity-dependent APO-1 (Fas/CD95)-associated proteins form a death-inducing signaling complex (DISC) with the receptor," *EMBO J.*, 14(22):5579-5588, 1995.
Mannen et al., "Cloning and expression of human homolog HSMT3 to yeast SMT3 suppressor of MIF2 mutations in a centromere protein gene," *Biochem. Biophy. Res. Comm.*, 222:178-180, 1996.

(Continued)

*Primary Examiner*—Anne M. Wehbe'
(74) *Attorney, Agent, or Firm*—Fulbright & Jaworski LLP

(57) ABSTRACT

Disclosed are compositions comprising a novel cell-death protecting protein, sentrin-1, and the gene which encodes it. Also disclosed are methods of making and using sentrin polypeptides and nucleic acid segments in various diagnostic and pharmaceutical applications. In a preferred embodiment, overexpression of sentrin-1 confers protection against both anti-Fas/APO-1 and TNF-induced apoptosis.

6 Claims, 21 Drawing Sheets

OTHER PUBLICATIONS

Figure 1B:
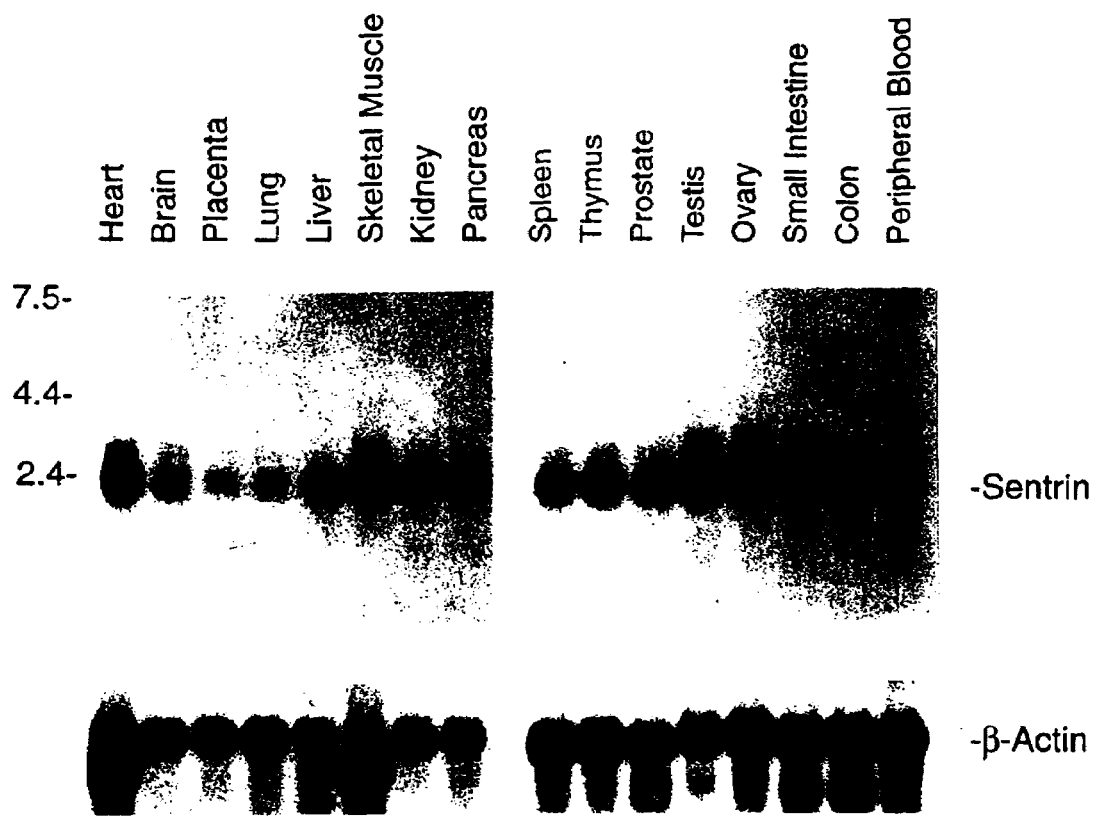

Muzio et al., "FLICE, novel FADD-homologous ICE/CED-3-like protease, is recruited to the CD95 (Fas/APO-1) death-inducing signaling complex," *Cell*, 85:817-827, 1996.

Nuber et al., "Cloning of human ubiquitin-conjugating enzymes UbcH6 and UbcH7 (E2-F1) and characterization of their interaction with E6-AP and RSP5," *J. Biol. Chem.*, 271(5):2795-2800, 1996.

Saitoh et al., "RanBP2 associates with Ubc9p and a modified form of RanGAP1," *Proc. Natl. Acad. Sci. USA.*, 94:3736-3741, 1997.

Stanger et al., "RIP: a novel protein containing a death domain that interacts with Fas/APO-1 (CD95) in yeast and causes cell death," *Cell*, 81:513-523, 1995.

Takayama et al., "Cloning and functional analysis of BAG-1: a novel Bcl-2-binding protein with anti-cell death activity," *Cell*, 80:279-284, 1995.

Wang et al., "Molecular cloning of a cNDA and chromosome localization of the gene for human ubiquitin-conjugating enzyme 9," *J. Biol. Chem.*, 271(40):24811-24816, 1996.

Ayala et al., "Mendelain Genetics," In: *Modern Genetics*, 2nd Edition, Menlo Park, California, Benjamin/Cummings Publishing Co., Inc., Chapter 2, p. 44, 1984.

Darnell et al., In: *Molecular Cell Biology*, Scientific American Books, New York, pp. 77-80 and 248-257, 1986.

Database GenBank on STN. US National Library of Medicine (Bethesda, MD, USA). GenBank Accession No. H98111, Hellier et al., "The WashU-Merck EST Project," yx09d11.sl *Homo sapiens* cDNA clone 261237 3'. Dec. 12, 1995.

Database GenBank on STN. US National Library of Medicine (Bethesda, MD, USA). GenBank Accession No. H24103, Hellier et al., "The WashU-Merck EST Project," ym50b07.rl *Homo sapiens* cDNA clone 51818 5'. Jul. 6, 1995.

International Search Report dated Mar. 11, 1998 (PCT/US97/20344)(UTFH:238P).

Shen et al., "UBL1, a human ubiquitin-like protein associating with human RAD51/RAD52 proteins," *Genomics*, 36(2):271-279, 1996.

Matunis et al., "A novel ubiquitin-like modification modulates the partitioning of the ran-GTpase-activating protein Ran GAP1 between the Cytosol and the nuclear pore complex," *J. Cell Biol.*, 135(6):1457-1470, 1996.

Okura et al., "Protection against Fas/APO-1 and tumor necrosis factor-mediated cell death by a novel protein, Sentrin," *J. Immunol.*, 157(10):4277-4281, 1996.

Shen et al., "Associations of UBE21 with RAD52, UBL1, p. 53, and RAD51 proteins in a yeast two-hybrid systems," *Genomics*, 37:183-186, 1996.

\* cited by examiner

| Binding Domain Hybrid | | Activation Domain Hybrid |
|---|---|---|
| Fas | | Sentrin |
|  | wt (191–319AA) | ++ |
| 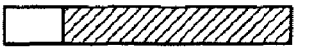 | Δ 15 (191–304AA) | ++ |
|  | Δ 23 (191–296AA) | – |
|  | (V238N) | – |
| TNFR1 | | |
|  | wt (326–426AA) | ++ |
|  | Δ 14 (326–412AA) | ++ |
| 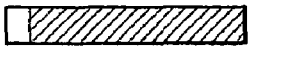 | Δ 20 (326–406AA) | – |
| CD40 | | |
|  | (216–277AA) | – |
| FADD/MORT1 | | |
| 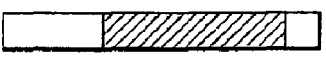 | (1–208AA) | – |
| Activation Domain Hybrid | | Binding Domain Hybrid |
|---|---|---|
| | | Fas (191–319AA) |
| Sentrin  | (1–101AA) | ++ |
|  | (1–70AA) | – |
|  | (1–23AA) | – |
|  | (24–97AA) | – |
| Ubiquitin  | (1–76AA) | – |
| Nedd8  | (1–76AA) | – |
FIG. 1A CGAGGCGTAGCGGAAGTTACTGCAGCCGCGGTGTTGTGCTGT
CGGGAAGGGGAAGGATTTGTAAACCCCGGAGCGAGGTTCTGC
TTACCCGAGGCCGCTGCTGTGCGGAGACCCCGGGTGAAGCC
ACCGTCATCATGTCTGACCAGGAGGCAAAACCTTCAACTGAG
   M S D Q E A K P S T E
GACTTGGGGGATAAGAAGCAAGGTGAATATATTAAACTCAAA
D L G D K K E G E Y I K L K
GTCATTGGACAGGATAGCAGTGAGATTCACTTCAAAGTGAAA
V I G Q D S S E I H F K V K
ATGACAACACATCTCAAGAAACTCAAAGAATCATACTGTCAA
M T T H L K K L K E S Y C Q
AGACAGGGTGTTCCAATGAATTCACTCAGGTTTCTCTTTGAG
R Q G V P M N S L R F L F E
GGTCAGAGAATTGCTGATAATCATACTCCAAAAGAACTGGGA
G Q R I A D N H T P L E L G
ATGGAGGAAGAAGATGTGATTGAAGTTTATCAGGAACAAACG
M E E E D V I E V Y Q E Q T
GGGGGTCATTCAACAGTTTAGATATTCTTTTATTTTTTTC
G G H S T V *101
TTTTCCCTCAATCCTTTTTTATTTTTAAAAATAGTTCTTTTC
TAATGTGGTGTTCAAAACGGAATTGAAAACTGGCACCCCATC
TCTTTGAAACATCTGGTAATTTGAATTCTAGTGCTCATTATT
CATTATTGTTTGTTTTCATTGTGCTGATTTTTGGTGATCAAG
CCTCAGTCCCCTTCATATTACCCTCTCCTTTTTAAAAATTAC
GTGTGCACAGAGAGGTCACCTTTTTCAGGACATTGCATTTTC
AGGCTTGTGGTGATAAATAAGATCGACCAATGCAAGTGTTCA
TAATGACTTTCCAATTGGCCCTGATGTTCTAGCATGTGATTA
CTTCACTCCTGGACTGTGACTTTCAGTGGGAGATGGAAGTTT
TTCAGAGAACTGAACTGTGGAAAAATGACCTTTCCTTAACTT
GAAGCTACTTTTAAAATTGAGAGTAATGACTAACTCCAAAGA
TGGCTTCACTGAAGAAAGGCATTTTAAGATTTTTTAAAAAT
CTTGTCAGAAGATCCCAGAAAAGTTCTAATTTTCATTAGCAA

FIG. 2A-1

```
TTAATAAAGCTATACATGCAGAAATGAATACAACAGAACACT
GCTCTTTTTGATTTTATTTGTACTTTTTGGCCTGGGATATGG
GTTTTAAATGGACATTGTCTGTACCAGCTTCATTAAAATAAA
CAATATTTGTCAAAATCGTACTAATGCTTATTTTATTTTAA
TTGTATAGAAGAAAAAAATGCCTAAAATAAGGTTTTCTTGC
ATAAATACTGGAATTGCACATGGTACAAAAAAAAATGCCT
AAATTACTGTACAGGGATGATGTTAATGACTTTGGAGCACTG
AAAGTTACTGAAGTGCCTTCTGAATCAAGGATTTAATTAAGG
CCACAATACCTTTTAATACTCAGTGTTCTGTTTTTTTTAAA
AACTTGATATTCCCGTATGGTGCATATTGATACAGGTACCC
AATCATGTTGGATAAATGGGCATGCCAGCC
```

FIG. 2A-2

```
            1                                              40
Sentrin    MSD     QEAKPST  EDLGDKKEGE  YIKLKVIGQD  SSEIHFKVKM
SMT3       MSDSEVNQEAKPEV   KP-EVKPETH  -INLKV-SDG  SSEIFFKIKK
Ubiquitin                               MQIFVKTLT   GKTITLEVEP
Nedd-8                                  MLIKVKTLT   GKEIEIDIEP 41                                             60
Sentrin    TTHLKKLKES  YCQRQGVPMN
SMT3       TTPLRRLMEA  FAKRQGKEMD
Ubiquitin  SDTIENVKAK  IQDKEGIPPD
Nedd-8     TDKVERIKER  VEEKEGIPPQ
BAG-1      ---VQDLAQL  VEEATGVPLP 61                                             80
Sentrin    SLRFLFEGQR  IADNHTPKEL
SMT3       SLRFLYDGIT  IQADQTPEDL
Ubiquitin  QQRLIFAGKQ  LEDGRTLSDY
Nedd-8     QQRLIYSGKQ  MNDEKTAADY
BAG-1      FQKLIFKGKS  LKE-------

81                                            100
Sentrin    GMEEEDVIEV  YQEQTGGHST V
SMT3       DMEDNDIIEA  HREQIGGATY
Ubiquitin  NIQKESTLHL  VLRLRGG
Nedd-8     KILGGSVLHL  VLALRGG
```

FIG. 2B

| | | | |
|---|---|---|---|
| Sentrin-1(1-30) | MSDQEAKPST | EDLGDKKEGE | -YIKLKVIGQD |
| Sentrin-2(1-26) | MAD-E-KPK- | E--GVKTENN | DHINLKVAGQD |
| Sentrin-3(1-25) | MSE-E-KPK- | E--GVKTEN- | DHINLKVAGQD |
| NEDD8(1-9) | | | MLIKVKTLT |
| Ubiquitin(1-9) | | | MQIFVKTLT |
| | | | |
| Sentrin-1(31-60) | SSEIHFKVKM | TTHLKKLKES | YCQRQGVPMN |
| Sentrin-2(27-56) | GSVVQFKIKR | HTPLSKLMKA | YCERQGLSMR |
| Sentrin-3(26-55) | GSVVQFKIKR | HTSLSKLMKA | YCERQGLSMR |
| NEDD8(10-39) | GKEIEIDIEP | TDKVERIKER | VEEKEGIPPQ |
| Ubiquitin(10-39) | GKTITLEVEP | SDTIENVKAK | IQDKEGIPPD |
| | | | |
| Sentrin-1(61-90) | SLRFLFEGQR | IADNHTPKEL | GMEEEDVIEV |
| Sentrin-2(57-86) | QIRFRFDGQP | INETDTPAQL | EMEDEDTIDV |
| Sentrin-3(56-85) | QIRFRFDGQP | INETDTPAQL | RMEDEDTIDV |
| NEDD8(40-69) | QQRLIYSGKQ | MNDEKTAADY | KILGGSVLHL |
| Ubiquitin(40-69) | QQRLIFAGKQ | LEDGRTLSDY | NIQKESTLHL |
| | | | |
| Sentrin-1(91-101) | YQEQTGGHSTV | | |
| Sentrin-2(87-95) | FQQQTGGVY | | |
| Sentrin-3(86-103) | FQQQTGGVPESSLAGHSF | | |
| NEDD8(70-81) | VLALRGGGGLR | | |
| Ubiquitin(70-76) | VLRLRGG | | |

FIG. 12

SEQUENCE LISTING

```
<160> NUMBER OF SEQ ID NOS: 18

<210> SEQ ID NO 1
<211> LENGTH: 1465
<212> TYPE: DNA
<213> ORGANISM: Homo sapiens
<220> FEATURE:
<221> NAME/KEY: CDS
<222> LOCATION: (88)..(390)

<400> SEQUENCE: 1
cgggaaggat ttgtaaaccc cggagcgagg ttctgcttac ccgaggccgc tgctgtgcgg      60
agacccccgg gtgaagccac cgtcatc atg tct gac cag gag gca aaa cct tca    114
                                Met Ser Asp Gln Glu Ala Lys Pro Ser
                                  1               5 act gag gac ttg ggg gat aag aag caa ggt gaa tat att aaa ctc aaa      162
Thr Glu Asp Leu Gly Asp Lys Lys Gln Gly Glu Tyr Ile Lys Leu Lys
 10              15                  20                  25
```

```
gtc att gga cag gat agc agt gag att cac ttc aaa gtg aaa atg aca         210
Val Ile Gly Gln Asp Ser Ser Glu Ile His Phe Lys Val Lys Met Thr
         30                  35                  40 aca cat ctc aag aaa ctc aaa gaa tca tac tgt caa aga cag ggt gtt         258
Thr His Leu Lys Lys Leu Lys Glu Ser Tyr Cys Gln Arg Gln Gly Val
     45                  50                  55 cca atg aat tca ctc agg ttt ctc ttt gag ggt cag aga att gct gat         306
Pro Met Asn Ser Leu Arg Phe Leu Phe Glu Gly Gln Arg Ile Ala Asp
 60                  65                  70 aat cat act cca aaa gaa ctg gga atg gag gaa gaa gat gtg att gaa         354
Asn His Thr Pro Lys Glu Leu Gly Met Glu Glu Glu Asp Val Ile Glu
 75                  80                  85 gtt tat cag gaa caa acg ggg ggt cat tca aca gtt tagatattct              400
Val Tyr Gln Glu Gln Thr Gly Gly His Ser Thr Val
 90                  95                 100 ttttatttttt tttcttttcc ctcaatcctt ttttatttt aaaaatagtt cttttgtaat       460
gtggtgttca aaacggaatt gaaaactggc accccatctc tttgaaacat ctggtaattt       520
gaattctagt gctcattatt cattattgtt tgttttcatt gtgctgattt ttggtgatca       580
agcctcagtc cccttcatat taccctctcc tttttaaaaa ttacgtgtgc acagagaggt       640
cacctttttc aggacattgc attttcaggc ttgtggtgat aaataagatc gaccaatgca       700
agtgttcata atgactttcc aattggccct gatgttcagc atgtgattac ttcactcctg       760
gactgtgact ttcagtggga gatggaagtt tttcagagaa ctgaactgtg aaaaatgac        820
cttttcctta acttgaagcta cttttaaaat ttgagggtct ggaccaaaag aagaggaata     880
tcaggttgaa gtcaagatga cagataaggt gagagtaatg actaactcca aagatggctt      940
cactgaagaa aaggcatttt aagattttt aaaaatcttg tcagaagatc ccagaaaagt       1000
tctaattttc attagcaatt aataaagcta tacatgcaga aatgaataca acagaacact      1060
gctctttta gatttatttt gtacttttg gcctgggata tgggttttaa atggacattg        1120
tctgtaccag cttcattaaa ataaacaata tttgtcaaaa atcgtactaa tgcttatttt      1180
attttaattg tatagaaaga aaaaaatgcc taaaataagg ttttcttgca taaaatactgg    1240
aaattgcaca tggtacaaat ttttttcttca ttactgtaca gggatgatgt taatgacttt   1300
ggagcactga aagttactga agtgccttct gaatcaagga tttaattaag gccacaatac     1360
cttttttaata ctcagtgttc tgttttttttt aaaaacttga tattcccgta tggtgcatat  1420
ttgatacagg tacccaatca tgttggataa atgggcatgc cagcc                     1465
```

<210> SEQ ID NO 2
<211> LENGTH: 101
<212> TYPE: PRT
<213> ORGANISM: Homo sapiens

<400> SEQUENCE: 2

```
Met Ser Asp Gln Glu Ala Lys Pro Ser Thr Glu Asp Leu Gly Asp Lys
 1               5                  10                  15

Lys Gln Gly Glu Tyr Ile Lys Leu Lys Val Ile Gly Gln Asp Ser Ser
             20                  25                  30

Glu Ile His Phe Lys Val Lys Met Thr Thr His Leu Lys Lys Leu Lys
         35                  40                  45

Glu Ser Tyr Cys Gln Arg Gln Gly Val Pro Met Asn Ser Leu Arg Phe
     50                  55                  60

Leu Phe Glu Gly Gln Arg Ile Ala Asp Asn His Thr Pro Lys Glu Leu
 65                  70                  75                  80
```

-continued

Gly Met Glu Glu Glu Asp Val Ile Glu Val Tyr Gln Glu Gln Thr Gly
            85                  90                  95

Gly His Ser Thr Val
            100

<210> SEQ ID NO 3
<211> LENGTH: 774
<212> TYPE: DNA
<213> ORGANISM: Homo sapiens
<220> FEATURE:
<221> NAME/KEY: modified_base
<222> LOCATION: (53)
<223> OTHER INFORMATION: Y = C or T
<220> FEATURE:
<221> NAME/KEY: modified_base
<222> LOCATION: (689)
<223> OTHER INFORMATION: N = A, C, G or T
<220> FEATURE:
<221> NAME/KEY: modified_base
<222> LOCATION: (739)
<223> OTHER INFORMATION: N = A, C, G or T
<220> FEATURE:
<221> NAME/KEY: modified_base
<222> LOCATION: (744)
<223> OTHER INFORMATION: N = A, C, G or T

<400> SEQUENCE: 3
cggcacgagg gtgctgcttg tgtgctcgtt tggtgcggac ctggtacctc ttyttgtgaa      60
gcggcagctg aggagactcc ggcgctcgcc atggccgacg aaaagcccaa ggaaggagtc     120
aagactgaga acaacgatca tattaatttg aaggtggcgg ggcaggatgg ttctgtggtg     180
cagtttaaga ttaagaggca tacaccactt agtaaactaa tgaaagccta ttgtgaacga     240
cagggattgt caatgaggca gatcagattc cgatttgacg ggcaaccaat caatgaaaca     300
gacacacctg cacagttgga aatggaggat gaagatacaa ttgatgtgtt ccaacagcag     360
acgggaggtg tctactgaaa agggaacctg cttctttact ccagaactct gttctttaaa     420
gaccaagatt acattctcaa ttagaaaact gcaatttggt tccaccacat cctgactact     480
accgtatagt tttctctatt ctttcatttc ccccttcccc attcctttat tgtacataaa     540
gtaactggta tatgtgcaca agcatattgc attttttttt tttttaacta aacagccaat     600
ggtatgtttt gattgacatc caagtggaga cggggatggg gaaaaatact gattctgtgg     660
aaaatacccc cctttctccc attagtggnc atgctccatt cagcccttaa acctttataa     720
tcccaggtaa ggtaattttng cccncaccgg ttttacccaa aaaaaaaaaa actt          774

<210> SEQ ID NO 4
<211> LENGTH: 95
<212> TYPE: PRT
<213> ORGANISM: Homo sapiens

<400> SEQUENCE: 4

Met Ala Asp Glu Lys Pro Lys Glu Gly Val Lys Thr Glu Asn Asn Asp
  1               5                  10                  15

His Ile Asn Leu Lys Val Ala Gly Gln Asp Gly Ser Val Val Gln Phe
             20                  25                  30

Lys Ile Lys Arg His Thr Pro Leu Ser Lys Leu Met Lys Ala Tyr Cys
         35                  40                  45

Glu Arg Gln Gly Leu Ser Met Arg Gln Ile Arg Phe Arg Phe Asp Gly
     50                  55                  60

Gln Pro Ile Asn Glu Thr Asp Thr Pro Ala Gln Leu Glu Met Glu Asp
 65                  70                  75                  80

```
Glu Asp Thr Ile Asp Val Phe Gln Gln Gln Thr Gly Gly Val Tyr
            85                  90                  95
```

<210> SEQ ID NO 5
<211> LENGTH: 1733
<212> TYPE: DNA
<213> ORGANISM: Homo sapiens
<220> FEATURE:
<221> NAME/KEY: modified_base
<222> LOCATION: (19)
<223> OTHER INFORMATION: N = A, C, G or T

<400> SEQUENCE: 5

| | | | | | |
|---|---|---|---|---|---|
| ttcggcacag | gcgggaganc | ggcggggccg | aagcgtgaac | tcgcccgctc | cggcttgctt | 60 |
| cccccgcgcc | gcctcccgc | gccgctcgga | agccatgtcc | gaggagaagc | ccaaggaggg | 120 |
| tgtgaagaca | gagaatgacc | acatcaacct | gaaggtggcc | gggcaggacg | gctccgtggt | 180 |
| gcagttcaag | atcaagaggc | acgtcgct | gagcaagctg | atgaaggcct | actgcgagag | 240 |
| gcagggcttg | tcaatgaggc | agatcagatt | caggttcgac | gggcagccaa | tcaatgaaac | 300 |
| tgacactcca | gcacagctga | aatggagga | cgaggacacc | atcgacgtgt | tccagcagca | 360 |
| gacgggaggt | gtgccggaga | gcagcctggc | agggcacagt | ttctagaggg | cccgtcccca | 420 |
| gcccgggccg | tccatcctcg | cattgctgtt | gaatggtgag | cacgtgacca | tgccgaccac | 480 |
| aaaggtgtct | gcggaaactc | gaggacattc | accacgatga | ttttcctctc | tttgatgtac | 540 |
| ttcaagtgca | actcaaaact | atatctgcag | ggatgaatct | gtaacttaaa | ttgggccaat | 600 |
| cagaattgtt | atctttgttc | aggtaaaatg | agttgcaaga | tattgtgggt | acttttgtgt | 660 |
| gctcatttgt | gttttccccc | cctcctacaa | catttttta | accccaaaat | tatagcctga | 720 |
| atgttcgctt | ttagtctggc | cagggatctg | actcctgagt | tggttgcctc | tccctgctc | 780 |
| actccagtca | catagagaat | tggtgttcc | cgcagtgggg | attgcagctg | ttggacaggt | 840 |
| attgggggca | aggttggtag | ggaggacaga | ctgtcacttg | ctgttacagg | cacaggtgat | 900 |
| taaaatgcta | aatattgcaa | atttaagctt | tgtcagtata | tggaaaagtt | gaagggaaaa | 960 |
| tactggaatg | cttcttcaaa | ggttaaaaaa | taaccgagtc | ttttggtaat | ttgaccccac | 1020 |
| gtgctctctg | gccctcaagc | atgtaacctc | ggggtctgag | gcccaggacc | cacccccctg | 1080 |
| ccaccccctcc | caccccactc | cctgctcagt | acctggcgtt | ggtacacagg | caaggattgg | 1140 |
| cacaaccaaa | attggccttt | ttctccctct | taatattgaa | gaaattccca | catttctcat | 1200 |
| ttggtaatgg | tgttgtggcc | tcagatttct | tctagtattt | gcttctgatg | aatgattatg | 1260 |
| gtctatacat | aaaaaagtaa | gactaagtat | tgctgaattt | gcagttatgt | tgtcgtgtat | 1320 |
| aagagctact | tccaagtgtg | gttacaaatg | aacccatgga | atgatgactt | catgttcttc | 1380 |
| tcgtgggttt | gtgccgtgct | gctttccaaa | taggtattga | atttatgcat | tagtctggtg | 1440 |
| atttcagttc | tgtgaaatat | tttgggatct | ataccaatta | aacattttca | tagttctgcc | 1500 |
| tattgtcctt | ccctgaggct | ccattgctgc | ttggtggcca | ttctctgcct | ttttacagtc | 1560 |
| acctgaacaa | tgacccatca | tctcttgctt | gcttgaaatc | ttgctgaaat | gttctcattt | 1620 |
| cctgtttgct | gtatgggctc | gggtgggatg | tttgttggct | ctgttgtgtt | tattcaccaa | 1680 |
| tttgtacatt | atttgttgtc | ctttactact | gtaaacagta | aatatagttt | ggt | 1733 |

<210> SEQ ID NO 6
<211> LENGTH: 103
<212> TYPE: PRT
<213> ORGANISM: Homo sapiens

```
<400> SEQUENCE: 6

Met Ser Glu Glu Lys Pro Lys Glu Gly Val Lys Thr Glu Asn Asp His
  1               5                  10                  15

Ile Asn Leu Lys Val Ala Gly Gln Asp Gly Ser Val Val Gln Phe Lys
             20                  25                  30

Ile Lys Arg His Thr Ser Leu Ser Lys Leu Met Lys Ala Tyr Cys Glu
         35                  40                  45

Arg Gln Gly Leu Ser Met Arg Gln Ile Arg Phe Arg Phe Asp Gly Gln
     50                  55                  60

Pro Ile Asn Glu Thr Asp Thr Pro Ala Gln Leu Arg Met Glu Asp Glu
 65                  70                  75                  80

Asp Thr Ile Asp Val Phe Gln Gln Gln Thr Gly Gly Val Pro Glu Ser
                 85                  90                  95

Ser Leu Ala Gly His Ser Phe
            100

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Arg Gly Ser His His His His His His
  1               5

<210> SEQ ID NO 8
<211> LENGTH: 30
<212> TYPE: DNA
<213> ORGANISM: Homo sapiens

<400> SEQUENCE: 8
cttaggatcc atggcctcgg aagacattgc                                      30

<210> SEQ ID NO 9
<211> LENGTH: 30
<212> TYPE: DNA
<213> ORGANISM: Homo sapiens

<400> SEQUENCE: 9
gtgtgaattc tagaccttgt acagcgtctg                                      30

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

Arg Gly Ser His His His His
  1               5

<210> SEQ ID NO 11
<211> LENGTH: 9
<212> TYPE: PRT
<213> ORGANISM: Influenza virus

<400> SEQUENCE: 11
```

Tyr Pro Tyr Asp Val Pro Asp Tyr Ala
1               5

<210> SEQ ID NO 12
<211> LENGTH: 4
<212> TYPE: PRT
<213> ORGANISM: Homo sapiens

<400> SEQUENCE: 12

His Ser Thr Val
1

<210> SEQ ID NO 13
<211> LENGTH: 101
<212> TYPE: PRT
<213> ORGANISM: Saccharomyces cerevisiae

<400> SEQUENCE: 13

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Ala Thr Tyr
            100

<210> SEQ ID NO 14
<211> LENGTH: 80
<212> TYPE: PRT
<213> ORGANISM: Homo sapiens

<400> SEQUENCE: 14

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Leu Arg
65                  70                  75                  80

<210> SEQ ID NO 15
<211> LENGTH: 76
<212> TYPE: PRT
<213> ORGANISM: Homo sapiens

<400> SEQUENCE: 15

Met Leu Ile Lys Val Lys Thr Leu Thr Gly Lys Glu Ile Glu Ile Asp
1               5                   10                  15

Ile Glu Pro Thr Asp Lys Val Glu Arg Ile Lys Glu Arg Val Glu Glu
            20                  25                  30

```
Lys Glu Gly Ile Pro Pro Gln Gln Arg Leu Ile Tyr Ser Gly Lys
         35                  40                  45

Gln Met Asn Asp Glu Lys Thr Ala Ala Asp Tyr Lys Ile Leu Gly Gly
 50                  55                  60

Ser Val Leu His Leu Val Leu Ala Leu Arg Gly Gly
 65                  70                  75

<210> SEQ ID NO 16
<211> LENGTH: 30
<212> TYPE: PRT
<213> ORGANISM: Homo sapiens

<400> SEQUENCE: 16

Val Gln Asp Leu Ala Gln Leu Val Glu Ala Thr Gly Val Pro Leu
 1               5                   10                  15

Pro Phe Gln Lys Leu Ile Phe Lys Gly Lys Ser Leu Lys Glu
                 20                  25                  30

<210> SEQ ID NO 17
<211> LENGTH: 1518
<212> TYPE: DNA
<213> ORGANISM: Homo sapiens
<220> FEATURE:
<221> NAME/KEY: CDS
<222> LOCATION: (136)..(438)

<400> SEQUENCE: 17
cgaggcgtag cggaagttac tgcagccgcg gtgttgtgct gtcgggaagg ggaaggattt      60 gtaaacccg  agcgaggtt  ctgcttaccc  gaggccgctg  ctgtgcggag  accccgggt     120 gaagccaccg tcatc atg tct gac cag gag gca aaa cct tca act gag gac       171
                Met Ser Asp Gln Glu Ala Lys Pro Ser Thr Glu Asp
                 1                   5                   10 ttg ggg gat aag aag caa ggt gaa tat att aaa ctc aaa gtc att gga        219
Leu Gly Asp Lys Lys Gln Gly Glu Tyr Ile Lys Leu Lys Val Ile Gly
             15                  20                  25 cag gat agc agt gag att cac ttc aaa gtg aaa atg aca aca cat ctc        267
Gln Asp Ser Ser Glu Ile His Phe Lys Val Lys Met Thr Thr His Leu
 30                  35                  40 aag aaa ctc aaa gaa tca tac tgt caa aga cag ggt gtt cca atg aat        315
Lys Lys Leu Lys Glu Ser Tyr Cys Gln Arg Gln Gly Val Pro Met Asn
 45                  50                  55                  60 tca ctc agg ttt ctc ttt gag ggt cag aga att gct gat aat cat act        363
Ser Leu Arg Phe Leu Phe Glu Gly Gln Arg Ile Ala Asp Asn His Thr
                 65                  70                  75 cca aaa gaa ctg gga atg gag gaa gaa gat gtg att gaa gtt tat cag        411
Pro Lys Glu Leu Gly Met Glu Glu Glu Asp Val Ile Glu Val Tyr Gln
             80                  85                  90 gaa caa acg ggg ggt cat tca aca gtt tagatattct ttttattttt              458
Glu Gln Thr Gly Gly His Ser Thr Val
             95                  100 tttcttttcc ctcaatcctt tttattttt aaaatagtt cttttgtaat gtggtgttca        518
aaacggaatt gaaaactggc accccatctc tttgaaacat ctgtaatttt gaattctagt      578
gctcattatt cattattgtt tgttttcatt gtgctgattt tggtgatca agcctcagtc      638 cccttcatat taccctctcc tttttaaaaa ttacgtgtgc acagagaggt cacctttttc     698
aggacattgc atttttcaggc ttgtggtgat aaataagatc gaccaatgca agtgttcata    758
atgactttcc aattggcccct gatgttctag catgtgatta cttcactcct ggactgtgac    818
```

```
tttcagtggg agatggaagt ttttcagaga actgaactgt ggaaaaatga cctttcctta    878
acttgaagct acttttaaaa ttttgagggt ctggaccaaa agaagaggaa tatcaggttg    938
aagtcaagat gacagataag gtgagagtaa tgactaactc caaagatggc ttcactgaag    998
aaaaggcatt ttaagatttt ttaaaaatct tgtcagaaga tcccagaaaa gttctaattt   1058
tcattagcaa ttaataaagc tatacatgca gaaatgaata caacagaaca ctgctctttt   1118
tgattttatt tgtacttttt ggcctgggat atgggtttta aatggacatt gtctgtacca   1178
gcttcattaa aataaacaat atttgtcaaa aatcgtacta atgcttattt tattttaatt   1238
gtatagaaag aaaaaaatgc ctaaaataag gttttcttgc ataaatactg gaaattgcac   1298
atggtacaaa aaaaaaatgc ctaaattact gtacagggat gatgttaatg actttggagc   1358
actgaaagtt actgaagtgc cttctgaatc aaggatttaa ttaaggccac aataccttt    1418
taatactcag tgttctgttt tttttaaaaa cttgatattc ccgtatggtg catatttgat   1478
acaggtaccc aatcatgttg gataaatggg catgccagcc                         1518
```

<210> SEQ ID NO 18
<211> LENGTH: 101
<212> TYPE: PRT
<213> ORGANISM: Homo sapiens

<400> SEQUENCE: 18

```
Met Ser Asp Gln Glu Ala Lys Pro Ser Thr Glu Asp Leu Gly Asp Lys
  1               5                  10                  15

Lys Gln Gly Glu Tyr Ile Lys Leu Lys Val Ile Gly Gln Asp Ser Ser
             20                  25                  30

Glu Ile His Phe Lys Val Lys Met Thr Thr His Leu Lys Lys Leu Lys
         35                  40                  45

Glu Ser Tyr Cys Gln Arg Gln Gly Val Pro Met Asn Ser Leu Arg Phe
     50                  55                  60

Leu Phe Glu Gly Gln Arg Ile Ala Asp Asn His Thr Pro Lys Glu Leu
 65                  70                  75                  80

Gly Met Glu Glu Glu Asp Val Ile Glu Val Tyr Gln Glu Gln Thr Gly
                 85                  90                  95

Gly His Ser Thr Val
            100
```

COMPOSITIONS AND USES FOR A NOVEL CELL-DEATH-PROTECTING PROTEIN

1.0 BACKGROUND OF THE INVENTION

This application is a divisional of U.S. patent application Ser. No. 08/964,162, now abandoned, filed on Nov. 4, 1997, which is a continuing application of U.S. Provisional Application Ser. No. 60/030,302, filed Nov. 5, 1996, the content of which is specifically incorporated herein by reference in its entirety.

The United States government has rights in the present invention pursuant to grant number HL-45851 from the National Institutes of Health.

1.1 Field of the Invention

The present invention relates generally to the field of molecular biology. Disclosed are methods and compositions comprising DNA segments encoding a novel protein, sentrin-1, found to protect against TNF and Fas/APO-1 induced apoptosis. Various methods for making and using these DNA segments, DNA segments encoding synthetically-modified sentrin-1 polypeptides, and native and synthetic sentrin-1 peptides are disclosed, such as, for example, the use of DNA segments as diagnostic probes and templates for protein production, and the use of proteins, fusion protein carriers and peptides in various immunological and diagnostic applications.

1.2 Description of Related Art

Fas/APO-1 (CD95), belongs to the TNF receptor superfamily, which is characterized by cysteine-rich pseudo-repeats in the extracellular domain (Smith et al., 1994). Despite the similarity in the organization of the extracellular domain, the cytoplasmic domain of the TNF receptor superfamily is not conserved implying that different signaling mechanisms must be operative for different receptors. Nonetheless, Fas/APO-1 and TNFR1 share a common cytoplasmic signaling motif called the "death domain" (Itoh et al., 1991; Itoh and Nagata, 1993; Tartaglia et al., 1993). Deletion or mutation in the death domain abolishes the ability of these receptors to transduce an apoptosis signal.

Several laboratories have reported the cloning of death-domain associated proteins, including FADD/MORT1, TRADD, and RIP (Boldin et al., 1995; Chinnaiyan et al., 1995; Hsu et al., 1995; Stanger et al., 1995). Following ligation of Fas on the cell surface by either antibody or ligand, a complex called DISC (Death-Inducing Signal Complex), which include Fas, FADD/MORT1 and FLICE/MACH, is formed via death-domain or death-effector domain-mediated interaction (Kischkel et al., 1995; Muzio et al., 1996; Boldin et al., 1996). Ligand-induced association of TNFR1 with TRADD, RIP, and FADD/MORt1 has also been demonstrated (Hsu et al., 1995; Hsu et al., 1996a; Hsu et al., 1996b). Taken together, death-domain/death domain interactions initiate a platform for the assembly of signaling complexes which are essential for apoptosis induction or NF-kB signaling.

Several non-death-domain containing proteins which bind to either Fas/APO-1 or TNFR1 have also been reported. FAP-1 is a tyrosine phosphatase which binds to the C-terminal 15 amino acids of Fas/APO-1, a negative regulator of cell death signaling (Sato et al., 1995). Overexpression of FAP-1 could inhibit Fas/APO-1 signaling. FAF1, another novel protein that binds to the Fas/APO-1 cell death domain, facilitates Fas/APO-1-mediated apoptosis (Chu et al., 1995). Furthermore, there are a large number of proteins which regulate apoptosis either positively or negatively, but do not bind to the cytoplasmic domain of either Fas/APO-1 or TNFR1. They include the IAP's (Liston et al., 1996), ALG (Vito et al., 1996), members of the Bcl-2 family (Oltvai and Korsmeyer, 1994), and inhibitors of the ICE family, such as CrmA and P35 (Clem and Miller, 1994). Full integration of these proteins in the cell death signaling pathway is yet to be achieved. However, the functions of these proteins are yet to be completely elucidated and their interrelationships remain undefined.

PML, a RING finger protein with tumor suppressor activity, has been implicated in the pathogenesis of acute promyelocytic leukemia that arises following a reciprocal chromosomal translocation that fuses the PML gene with the retinoic acid receptor α (RARα) gene. Immunocytochemical analysis has demonstrated that PML is co-localized with a novel ubiquitin-like protein in the nuclear bodies, which could be disrupted by the PML-RARα fusion protein. The physical nature of this co-localization is unknown. Using a COS cell expression system, the inventors show that PML is covalently modified by the sentrin family of ubiquitin like proteins, but not by NEDD8 or ubiquitin.

Chromosomal translocation (Larson et al., 1984; Lapenta et al., 1997), detected in the majority of patients with acute promyelocytic leukemia, generates a fusion protein composed of portions of the retinoic acid receptor α (RARα) and RING finger protein called PML (Larson et al., 1984; de The et al., 1991; Kakizuka et al., 1991; Kastner et al., 1992). In cell lines derived from patients with acute promyelocytic leukemia, the nuclear bodies are disrupted into a microparticulate pattern, which is reversible by treatment with retinoic acid (Weis et al., 1994; Dyck et al., *Cell,* 1994). PML has also been shown to suppress the transformation of NIH3T3 cells by the activated neu oncogene (Liu et al., 1995). Using full length PML as bait in a yeast two hybrid interaction screening, Boddy et al. (1996) have isolated a novel ubiquitin-like protein, called PIC1 that interacted specifically with PML in the yeast interaction assay (Boddy et al., 1996). They have further shown that PIC1 was co-localized with PML to the nuclear bodies. In NB4 cells, which are derived from acute promyelocytic leukemia, there was no significant co-localization of PIC1 with PML. However, following retinoic acid treatment, a significant relocalization of PIC1 with PML was observed. These observations suggest that the association of PIC1 with PML may play an important role in the pathogenesis of acute promyelocytic leukemia.

Protein modification by ubiquitin is critical for targeting proteins to be degraded by proteasomes (Coux et al., 1996; Hershko and Ciechanover, 1992; Jentsch, 1992). Conjugation of ubiquitin to other proteins requires initial activation of the conserved C-terminal Gly residue catalyzed by a specific ubiquitin-activating enzyme, E1. An intermediate, ubiquitin adenylate, is formed by displacement of PPi from ATP. Ubiquitin adenylate is then transferred to a thiol site in E1 with release of AMP. Next, ubiquitin is transferred to a family of ubiquitin-carrier proteins, E2, through transacylation. Finally, ubiquitin is transferred from E2 to its target protein through an isopeptide linkage with the ε-amino group of the Lys residue of the target protein. The transfer of ubiquitin from E2 to the target protein may require the participation of a ligase, E3. The internal Lys of ubiquitin, in particular Lys48, can also be modified by another ubiquitin to form multiubiquitin chains which may be crucial for proteosome recognition (Finley et al., 1994). In recent years, ubiquitination has been shown to play a critical role in antigen processing, in the regulation of cell cycle, in receptor endocytosis, and in signal transduction (Hochstrasser, 1996; Rock et al., 1994; Murray, 1995).

Ubiquitin is not the only molecular tag for protein modification. Another ubiquitin-like protein, UCRP, has been shown to be conjugated to a large number of intracellular proteins (Haas et al., 1987). UCRP contains two ubiquitin domains and is inducible by type 1 interferons. There is evidence for a distinct pathway of UCRP conjugation that is parallel to ubiquitination (Narasimhan et al., 1996).

2.0 SUMMARY OF THE INVENTION

The present invention relates to a novel protein that affects apoptosis in a manner opposite to that of known death domain-associated proteins. As used herein, this protein, named sentrin, represents a new class of proteins which have the ability to protect or guard cells from TNF or Fas/APO induced cell death. In particular, the invention relates to proteins similar to or highly homologous to the sentrin-1 polypeptide sequence identified in SEQ ID NO:2.

In a preferred embodiment, the invention concerns an isolated human, murine, or yeast sentrin polypeptide that inhibits TNF receptor or Fas/APO-induced apoptosis. Preferably, the sentrin polypeptide is a sentrin-1, sentrin-2, or sentrin-3, polypeptide, with sentrin-1 polypeptides being highly preferred. Alternatively, the sentrin polypeptide may comprise a contiguous amino acid sequence from SEQ ID NO:2. Highly preferred contiguous amino acid sequences comprise at least about 10 or 20 contiguous amino acid residues from SEQ ID NO:2, or even more preferably, at least about 30 to 40 contiguous amino acid residues from SEQ ID NO:2, or still more preferably, at least about 50 to 60 contiguous amino acid residues from SEQ ID NO:2, with sequences up to about 70, 80, 90, 100, or even full-length sequences being preferred. An exemplary sentrin-1 polypeptide of the invention comprises the entire amino acid sequence of SEQ ID NO:2. Other polypeptides which are contemplated by the inventor to be useful in the practice of the invention includes sentrin polypeptides which have a high degree of homology to the sequence of SEQ ID NO:2. As such, those polypeptides comprise a primary amino acid sequence which is preferably about 85%, 90%, 95%, or even 98% or more identical to the primary amino acid sequence of the polypeptide disclosed in SEQ ID NO:2.

In another important embodiment, the invention concerns a purified nucleic acid segment which encodes a whole or a portion of a sentrin polypeptide, and preferably, a sequence which encodes a whole or a portion of a human, murine, or yeast sentrin polypeptide. Highly preferred nucleic acid segments are those which encode a whole or a portion of a sentrin-1, sentrin-2, or sentrin-3 polypeptide. An exemplary nucleic acid segment is a polynucleotide such as that disclosed in SEQ ID NO:1, or any nucleic acid sequence which encodes the polypeptide of SEQ ID NO:2, or any contiguous polypeptide sequence contained within the sequence of SEQ ID NO:2, or a sequence which is complementary to any such nucleic acid segment, or alternatively, any nucleic acid segment which hybridizes to the nucleic acid segment under the hybridization conditions described herein. Preferably, the nucleic acid segments of the invention will have a high degree of sequence homology or identity to the sequence of SEQ ID NO:1, and will hybridize to the sequence of SEQ ID NO:1 under both low and high stringency hybridization conditions.

In one embodiment, the polynucleotide will encode a polypeptide having an amino acid sequence of at least about 10, 15, or 20 contiguous amino acids from SEQ ID NO:2. More preferably, the polynucleotide will encode a polypeptide having an amino acid sequence of at least about 25, 30, or 35 contiguous amino acids from SEQ ID NO:2, and more preferably still, will encode a polypeptide having an amino acid sequence of at leat about 40, 50, or 60 contiguous amino acids from SEQ ID NO:2. An exemplary nucleic acid segment encoding such a sentrin polypeptide is exemplified in the human sentrin-1 polypeptide disclosed in SEQ ID NO:1. The nucleic acid segments and polynucleotides of the present invention are preferably DNA, cDNA, RNA, or mRNA segments, with cDNA, DNA and mRNA segments being highly preferred.

A further aspect of the invention concerns a recombinant vector and a transformed host cell which comprises a nucleic acid segment which encodes a whole or a portion of a sentrin polypeptide, and preferably, a sequence which encodes a whole or a portion of a human, murine, or yeast sentrin polypeptide. Highly preferred recombinant vectors include those plasmids, phage, YACs, BACs, cosmids, phagemids, and the like which contain within its DNA sequence, (a) a nucleic acid segment which encodes a whole or a portion of a sentrin-1, sentrin-2, or sentrin-3 polypeptide; (b) a nucleic acid sequence which encodes the polypeptide of SEQ ID NO:2; (c) a nucleic acid sequence which encodes any contiguous polypeptide sequence contained within the sequence of SEQ ID NO:2; (d) a nucleic acid sequence which is complementary to a contiguous nucleic acid segment from SEQ ID NO:1, or (e) a nucleic acid sequence which hybridizes to the sequence of SEQ ID NO:1 under the hybridization conditions described herein. Preferably, the nucleic acid segment contained within such a recombinant vector will have a high degree of sequence homology or identity to the sequence of SEQ ID NO:1, and will hybridize to the sequence of SEQ ID NO:1 under both low and high stringency hybridization conditions. Thus the homologous nucleic acid segments obtained through hybridization to nucleic acid segments derived from SEQ ID NO:1 will be substantially complementary to the particular nucleic acid segment used to identify the segment via hybridization methodology. "Substantially complementary" sequences will be those that typically have at least about 75 or 80% homology to the sequence of SEQ ID NO:1, and more preferably will have at least about 85 or 90% homology to the sequence of SEQ ID NO:1, and most preferably, those having at least about 95% or higher sequence homology to the sequence of SEQ ID NO:1.

Highly preferred recombinant vectors and transformed host cells are those in which the sentrin nucleic acid sequence is operatively linked to a promotor, the promoter expressing the nucleic acid sequence. Preferably, the recombinant host cell is a prokaryotic cell, such as a bacterium, or alternatively, an eukaryotic cell such as an animal, plant, insect, or yeast cell. Preferred animal cells are mammalian cells such as those derived from murine or human origins.

Recombinant vectors comprising sentrin nucleic acid segments find particular utility in methods of preparing sentrin polypeptides in a transformed host cell. Such a method generally involves preparing a recombinant vector in which a mammalian or yeast sentrin polypeptide-encoding nucleic acid segment is positioned under the control of a promoter; introducing the recombinant vector into a host cell; culturing the host cell under conditions effective to allow expression of the encoded polypeptide; and collecting the expressed sentrin polypeptide.

A further aspect of the invention concerns a nucleic acid composition which is characterized as: an isolated nucleic acid segment comprising a sequence region that consists of at least 14 contiguous nucleotides that have the same sequence as, or are complementary to, 14 contiguous nucleotides of SEQ ID NO:1; or an isolated nucleic acid segment of from 14 to about 10,000 nucleotides in length that hybridizes to the nucleic acid segment of SEQ ID NO:1; or the complement thereof, under standard hybridization conditions. Preferably, the nucleic acid segment is defined as comprising a nucleic acid segment of from 14 to about 10,000 nucleotides in length that hybridizes to the nucleic acid segment of SEQ ID NO:1, or the complement thereof, under standard hybridization conditions. Segment lengths of at least about 20, 30, 40, 50, 60, 70, 80, 90, 100, 200, 300, 400, or 500 nucleotides or more are particularly useful as probes, primers, or templates for DNA or RNA synthesis. In certain embodiments, the inventors contemplate that the nucleic acid compositions of the invention may be up to about 10,000 basepairs in length, or alternatively, may be shorter segments such as those up to about 5000, 4000, 3000, 2000, 1000 or so base pairs in length. For certain uses, even smaller segments such as those up to about 900, 800, 700, 600, 500, 400, 300, 200, or even 100 base pairs or so in length may find particular utility or be particularly desirable for certain uses.

In an important embodiment, the invention also provides a method for detecting a nucleic acid sequence encoding a sentrin polypeptide. The method generally involves obtaining sample nucleic acids suspected of encoding a sentrin polypeptide; contacting the sample nucleic acids with an isolated nucleic acid segment encoding the sentrin polypeptide under conditions effective to allow hybridization of substantially complementary nucleic acids; and detecting the hybridized complementary nucleic acids thus formed. The sample nucleic acids may be located within a cell, or may be separated from a cell prior to contact. Typically, the sentrin polypeptide-encoding nucleic acid segment may also comprise a detectable label, whereby the hybridized complementary nucleic acids may be detected by detecting the label. A nucleic acid detection kit represents a further aspect of the invention. Such a kit may contain in suitable container means, one or more isolated sentrin nucleic acid segments, one or more detection reagents, and optionally one or more restriction or polymerizing enzymes.

A further aspect of the invention involves a method of detecting a ubiquitin conjugating enzyme polypeptide. The method generally involves contacting the polypeptide with an amount of a sentrin-1 polypeptide composition effective to bind the ubiquitin conjugating enzyme polypeptide, and detecting the complexes so bound.

Also provided is a method of detecting a PML polypeptide. This method generally involves contacting the polypeptide suspected of being a PML polypeptide with an amount of a sentrin-1 polypeptide composition effective to bind the polypeptide, and detecting the complexes so bound. The method may typically involve obtaining a sample suspected of containing a sentrin polypeptide; contacting the sample with a first antibody that specifically binds to a sentrin polypeptide under conditions effective to form an immune complex; and detecting the immune complex so formed.

Another aspect of the invention is a method of inhibiting or preventing TNFR- or Fas/Apo-1 induced apoptosis in a cell. This method typically involves administering to a mammal, such as a human, a pharmaceutical composition comprising an amount of a sentrin polypeptide composition effective to inhibit or prevent the apoptosis.

A method of inhibiting or modulating sentrin polypeptide function in a mammal, comprising administering to the mammal a composition comprising an antibody that specifically binds a sentrin polypeptide.

A method of determining the aggressiveness of a tumor, comprising determining the amount of a sentrin polypeptide produced by a cell and comparing the amount so produced with a normal cell wherein overexpression of the protein is indicative of the aggressiveness of the tumor.

Another embodiment of the invention is a method of producing cell-death in a tumor cell. This method comprises contacting the tumor cell with a composition effective to prevent sentrinization in the cell. The sentrinization may be prevented by blocking the interaction of sentrin and Ubc9, and the composition may comprise a C-terminal peptide fragment of sentrin, or alternatively, a small inhibitor molecule which interacts with sentrin to prevent sentrinization from occurring in the cell. Preferably, the composition comprises an amount of a polypeptide effective to inhibit TNFR- or Fas/APO-1-induced apoptosis.

2.1 Sentrin Affects Apoptosis

Sentrin-1 has several unique features which distinguish it from known death-domain associated proteins. Sentrin-1 does not comprise any known death domain sequences, yet it binds to both Fas/APO-1 and TNFR1, but not CD40 or FADD/MORT1. Sentrin-1 protects the cells from both anti-Fas/APO-1 and TNF-mediated cell death. While the precise mechanism whereby sentrin-1 blocks cell death signaling is not clear, sentrin-1 appears to prevent binding of FADD/MORT1 or TRADD or other proteins to Fas/APO-1 and TNFR1 thus interrupting the signaling pathway. Alternatively, a more complex regulation mediated by sentrin-1 can be envisioned Sentrin most likely does not compete with the ubiquitin mediated pathway of protein degradation. Ubiquitination and "sentrinization" represent distinct pathways each with a specific target.

The identification of sentrin-1 thus has provided an important insight into the regulation of cell death signaling and identifies for the first time a regulatory protein for potential control of apoptosis.

2.2 Sentrin-1 DNA Segments as Hybridization Probes and Primers

In addition to their use in directing the expression of proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as; or is complementary to, a 14 nucleotide long contiguous DNA segment of SEQ ID NO:1 will find particular utility. Longer contiguous identical or complementary sequences, e.g., those of about 20, 30, 40, 50, 100, 200, 300, 400, 500 bp, etc. (including all intermediate lengths and up to and including the full-length sequence of 507 basepairs will also be of use in certain embodiments.

The ability of such nucleic acid probes to specifically hybridize to protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 10 to about 14, or from about 15 to about 20, or about 30, or about 40, or about 50, or even of from about 100 to about 200 nucleotides or so, identical or complementary to DNA sequences of SEQ ID NO:1, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequencers of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating sentrin-1 protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate sentrin-1 protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

The present invention provides oligonucleotide hybridization probes useful in screening genomic and other nucleic acid libraries for DNA sequences encoding peptides, polypeptides, and proteins having activity the same or similar to that of sentrin-1, which probes can be designed based on the sequences provided herein. In particular embodiments, such probes may range from about 16 to about 28 nucleotides in length, generally about 16 nucleotides in length, more typically about 20 nucleotides in length, preferably about 24 nucleotides in length, and more preferably about 28 nucleotides in length. Preferably, these probes specifically hybridize to genomic DNA and other DNA sequences encoding peptides, polypeptides, or proteins having the same or similar activity as that of sentrin-1. Such oligonucleotide probes can be synthesized by automated synthesis, and may be conveniently labeled at the 5' end with a reporter molecule such as a radionuclide, e.g., $^{32}$P, or biotin.

Oligonucleotide probes such as those mentioned may be used to probe genomic or cDNA libraries. Genomic libraries for example may be constructed by fragmenting or digesting genomic DNA with a restriction enzyme such as Sau3A, ligating the DNA fragments so obtained into a suitable vector such as lambda phage and expressing in a suitable host cell, typically *E. coli*. cDNA libraries represent complementary DNA copies of mRNA and are often preferred because the clones obtained are free of the introns or other noncoding sequences found in genomic DNA. In any event, construction of genomic and cDNA libraries are well known to those skilled in the art.

Once constructed, the library may be plated as colonies or phage, depending upon the vector employed, and the recombinant DNA transferred to nylon or nitrocellulose membranes. Following denaturation, neutralization, and fixation of the DNA to the membrane, the membrane is hybridized with the labeled probe (reporter molecule). Following this, the membrane is washed, and the reporter molecule detected. Colonies or phage harboring hybridizing DNA are then isolated and propagated. Candidate clones or PCR™-amplified fragments may be verified as comprising DNA encoding sentrin-1 or related peptides, polypeptides, or proteins having activity the same as or similar to that of sentrin-1 by a variety of means. For example, the candidate clones may be hybridized with a second, non-overlapping probe, or subjected to DNA sequence analysis. The activity of the peptide, polypeptide, or protein encoded thereby can be assessed by cloning and expression of the DNA in an appropriate host such as yeast or *E. coli*, followed by isolation of the peptide, polypeptide, or protein, and assay of the activity thereof by methods such as that described herein. By such means, nucleic acids encoding sentrin-1 or peptides, polypeptides, or proteins biologically functionally equivalent thereto, useful in controlling or preventing apoptosis may be isolated.

Appropriately designed degenerate oligonucleotides may be used to screen genomic libraries directly, and the isolated coding sequences may be incorporated into transformation/expression vectors. Genomic DNAs and cDNAs isolated from humans and other mammals may be probed using degenerate oligonucleotide sequences based on the amino acid sequence (SEQ ID NO:2) of sentrin-1. The probes may be used in conjunction with PCR™ technology employing reverse transcriptase to amplify hybridizable cDNAs. cDNAs are easily cloned in appropriate transformation/expression vectors and introduced into suitable host cells, e.g., mammalian cells. The polypeptides encoded by the DNAs can be expressed in the transformed cells and isolated using established procedures including polyacrylamide gel electrophoresis and Western blots.

Alternatively, degenerate oligonucleotides may be used as probes to screen cDNA libraries from eukaryotic cells in, for example, lambda phage vectors such as I ZapII (Stratagene, La Jolla, Calif.). The cDNA isolated in this manner may be transferred to an appropriate transformation/expression vector for introduction into a host cell.

2.3 Recombinant Vectors and Protein Expression

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a sentrin-1 protein or peptide in its natural environment. Such promoters may include promoters normally associated with other genes, and/or promoters isolated from any bacterial, viral, eukaryotic, or cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of sentrin-1 peptides or epitopic core regions, such as may be used to generate anti-sentrin-1 protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:2.

2.4 Antibody Compositions and Methods of Making

In particular embodiments, the inventors contemplate the use of antibodies, either monoclonal or polyclonal which bind to the sentrin-1 proteins disclosed herein. Means for preparing and characterizing antibodies are well known in the art (See, e.g., Antibodies: A Laboratory Manual, Cold Spring Harbor Laboratory, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-benzoyl-N-hydroxysuccinimide ester, carbodiimide and bis-diazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes may be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and tittering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (vol./vol.) PEG, (Gefter et al., 1977). The use of electrically induced fusion methods is also appropriate (Goding, 1986, pp. 71–74).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two wk. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb-production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body-fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.5 Elisas and Immunoprecipitation

ELISAs may be used in conjunction with the invention. In an ELISA assay, proteins or peptides incorporating sentrin-1 protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 h, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 h at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-sentrin-1 protein antibodies of the present invention are particularly useful for the isolation of other sentrin-1 protein antigens by immunoprecipitation. Immunoprecipitation involves the separation of the target antigen component from a complex mixture, and is used to discriminate or isolate minute amounts of protein. For the isolation of membrane proteins, cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme substrate pairs.

2.6 Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Particularly useful immunologically-based detection labels for use in conjunction with Western blotting include enzymatically-, radiolabel-, or fluorescently-tagged secondary antibodies against the moiety.

2.7 Sentrin-1 Protein Screening and Detection Kits

The present invention contemplates methods and kits for screening samples suspected of containing sentrin-1 protein polypeptides or sentrin-1 protein-related polypeptides, or cells producing such polypeptides. A kit may contain one or more antibodies of the present invention, and may also contain reagent(s) for detecting an interaction between a sample and an antibody of the present invention. The provided reagent(s) can be radio-, fluorescently- or enzymatically-labeled. The kit can contain a known radiolabeled agent capable of binding or interacting with a nucleic acid or antibody of the present invention.

The reagent(s) of the kit may be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the sentrin-1 proteins or peptides of the present invention may be employed to detect antibodies having reactivity therewith, or, alternatively, antibodies prepared in accordance with the present invention, may be employed to detect sentrin-1 proteins or sentrin-1 protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a sentrin-1 protein or peptide or a sentrin-1 protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of sentrin-1 proteins or related peptides and/or antibodies in a sample. Samples may include cells, cell supernatants, cell suspensions, cell extracts, enzyme fractions, protein extracts, or other cell-free compositions suspected of containing sentrin-1 proteins or peptides. Generally speaking, kits in accordance with the present invention will include a suitable sentrin-1 protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.8 Compositions Epitopic Core Sequences

The present invention is also directed to protein or peptide compositions, free from total cells and other peptides, which comprise a purified protein or peptide which incorporates an epitope that is immunologically cross-reactive with one or more anti-sentrin-1 protein antibodies. In particular, the invention concerns epitopic core sequences derived from sentrin-1 (SEQ ID NO:2) proteins or peptides.

As used herein, the term "incorporating an epitope(s) that is immunologically cross-reactive with one or more anti-sentrin-1 protein antibodies" is intended to refer to a peptide or protein antigen which includes a primary, secondary or tertiary structure similar to an epitope located within a sentrin-1 protein or polypeptide. The level of similarity will generally be to such a degree that monoclonal or polyclonal antibodies directed against the sentrin-1 protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of sentrin-1 protein immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al, 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic sentrin-1 protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to sentrin-1 proteins, and in particular to sentrin-1-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the sentrin-1 protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.9 Biological Functional Equivalents 2.9.1 Polypeptides Comprising Conservative Amino Acid Changes Peptides, polypeptides, and proteins biologically functionally equivalent to sentrin-1 include amino acid sequences containing conservative amino acid changes in the fundamental sequence shown in SEQ ID NO:2. In such amino acid sequences, one or more amino acids in the fundamental sequence is (are) substituted with another amino acid(s), the charge and polarity of which is similar to that of the native amino acid, i.e., a conservative amino acid substitution, resulting in a silent change.

Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental polypeptide sequence can be made by substituting one amino acid within one of these groups with another amino acid within the same group. Biologically functional equivalents of sentrin-1 can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of sentrin-1.

The biologically functional equivalent peptides, polypeptides, and proteins contemplated herein should possess about 80% or greater sequence similarity, preferably about 85% or greater sequence similarity, and most preferably about 90% or greater sequence similarity, to the sequence of, or corresponding moiety within, the fundamental sentrin-1 amino acid sequence.

As indicated, modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated sentrin-1 proteins are contemplated to be useful for increasing the activity of the protein, and consequently increasing the activity and/or expression of the recombinant transgene in a cell. The amino acid changes may be achieved by changing the codons of the DNA sequence, according to the codons given in Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

TABLE 1

| AMINO ACIDS | | | CODONS |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±9 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

2.9.2 Fragments and Variants of Sentrin-1

While the sentrin-1 polypeptide of the present invention preferably comprises the amino acid sequence shown in SEQ ID NO:2, fragments and variants of this sequence possessing the same or similar activity as that of this polypeptide are also encompassed by the present invention. Thus contiguous sequences of 8 or more amino acids in SEQ ID NO:2 may exhibit such activity.

Fragments of sentrin-1 can be truncated forms wherein one or more amino acids are deleted from the N-terminal end, C-terminal end, the middle of the polypeptide, or combinations thereof. These fragments can be naturally occurring or synthetic mutants of sentrin-1 and should retain the activity of sentrin-1. Variants of sentrin-1 include forms wherein one or more amino acids has(have) been inserted into the natural sequence. These variants can also be naturally occurring or synthetic mutants of sentrin-1, and should retain the activity of sentrin-1.

Combinations of the foregoing, i.e., forms of the sentrin-1 polypeptide containing both amino acid deletions and additions, are also encompassed by the present invention. Amino acid substitutions can also be present therein as well. The fragments and variants of sentrin-1 encompassed by the present invention should preferably possess about 70% or greater sequence similarity, more preferably about 80% or greater sequence similarity, and most preferably about 90% or greater sequence similarity, to the corresponding regions of sentrin-1 having the amino acid sequence shown in SEQ ID NO:2.

2.9.3 Other Biologically Functional Equivalent Forms

Other biologically functional equivalent forms of sentrin-1 useful in the present invention include conjugates of the polypeptides, or biologically functional equivalents thereof as described above, with other peptides, polypeptides, or proteins, forming fusion products therewith exhibiting the same, similar, or greater activity as compared with that of sentrin-1 having the amino acid sequence shown in SEQ ID NO:2.

2.10 Protein Compositions

An apoptosis inhibiting composition, comprising an effective amount of one or more of the isolated sentrin-1 polypeptides of the present invention are contemplated. Preferred compositions comprise the amino acid sequence shown in SEQ ID NO:2, and an acceptable carrier. The composition may be used for inhibiting or controlling cell death. The necessary additives, carriers, inert materials, surfactants, solvents, etc., which may be useful in preparing pharmaceutically-acceptable formulations of the compositions of the invention are well known in the art, and may typically be prepared using conventional methods. Using these formulations, it is also possible to prepare mixtures of the present polypeptide with other active substances, such as members of the Bcl-2 family, including Bcl-xL, Mcl-1 and Bcl-2 as well as inhibitors of the family of cysteine proteases.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Interaction pattern of sentrin-1. Yeast two-hybrid system was used to map the interactions between sentrin-1 and proteins of interest. Sentrin-1 interacts with the death domains of Fas/APO-1, TNFR1, but not CD40, or FADD/MORT1. The death domain is shaded. ++ indicates positive interaction and −, no interaction. Fas/APO-1 and FADD/MORT1 interaction were used as positive control in all studies.

FIG. 1B. Northern blot analysis using sentrin's cDNA insert as a probe shows transcript of approximately 1.8 kb expressed in all tissues. Level of message is higher in heart, skeletal muscle, testis, ovary and thymus.

FIG. 2A. Shown is the nucleotide and predicted amino acid sequence of sentrin-1 cDNA (SEQ ID NOS: 17 and 18). Nucleotides are numbered on the left and amino acid residues are numbered on the right. The start codon ATG and the stop codon TAG are single underlined. Amino acids are indicated in the single letter code.

FIG. 2B. Shown is the homology of sentrin-1 and ubiquitin (SEQ ID NOS:2, 13, 14, 15, and 16). A BLAST search of the entire data base through the National Center for Biotechnology Information (Bethesda, Md.) (Altschul et al., 1990) revealed sequence homology of sentrin-1 with the yeast *Saccharomyces cerevisiae* Smt3, ubiquitin, Nedd8, the ubiquitin domain to Bag-1 (37–73). Residues identical between sentrin-1 and Smt3 are shown in bold; Residues identical among all sequences are shaded.

Figure 3:
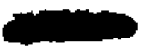

FIG. 3. In-vitro interaction between sentrin-1 and the cell death domains of Fas/APO-1 and TNFR1. Lane 1, GST-Fas/APO-1 (175–319AA), Lane 2, GST-Fas/APO-1 (V238N), Lane 3, GST-TNFR1 (326–426AA), Lane 4, GST-TNFR1 Δ20 (326–406AA). The positions of molecular mass markers (in kilodaltons) are shown on the left of the filters. The position of GST-Fas/APO-1 is indicated by an arrow and that of GST-TNFR1 by an arrow head.

Figure 4A:
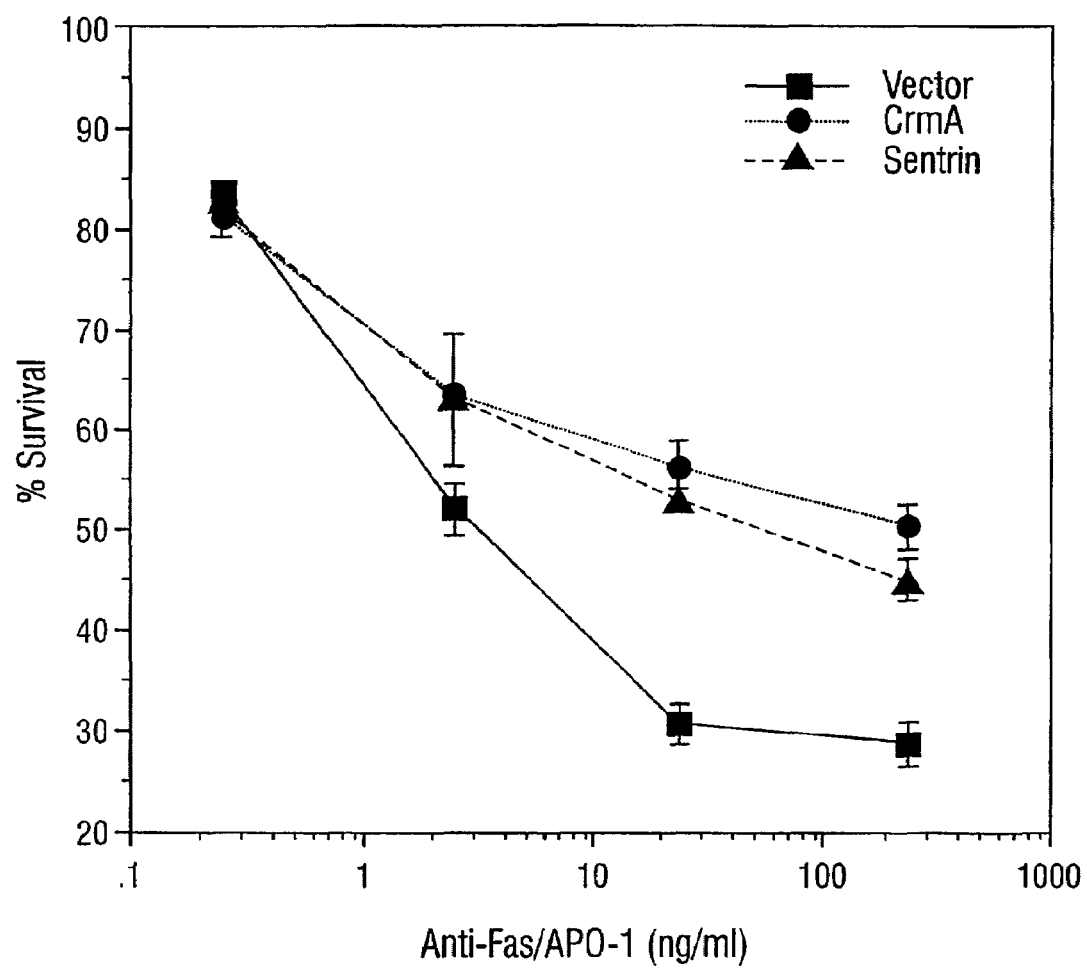

FIG. 4A. Effect of sentrin-1 expression on cell survival after treatment with anti-anti-Fas/APO-1-mediated cell death in BJAB cells (n=6).

Figure 4B:
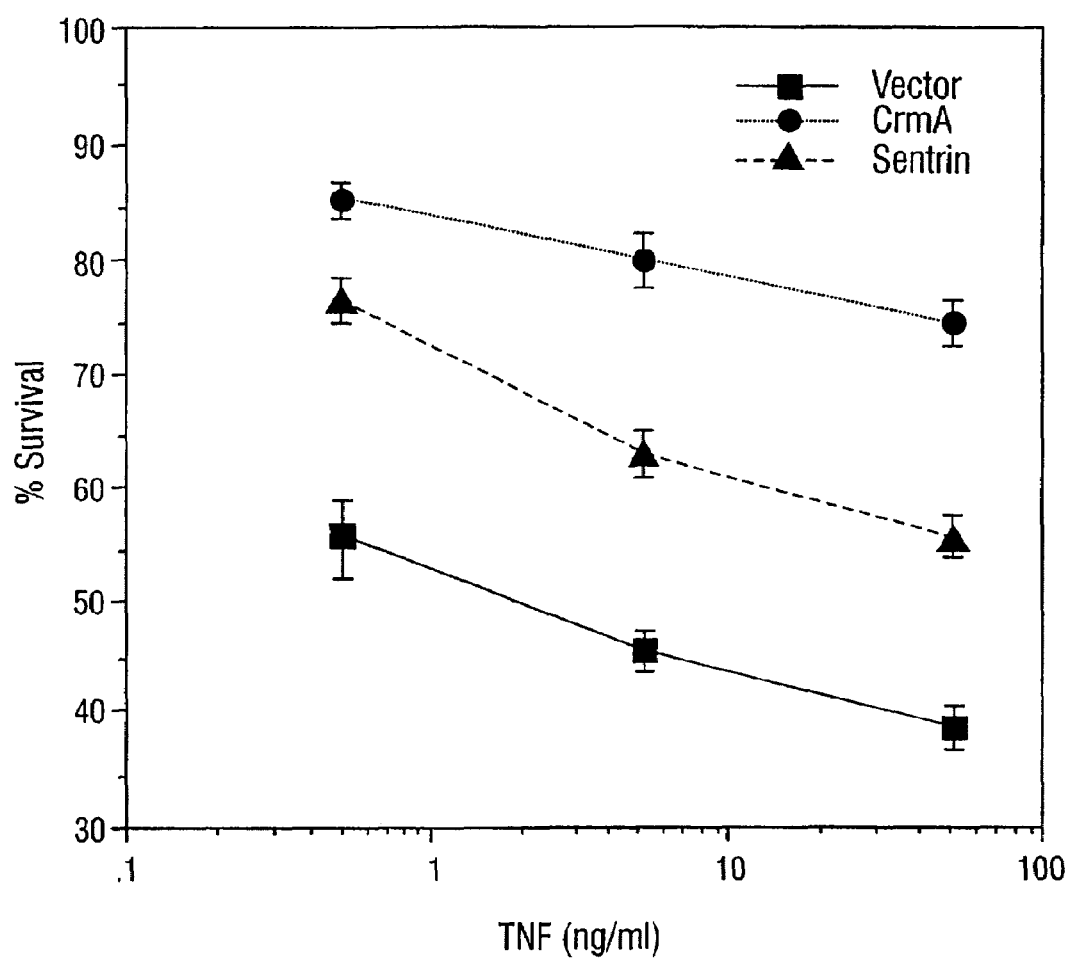

FIG. 4B. Effect of sentrin-1 expression on cell survival after treatment with anti-TNF-induced cell death in L929 cells (n=5). n=number of independent studies. Results are expressed as mean+/−standard error.

Figure 5:
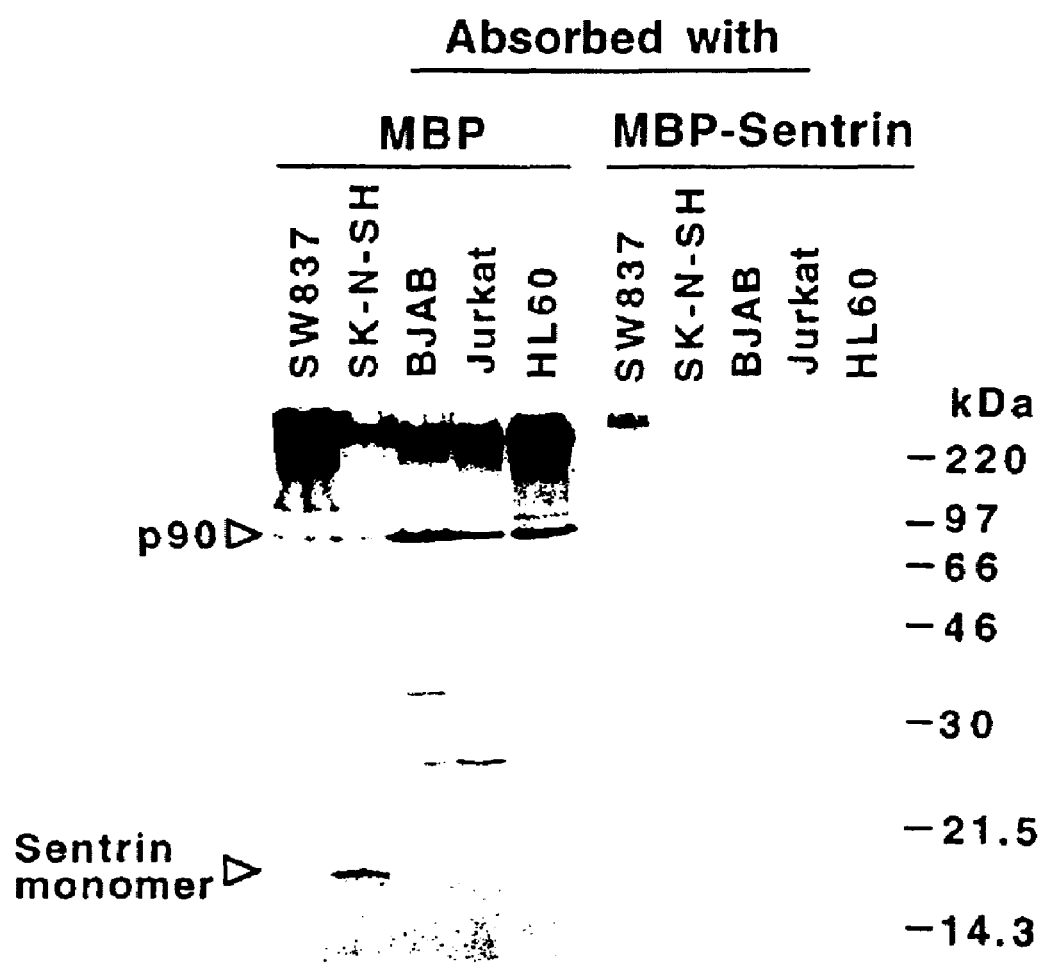

FIG. 5. Western blot analysis of sentrin-1 expression in human cell lines. Total cell lysates were analyzed by Western blotting using antiserum against the N-terminal 21 amino acids of sentrin-1 pre-absorbed with either MBP or MBP-Sentrin-1.

FIG. 6A. Comparison between ubiquitination and sentrinization in COS cell lysates. COS cells were transfected with either empty vector, or pcDNA3/HA-Ubiquitin, or pcDNA3/HA-Sentrin-1. Total cell lysates were analyzed by Western blot analysis using anti-HA mAb (16B12). Sentrin-1 monomer and p90 are indicated by arrow heads. The high molecular weight bands are indicated by bracket with star. Molecular mass standards are expressed in kilodaltons.

FIG. 6B. C-terminal processing of HA-tagged sentrin-1 mutants. Empty vector and plasmid containing wild type sentrin-1, HA-tagged sentrin-1 and various HA-tagged sentrin-1 mutants transiently expressed in COS cells. The lysates were analyzed by Western blot analysis with either anti-HA mAb (16B12) (upper panel) or with anti-sentrin-1 antiserum (lower panel). Molecular mass standards are expressed in kilodaltons.

Figure 7A:
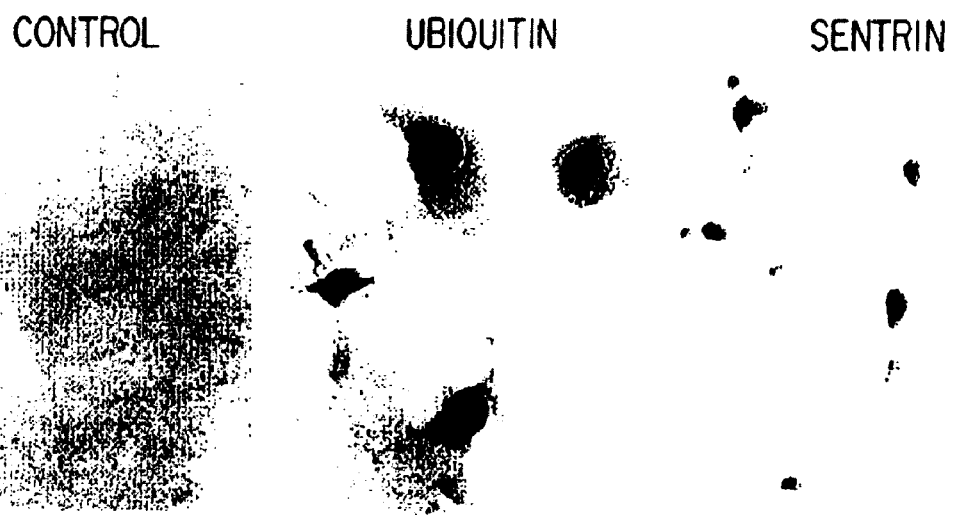

FIG. 7A. Immunocytochemical localization of ubiquitin versus sentrin-1. COS cells transfected with empty vector (Control), plasmid with HA-Ubiquitin cDNA insert-(Ubiquitin), or plasmid with HA-Sentrin-1 cDNA insert (Sentrin-1) were stained with anti-HA mAb (16B12) as described.

Figure 7B:
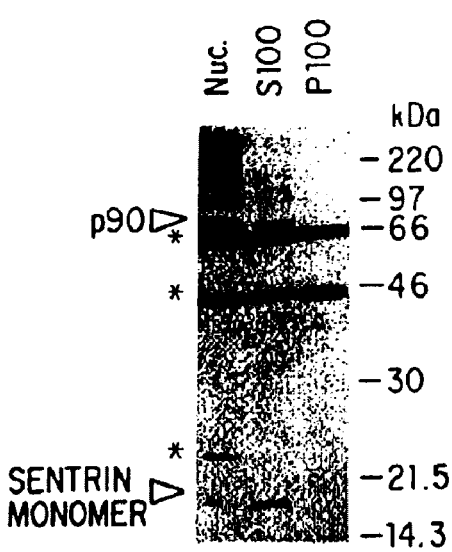

FIG. 7B. Western blot analysis of subcellular fractionations. COS cells were transfected with plasmid containing HA-tagged wild type sentrin-1 insert. Nuclear fraction (Nuc.), cytosolic fraction (S100), or P100 was prepared as described and analyzed by Western blot analysis using anti-HA mAb (12CA5). Non-specific bands are indicated by an asterisk. Molecular mass standards are expressed in kilodaltons.

Figure 8:
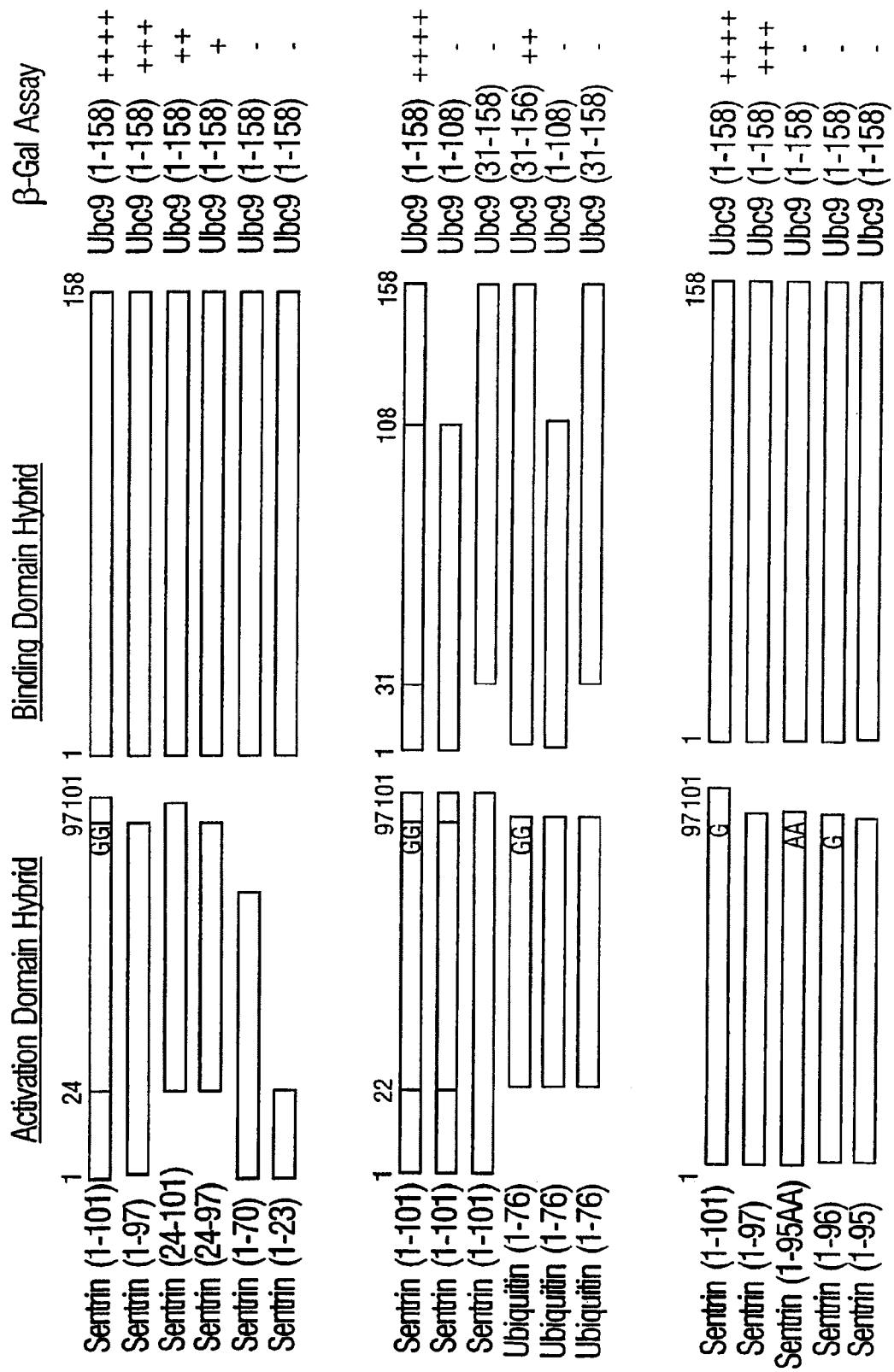

FIG. 8. Mapping of the interaction of sentrin-1 with Ubc9 using the yeast two hybrid assay. ++++ color change in 45 min; +++ color change in 2 h; ++ color change in 6 h; + color change in 12 h; – no color change or color change>24 h. All of the interactions have been repeated at least three times.

Figure 9:
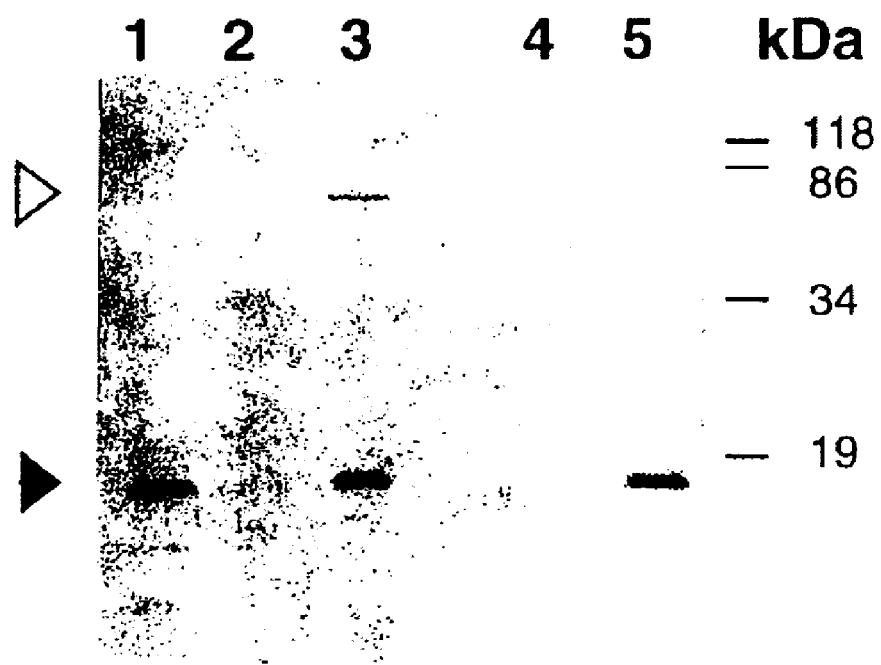

FIG. 9. In vitro interaction of sentrin-1 with Ubc9. In vitro translated sentrin-1 (lane 1) was precipitated by GST-Ubc9 (lane 3), but not by GST alone (lane 2). The positions of labeled sentrin-1 (18 kDa) (closed arrowhead) and the GST-Ubc9-sentrin-1 conjugate (60 kDa) (open arrowhead) are indicated. Lanes 1–3 were run in non-reducing conditions. Lane 4, sentrin-1 precipitated by GST; Lane 5, sentrin-1 precipitated by GST-Ubc9, Lanes 4 and 5 were treated with 5% β-mercaptoethanol.

Figure 10:
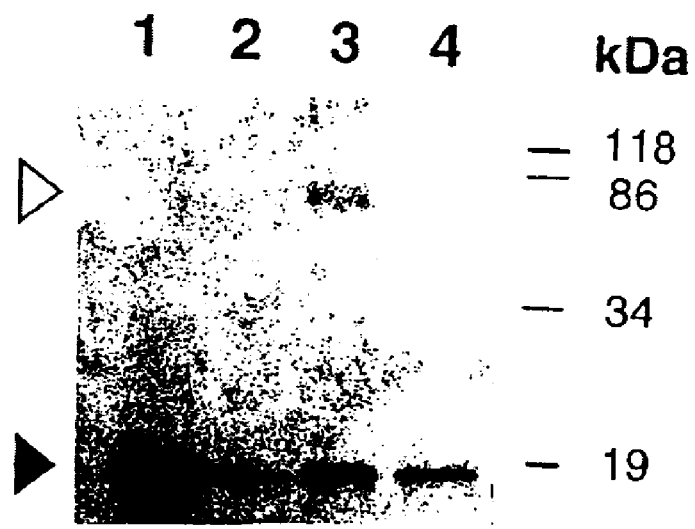

FIG. 10. In vitro interaction of sentrin-1 with Ubc9 and Ubc9(C93S). In vitro translated sentrin-1 (lane 1) was precipitated by GST (lane 2), GST-Ubc9 (lane 3), and GST-Ubc9(C93S) (lane 4). The positions of labeled sentrin-1 (18 kDa) (closed arrowhead) and the GST-Ubc9-sentrin-1 conjugate (60 kDa) (open arrowhead) are indicated.

Figure 11A:
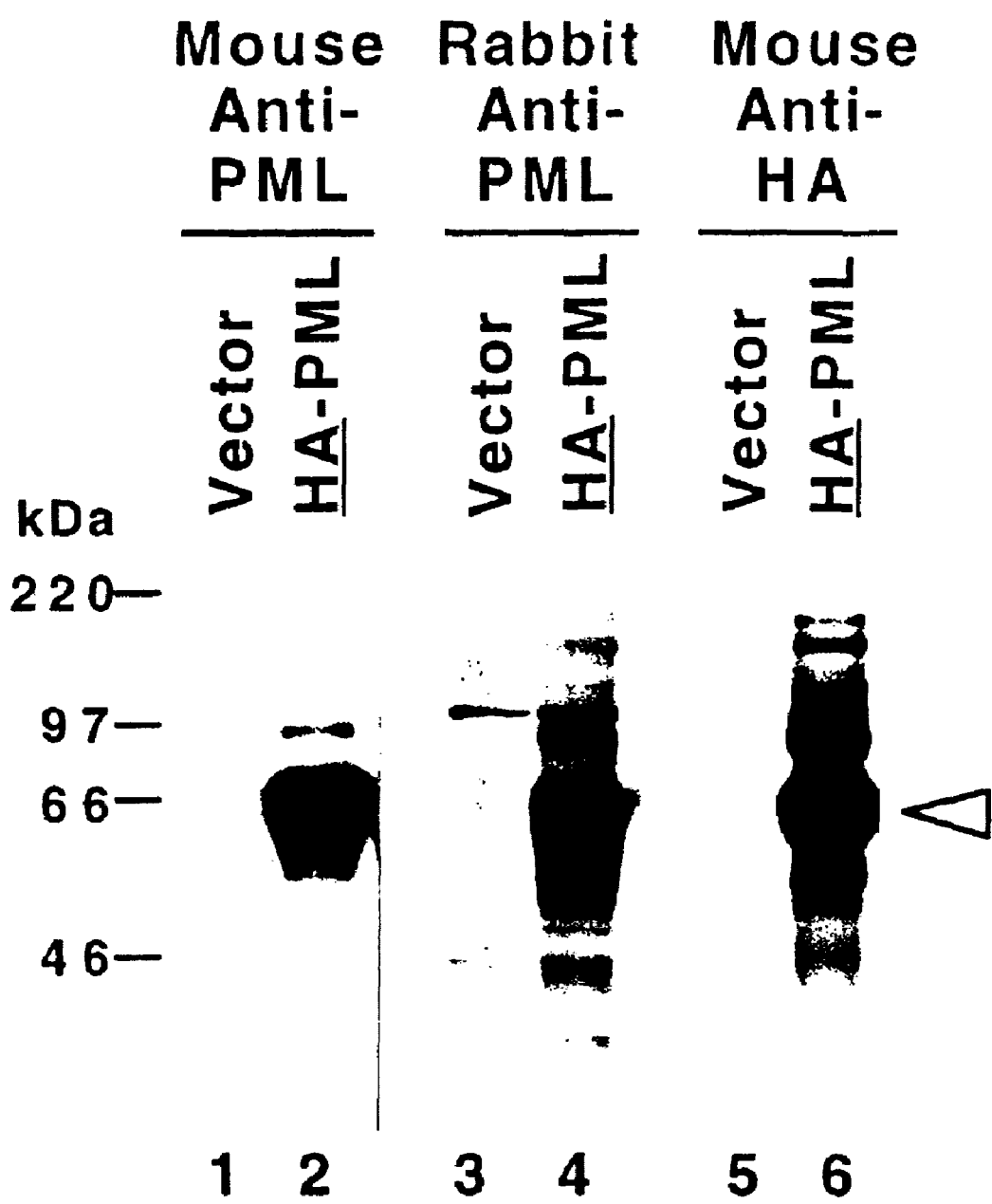

FIG. 11A. Modification of PML by sentrin-1. COS cells were transfected with empty vector (lanes 1, 3, 5) or with plasmid containing cDNA insert encoding HA-. PML (lanes 2, 4, 6) and the lysates were analyzed by SDS-PAGE under reducing condition, followed by Western blotting (HA-tagged PML was expressed in COS cells by transfection with pcDNA3/HA-PML as described (Kamitani et al., 1997a). The full-length cDNA of PML was prepared from the plasmid pMAMneoPML (Mu et al., 1994), and ligated into pcDNA3/HA-N (Kamitani et al., 1997a; Kamitani et al., 1997b) or pcDNA3/RH-C to generate pcDNA3/HA-PML or pcDNA3/PML-RH). Anti-mouse PML monoclonal antibody (Santa Cruz Biotechnology, Santa Cruz, Calif.) was applied to lanes 1 and 2; rabbit polyclonal anti-PML antiserum was applied to lanes 3 and 4; mouse anti-HA monoclonal antibody, 16B12 (BAbCo) was applied to lanes 5 and 6. An arrowhead indicates unmodified PML.

Figure 11B:
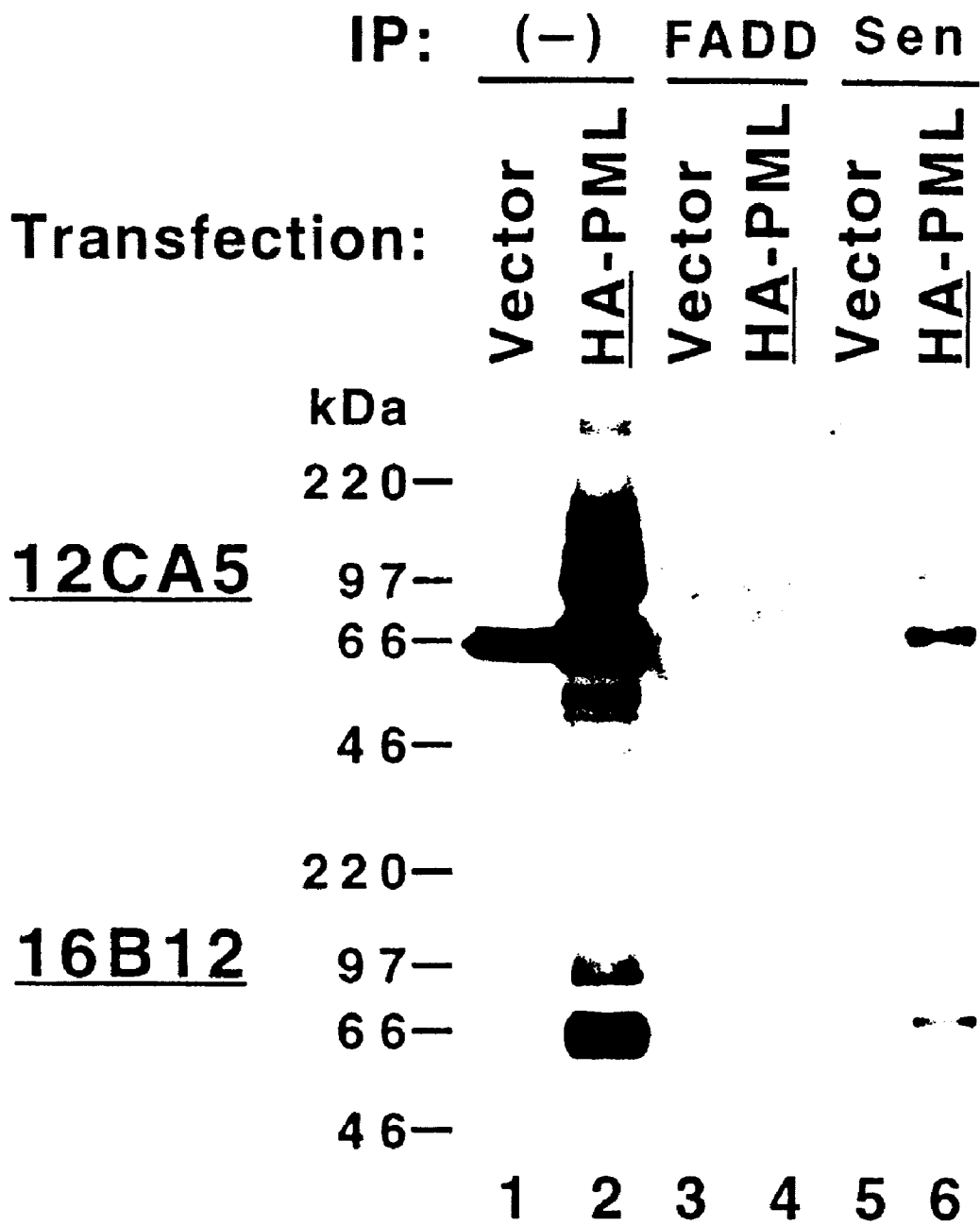

FIG. 11B. Modification of PML by sentrin-1. COS cells were transfected with vector (lanes 1, 3, 5) or with plasmids containing cDNA inserts encoding HA-PML (lanes 2, 4, 6). The lysates were analyzed by Western blotting directly (lanes 1–2) or after immunoprecipitation with anti-FADD antiserum (lanes 3–4) or with anti-sentrin-1 antiserum (lanes 5–6). Two different anti-HA antibodies (12CA5 and 16B12) were used in Western blot analysis.

Figure 11C:
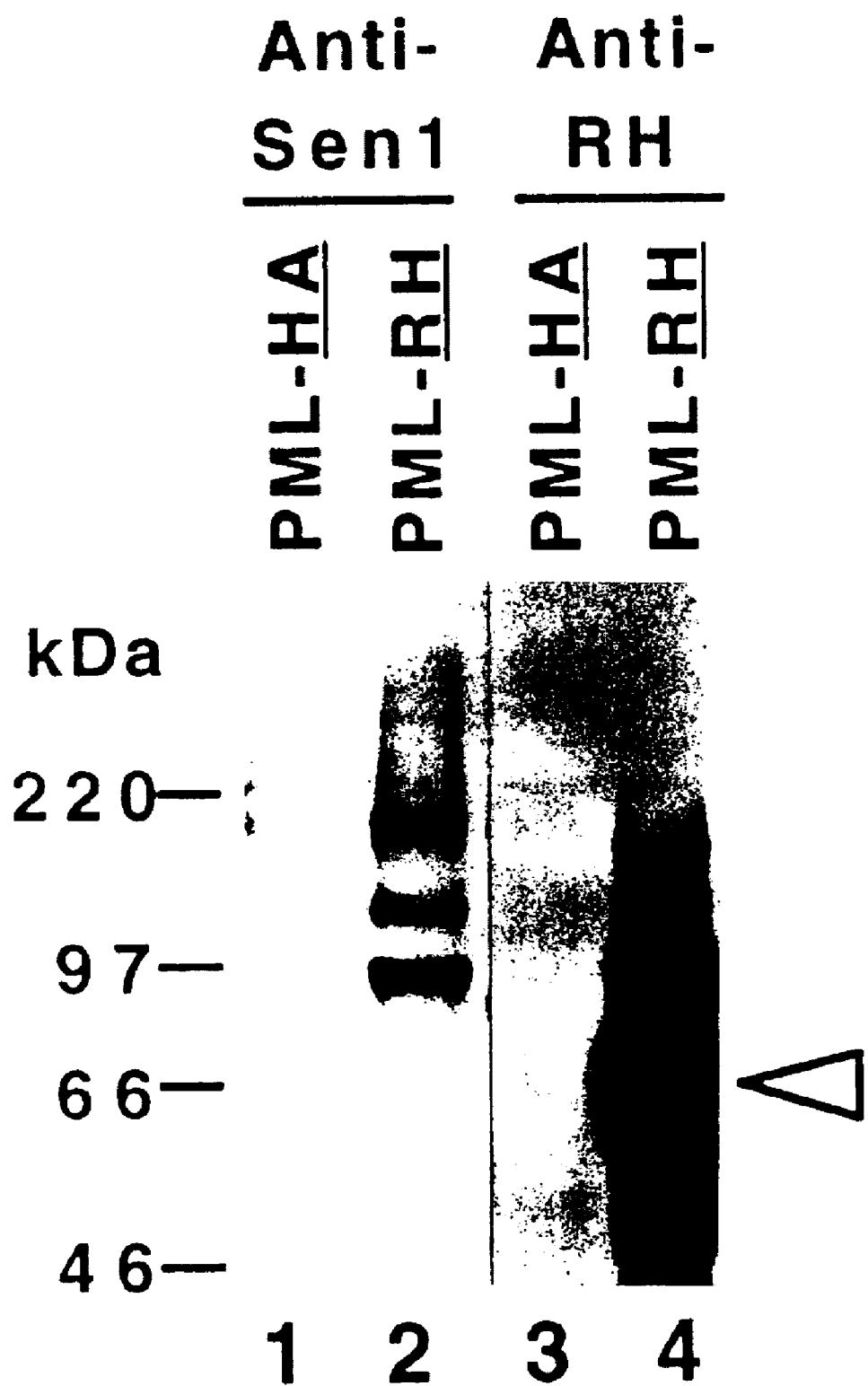

FIG. 11C. Modification of PML by sentrin-1. PML tagged with HA-epitope (lanes 1, 3) or RH-epitope (lanes 2, 4) was expressed in COS cells. The tagged protein was precipitated with Ni-charged beads and analyzed by Western blotting using rabbit anti-sentrin-1 antiserum (Kamitani et al., 1997a) (lanes 1–2) or mouse anti-RH monoclonal antibody (lanes 34). Unconjugated PML is indicated by an open arrowhead. Molecular size markers are shown on the left in kilodaltons.

FIG. 12. Amino acid alignment of NEDD8, ubiquitin, and the sentrin family members. Identical amino acids are printed in bold type (SEQ ID NOS:2, 4, 6, 14 and 15). Lys48 of ubiquitin, critical for the formation of ubiquitin multimers, is indicated by an open triangle. The Gly residue critical for conjugation is marked by a closed triangle. Accession numbers for human NEDD8, sentrin-1 (DNA: SEQ ID NO:1; protein: SEQ ID NO:2), sentrin-2 (DNA: SEQ ID NO:3; protein, SEQ ID NO:4), and sentrin-3 (DNA: SEQ ID NO:5; protein, SEQ ID NO:6) are D23662/AA484409/N24312, U83117, X99585/T08096 and X99584, respectively.

Figure 13A:
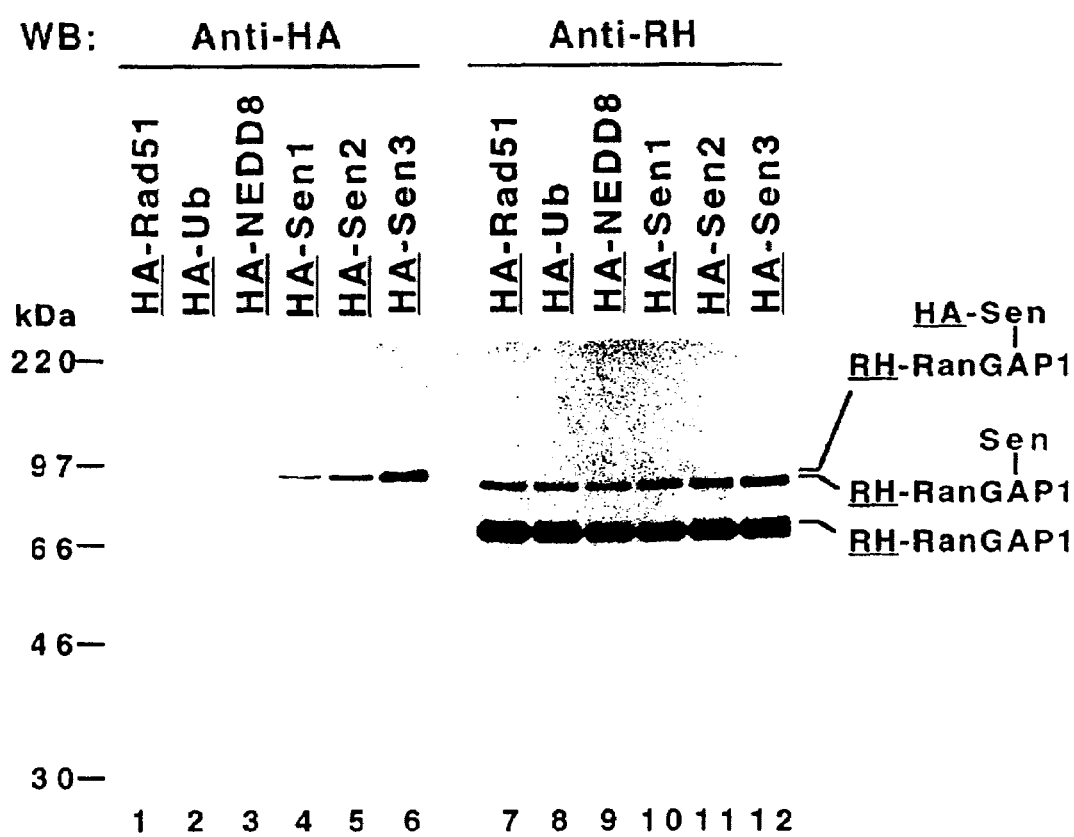

FIG. 13A. Modification of PML by sentrin-1, sentrin-2, and sentrin-3; but not by NEDD8, or ubiquitin. RH-RanGAP1 was co-expressed in COS cells with HA-Rad51 (lanes 1, 7), HA-ubiquitin (lanes 2, 8), HA-NEDD8 (lanes 3, 9), HA-sentrin-1 (lanes 4, 10), HA-sentrin-2 (lanes 5, 11), or HA-sentrin-3 (lanes 6, 12). The RH-RanGAP1 and its derivatives were precipitated with Ni-charged beads and analyzed by immunoblotting with anti-HA monoclonal antibody (lanes 1–6) or with anti-RH monoclonal antibody (lanes 7–12). (For the N-terminal and C-terminal tagging of RH-epitope (RGSHHHHHH), (SEQ ID NO:7) pcDNA3/RH-N and pcDNA3/RH-C-were generated respectively by the insertion of RH adaptor duplex into pcDNA3 (Invitrogen, San Diego, Calif.). RH-tagged RanGAP1 or PML were expressed in COS cells by transfection with pcDNA3/RH-RanGAP1 or pcDNA3/PML-RH. To construct pcDNA3/RH-RanGAP1, the full-length cDNA of RanGAP1 was amplified from human testis cDNA library (Clontech, Palo Alto, Calif.) by PCR™ using primers 5'-CTTA GGATCC-ATGGCCTCGGAAGACATTGC-3' (SEQ ID NO:8) and 5'-GTGT GAATTCTAGACCTTGTACAGCGTCTG-3' (SEQ ID NO:9). The PCR™ product was inserted into pcDNA3/RH-N to generate pcDNA3/R1-RanGAP1. In order to investigate the conjugation of sentrin family members to RanGAP1 or PML, RH-RanGAP1 or PML-RH was co-expressed with HA-tagged sentrin family members. The RH-tagged protein was purified by Ni-precipitation method, followed by Western blotting with anti-HA (16B12, BAbCo) to detect sentrinized RH-tagged protein and also with anti-RH to detect derivatives of RH-tagged proteins. The mouse anti-RH monoclonal antibody (specific for the amino acid sequence, RGSHHHH (SEQ ID NO:10) was purchased from QIAGEN (Chatsworth, Calif.). Unmodified RanGAP1, RanGAP1 modified by native COS cell sentrin, and RanGAP1 modified by HA-sentrins are indicated on the right.

Figure 13B:
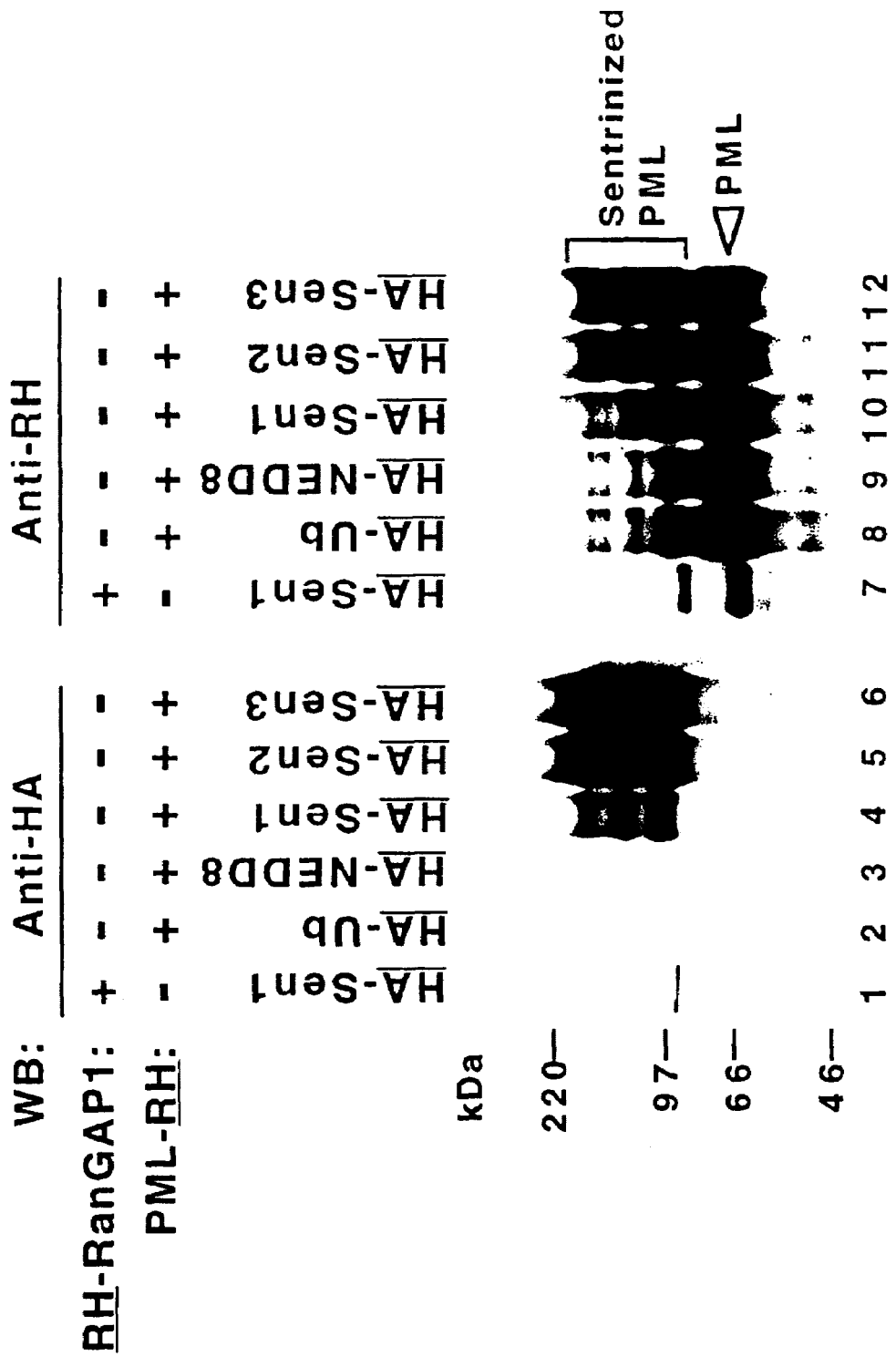

FIG. 13B. Modification of PML by sentrin-1, sentrin-2, and sentrin-3, but not by NEDD8, or ubiquitin. PML-RH was co-expressed in COS cells with HA-ubiquitin (lanes 2, 8), HA-NEDD8 (lanes 3, 9), HA-sentrin-1 (lanes 4, 10), HA-sentrin-2 (lanes 5, 11), or HA-sentrin-3 (lanes 6, 12).

COS cells expressing RH-RanGAP1 and HA-sentrin-1 were used as controls (lanes 1, 7). PML-RH and its derivatives were precipitated with Ni-charged beads and analyzed by immunoblotting with anti-HA monoclonal antibody (lanes 1–6) or with anti-RH monoclonal antibody (lanes 7–12). Unmodified PML is indicated by an arrowhead. Sentrinized PML bands are marked by a bracket.

Figure 13C:
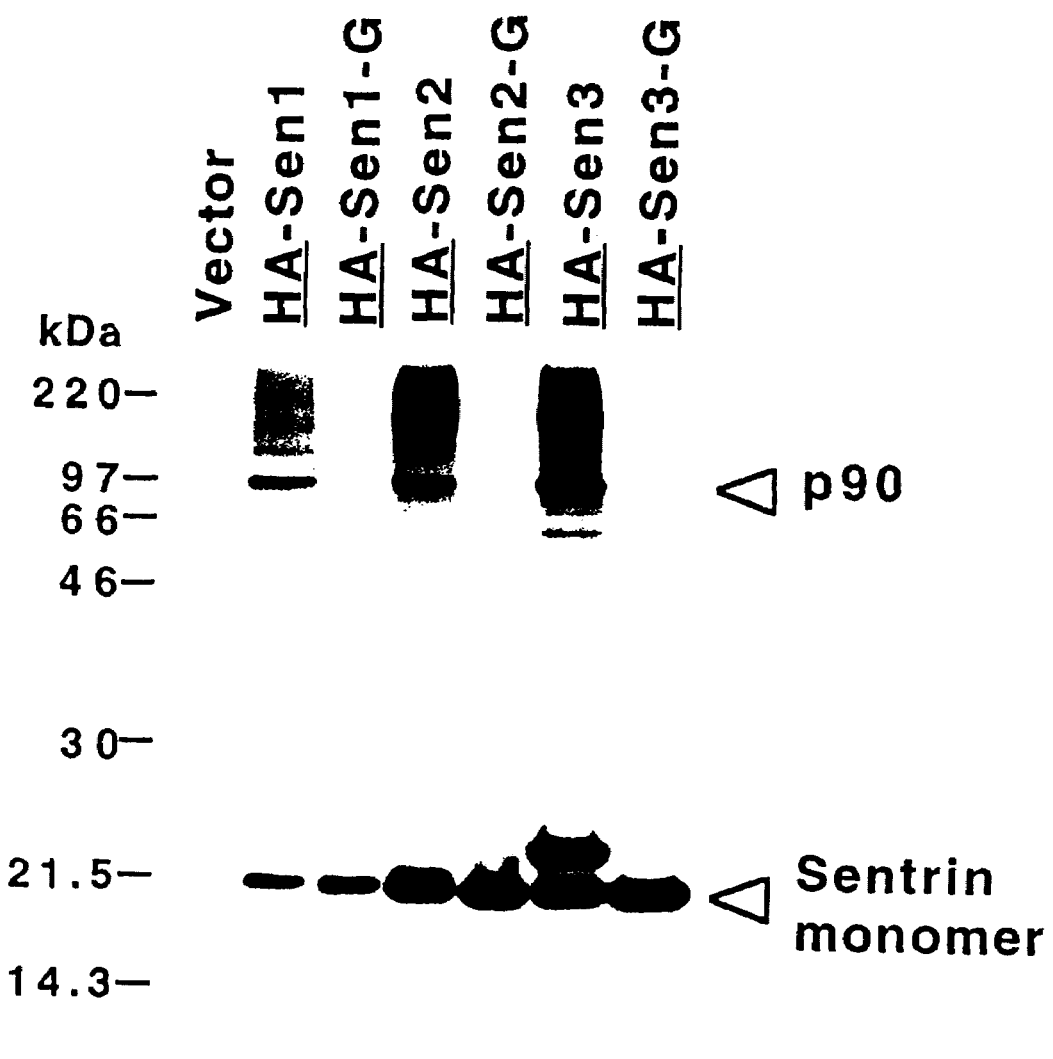

FIG. 13C. Modification of PML by sentrin-1, sentrin-2, and sentrin-3, but not by NEDD8, or ubiquitin. COS cells were transfected with empty plasmid (lane 1), or with plasmids containing cDNA insert encoding HA-tagged sentrin-1, sentrin-2, or sentrin-3 (lanes 2, 4, 6, respectively) or with plasmids containing cDNA insert encoding HA-tagged sentrin-1-G (a.a. 1–96), sentrin-2-G (a.a. 1–92), .sentrin-3-G (a.a. 1–91) (lanes 3, 5, 7, respectively) (also see. FIG. 12). The lysates were analyzed by immunoblotting with anti-HA antibody. Unconjugated sentrins and p90 (sentrinized RanGAP1) were indicated by an open triangle.

Figure 13D:

FIG. 13D. Modification of PML by sentrin-1, sentrin-2, and sentrin-3, but not by NEDD8, or ubiquitin. PML-RH was co-expressed in COS cells with HA-sentrin-1 (lanes 1, 5), HA-sentrin-2 (lanes 2, 6), HA-sentrin-1-G (lanes 3, 7), or HA-sentrin-2-G (lanes 4, 8). PML-RH and its derivatives were precipitated with Ni-charged beads and analyzed by immunoblotting with anti-HA monoclonal antibody (lanes 1–4) or with anti-RH monoclonal antibody (lanes 5–8). Unmodified PML is indicated by an arrowhead. Sentrinized PML bands are marked by a bracket. Molecular size markers are shown on the left in kilodaltons for FIG. 13A, FIG. 13B, FIG. 13C, and FIG. 13D.

4.0 DESCRIPTION OF ILLUSTRATIVE EMBODIMENTS

Disclosed herein is the identification of a novel protein, sentrin, which binds to the death domains of Fas/APO-1 and TNFR1, but not FADD/MORT1. It has been found that when overexpressed, sentrin protects cells from both anti-Fas/APO-1 and TNF-induced cell death.

The mechanism of cell death signaling caused by Fas/APO-1 or TNFR1 is complex (Kischkel et al., 1995; Hsu et al., 1996a; Chinnaiyan et al., 1996). It is clear, however, that the death domains of Fas/APO-1 and TNFR1 provide important platforms for protein—protein interaction to occur. The death domain could initiate the recruitment of downstream signaling proteins, such as FADD/MORT1, TRADD, and FLICE/MACH (Kischkel et al., 1995; Muzio et al., 1996; Boldin et al., 1996; Hsu et al., 1996a; Chinnaiyan et al., 1996). The death domain could also recruit kinases or phosphatases which will further modify death-domain associated signaling proteins (Stanger et al., 1995; Darnay et al., 1994; 1995). Thus, cell death domain associated proteins could have either pro-apoptotic or anti-apoptotic property depending on the instrinsic property of the protein. It appears, however, that since the death comain does not contain any apparent kinase or phosphatase motif, its signaling function must be dependent on other associated proteins.

4.1 Probes and Primers

DNA sequence information provided by the invention allows for the preparation of relatively short DNA (or RNA) sequences having the ability to specifically hybridize to gene sequences of the selected polynucleotides disclosed herein. Nucleic acid probes of an appropriate length may be prepared based on a consideration of a sentrin protein gene sequence, e.g., a sequence such as that shown in SEQ ID NO: 1. The ability of such DNAs and nucleic acid probes to specifically hybridize to a sentrin protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a sentrin protein gene from *Medicago* using PCR™ technology. Segments of related sentrin protein genes from other species may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of a sentrin protein-encoding sequence, such as that shown in SEQ ID NO:1. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, herein incorporated by reference, or by excising selected DNA fragments from recombinant plasmids containing appropriate inserts and suitable restriction sites.

4.2 Recombinant Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the sentrin proteins of the present invention is preferable in a eukaryotic host cell. Preferred host cells include mammalian, particularly human, host cells. Promoters that function in such cells are well-known in the art.

4.3 Promoters

As discussed, the expression of DNA encoding sentrin in a selected cell can be placed under the control of the naturally occurring homologous promoter, or a variety of heterologous promoters. A number of promoters active in various cells have been described in the literature. These include, for example, CMV or other tissue specific promoters. Promoters useful in DNA constructs applicable to the methods of the present invention may be selected based upon their ability to confer specific expression of a coding sequence for example to the presence of TNFR or Fas/APO-1. Promoters may also be selected based upon their ability to confer specific expression in tissues where sentrin protein is most effective, such as in neural cells.

In any event, the particular promoter selected to drive the expression of sentrin should be capable of promoting expression of sufficient sentrin protein to inhibit or decrease cell death, particularly as induced by TNF or Fas/Apo-1.

4.4. Expression Vectors

Means for preparing expression vectors are well known in the art. Expression (transformation vectors) used for transformation and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer anti-apoptoic activity in a cell is preferably a sentrin protein-encoding gene. In preferred embodiments, such a polypeptide has the amino acid residue sequence of SEQ ID NO:2, or a functional equivalent of this sequences.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Sentrin DNA coding sequences may comprise the entire nucleotide sequence shown in SEQ ID NO:1 or any portion thereof that may have functional equivalence, such as truncated versions. Alternatively, it may be desirable to express epitopic regions of the polypeptides in order to use these peptides to raise antibodies against the polypeptides.

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

Translational enhancers may also be incorporated as part of the vector DNA. Thus the DNA constructs of the present invention should also preferably contain one or more 5' non-translated leader sequences which may serve to enhance expression of the gene products. from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence (Griffiths, et al, 1993).

Such "enhancer" sequences may be desirable to increase or alter the translational efficiency of the resultant mRNA.

The present invention is not limited to constructs where the enhancer is derived from the native 5' non-translated promoter sequence, but may also include non-translated leader sequences derived from other non-related promoters such as other enhancer transcriptional activators or genes.

4.5 DNA Constructs for Expression of Sentrin

As noted above, the present invention provides DNA constructs or expression vectors that facilitate the expression of the DNA sequences discussed herein in eukaryotes and particularly mammalian cells. As used herein, the terms "vector construct" or "expression vector" refer to assemblies of DNA fragments operatively linked in a functional manner that direct the expression of the DNA sequences discussed herein, as well as any additional sequence(s) or gene(s) of interest.

The expression of a structural coding sequence (gene, cDNA, synthetic DNA, or other DNA) which exists in double-stranded DNA form involves transcription of messenger RNA (mRNA) from one strand of the DNA by RNA polymerase enzyme and subsequent processing of the mRNA primary transcript inside the nucleus. This processing involves a 3' non-translated region which adds polyadenylate nucleotides to the 3' end of the mRNA.

Transcription of DNA into mRNA is regulated by a region of DNA referred to as the "promoter." The promoter region contains a sequence of bases that signals RNA polymerase to associate with the DNA and initiate transcription of mRNA using one of the DNA strands as a template to make a corresponding strand of RNA.

Vectors useful in the present invention therefore include promoter elements operably linked to coding sequences of interest, and can also include 5' non-translated leader sequences, 3' non-translated regions, and one or more selectable markers. A variety of such markers are well known in the art.

4.6 Biologically-Functionally Equivalent Nucleotide Sequences

The present invention includes not only the cDNA sequence shown in SEQ ID NO:1, but also biologically functional equivalent nucleotide sequences. The phrase "biologically functional equivalent nucleotide sequences" denotes DNAs and RNAs, including genomic DNA, plasmid DNA, cDNA, synthetic DNA, and mRNA nucleotide sequences, that encode peptides, polypeptides, and proteins exhibiting the same or similar activity as that of sentrin, i.e., when introduced into host cells in a functionally operable manner so that when expressed, they produce peptides, polypeptides, or proteins exhibiting activity at a level sufficient to inhibit cell death.

4.7 DNAs Encoding Conservative Amino Acid Changes in Sentrin

Biologically functional equivalent nucleotide sequences of the present invention include nucleotide sequences encoding conservative amino-acid changes within the fundamental sentrin amino acid sequence, producing silent changes therein. Such nucleotide sequences contain corresponding base substitutions compared to nucleotide sequences encoding wild-type-sentrin.

4.8 DNA Sequences with Base Substitutions, Additions, or Deletions

In addition to nucleotide sequences encoding conservative amino acid changes within the fundamental sentrin polypeptide sequence, biologically functional equivalent nucleotide sequences of the present invention include nucleotide sequences containing other base substitutions, additions, or deletions. These include nucleic acids containing the same inherent genetic information as that contained in the nucleic acid segment of SEQ ID NO:1, and which encode peptides, polypeptides, or proteins having the same as or similar to that of sentrin in cells. Such nucleotide sequences can be referred to as "genetically equivalent modified forms" of the cDNA shown in SEQ ID NO:3, and can be identified by the methods described herein.

Mutations made in the cDNA, plasmid DNA, genomic DNA, synthetic DNA, or other nucleic acid encoding sentrin preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, it is not necessary that the nature of the mutations per se be predetermined. For example, in order to select for optimum characteristics of mutants at a given site, random mutagenesis can be conducted at the target codon.

Alternatively, mutations can be introduced at particular loci by synthesizing oligonucleotides containing a mutant sequence, flanked by restriction sites enabling ligation to fragments of the native sentrin cDNA sequence. Following ligation, the resulting reconstructed nucleotide sequence encodes a derivative form of sentrin having the desired amino acid insertion, substitution, or deletion. In either case, the expressed mutants can be screened for desired activity.

Specific examples of useful genetically equivalent modified forms of the cDNA of SEQ ID NO:1 include DNAs having a nucleotide sequence which exhibits a high level of homology, i.e., sequence identity, to the cDNA of SEQ ID NO:1. This can range from about 70% or greater sequence identity, more preferably from about 80% or greater sequence identity, and most preferably from about 90% or greater sequence identity, to the cDNA or corresponding moiety thereof of SEQ ID NO:1.

Such genetically equivalent modified forms can be readily isolated using conventional DNA—DNA or DNA-RNA hybridization techniques (Sambrook et al., 1989) or by amplification using Polymerase Chain Reaction (PCR™) methods. These forms should possess the ability to confer resistance to fungal pathogens when introduced by conventional transformation techniques into cells normally sensitive to such pathogens.

4.9 Nucleotide Sequences Encoding Fragments and Variants of Sentrin

The fragments and variants of sentrin discussed may be encoded by cDNA, plasmid DNA, genomic DNA, synthetic DNA, or mRNA. These nucleic acids should possess about 70% or greater sequence similarity, preferably about 80% or greater sequence similarity, and most preferably about 90% or greater sequence similarity, to corresponding regions or moieties of the cDNA having the nucleotide sequence shown in SEQ ID NO:1 encoding sentrin, or the mRNA corresponding thereto.

In the present invention, nucleic acids biologically functional equivalent to the cDNAs of sentrin having the nucleotide sequence shown in SEQ ID NO:1 include:

(a) DNAs having a length which has been altered either by natural or artificial mutations such as partial nucleotide deletion, insertion, addition, or the like, so that when the entire length of SEQ ID NO:1 is taken as 100%, the biologically functional equivalent sequence has an approximate length of 60–120% of that of SEQ ID NO:1, preferably 80–110% thereof, or (b) nucleotide sequences containing partial (usually 20% or less, preferably 10% or less, more preferably 5% or less of the entire length) natural or artificial mutations so that such sequences code for different amino acids, but wherein the resulting polypeptide retains the activity of sentrin. The mutated DNAs created in this manner usually encode a polypeptide having 70% or greater, preferably 80% or greater, and more preferably 90% or greater, sequence identity to the amino acid sequence of sentrin encoded by the nucleotide sequence of SEQ ID NO:1.

In the present invention, the methods employed to create artificial mutations are not specifically limited, and such mutations can be produced by any of the means conventional in the art. For example, the cDNA or gene of sentrin may be treated with appropriate restriction enzymes so as to insert or delete appropriate DNA fragments so that the proper amino acid reading frame is preserved. Subsequent to restriction endonuclease treatment, the digested DNA can be treated to fill in any overhangs, and the DNA religated.

Mutations can also be introduced at particular loci by synthesizing oligonucleotides containing a mutant sequence flanked by restriction sites enabling ligation to fragments of the native sentrin cDNA or genomic sequence. Following ligation, the resulting reconstructed sequence encodes a derivative having the desired amino acid insertion, substitution, or deletion.

Alternatively, oligonucleotide-directed site-specific or segment-specific mutagenesis procedures can be employed to produce an altered cDNA or genomic DNA sequence having particular codons altered according to the substitution, deletion, or insertion desired.

Exemplary methods of making the alterations described above are disclosed by Ausubel et al. (1995); Bauer et al. (1985); Craik (1985); Sambrook et al. (1989); and Osuna et al. (1994). Biologically functional equivalents to the cDNA sequence disclosed herein produced by any of these methods can be selected for by assaying the peptide, polypeptide, or protein encoded thereby using the techniques described herein.

4.10 DNAs Encoding Polypeptides that React with Sentrin mAbs

Biologically functional equivalent forms of the cDNA encoding sentrin include nucleotide sequences that encode peptides, polypeptides, and proteins that react with, i.e., specifically bind to, antibodies raised against sentrin, and that exhibit the same or similar activity as this polypeptide. Such antibodies can be polyclonal or monoclonal antibodies.

4.11 Genetically Degenerate Nucleotide Sequences

Due to the degeneracy of the genetic code, i.e., the existence of more than one codon for most of the amino acids naturally occurring in proteins, other DNA (and RNA) sequences that contain essentially the same genetic information as the cDNA of the present invention, and which encode substantially the same amino acid sequence as that encoded by the nucleotide sequence of SEQ ID NO:1, can be used in practicing the present invention. This principle applies as well to any of the other nucleotide sequences discussed herein.

4.12 DNAs Designed for Enhanced Expression in Particular Host Cells

Biologically functional equivalent forms of the cDNA of the present invention also include synthetic DNAs designed for enhanced expression in particular host cells. Host cells often display a preferred pattern of codon usage (Murray et al., 1989). Synthetic DNAs designed to enhance expression in a particular host should therefore reflect the pattern of codon usage in the host cell.

In the present invention, sequence similarity or identity can be determined using the "BestFit" or "Gap" programs of the Sequence Analysis Software Package, Genetics Computer Group, Inc., University of Wisconsin Biotechnology Center, Madison, Wis. 53711.

4.13 Nucleotide Sequences Encoding Fused Forms of Sentrin

Other biologically functional equivalent forms of the cDNA of SEQ ID NO:1 useful in the present invention include those which have been modified to encode conjugates with other peptides, polypeptides, or proteins, thereby encoding fusion products therewith.

4.14 Detection of Sentrin-Like Nucleic Acids by Hybridization

Although one embodiment of a nucleotide sequence encoding sentrin is shown in SEQ ID NO:1, it should be understood that the present invention also includes nucleotide sequences that hybridize to the sequence of SEQ ID NO:1 and its complementary sequence, and that code on expression for peptides, polypeptides, or proteins having the same or similar activity as that of sentrin. Such nucleotide sequences preferably hybridize to SEQ ID NO:1 or its complementary sequence under conditions of moderate to high stringency (see Sambrook et al., 1989). Exemplary conditions include initial hybridization in 6×SSC, 5× Denhardt's solution, 100 mg/ml fish sperm DNA, 0.1% SDS, at 55° C. for sufficient time to permit hybridization (e.g., several h to overnight), followed by washing two times for 15 min each in 2×SSC, 0.1% SDS, at room temperature, and two times for 15 min each in 0.5–1×SSC, 0.1% SDS, at 55° C., followed by autoradiography. Typically, the nucleic acid molecule is capable of hybridizing when the hybridization mixture is washed at least one time in 0.1×SSC at 55° C., preferably at 60° C., and more preferably at 65° C.

The present invention also encompasses nucleotide sequences that hybridize to the cDNA of SEQ ID NO:1 under salt and temperature conditions equivalent to those described above, and that code on expression for a peptide, polypeptide, or protein that has the same or similar activity as that of sentrin disclosed herein.

The nucleotide sequences described above are considered to possess a biological function substantially equivalent to that of the cDNA of SEQ ID NO:1 encoding sentrin if they encode peptides, polypeptides, or proteins having an effect differing from that of sentrin by about +25% or less.

4.15 Polypeptides Reactive with Antibodies Raised Against Sentrin

Biologically functional equivalent forms of sentrin also include peptides, polypeptides, and proteins that react with, i.e., specifically bind to, antibodies raised against sentrin, and that exhibit the same or similar activity as this polypeptide. Such antibodies can be polyclonal or monoclonal antibodies.

4.16 Characteristics of Sentrin

The present invention provides novel polypeptides that define a whole or a portion of a sentrin protein. Sentrin shares 74% homology with Smt3 from yeast, The amino acid sequence is shown in SEQ ID NO:2. Kyte-Doolittle hydropathy plot analysis showed that sentrin is composed of three hydrophilic domains. The absence of a hydrophobic leader sequence suggests that sentrin is probably a cytosolic or nuclear protein. Blast search revealed that sentrin is 18% identical and 48% similar to human ubiquitin. Sentrin has the same degree of identity and similarity to Nedd8, which was identified using a substraction cloning approach where Nedd2 (an ICE-like protein) was isolated. In addition, sentrin has weak homology to BAG-1, which contains a short ubiquitin-like domain, binds to Bcl-2, and has an anti-death activity.

Sentrin is 50% identical and 74% similar to Smt3 from yeast *S. cerevisiae* (Genbank accession number U27233). Smt3 has the ability to suppress the conditional lethal mif2 mutation which under non-permissive temperatures shows increased mitotic chromosomal instability, sensitivity to anti-microbial drugs, and formation of aberrant spindles that break in half during anaphase. Yeast cells lacking Mif2 arrest in early mitosis of the cell cycle. The high degree of homology between sentrin and Smt3 suggests that these two proteins may have conserved function.

4.17 DNA Delivery Into Host Cells

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

4.17.1 Electroporation

The application of brief, high-voltage electric pulses to a variety of animal cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.17.2 Microprojectile Bombardment

A further advantageous method for delivering transforming DNA segments to cells is microprojectile bombardment. In this method, particles may be coated with nucleic acids and delivered into cells by a propelling force. Exemplary particles include those comprised of tungsten, gold, platinum, and the like For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 h post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation and Characterization of Sentrin-1

5.1.1 Materials and Methods

Yeast strains and shuttle vectors pGBT9 (GAL4 DNA-binding domain) and pGAD424 (GAL4 activation domain) were purchased from Clontech, Calif.

Deletion mutants or full-length clones were produced by polymerase chain reaction with appropriate primer sets, restriction digested, and ligated to the appropriate vectors. Point mutant was made by oligonucleotide-directed mutagenesis. All constructs were confirmed by DNA sequencing.

BJAB (obtained from Dr. Fred Wang, Harvard Medical School) and L929 (purchased from American Type Culture Collection, Rockville, Md.) cell lines were cultured in RPMI medium and harvested at log phase. The plasmids for transfection included pSV-β-galactosidase (Promega, Madison, Wis.), pcDNA3-Sentrin, pcDNA3-crmA, and pcDNA3 empty vector (Invitrogen, San Diego, Calif.).

5.1.1.1 Two-Hybrid Screen and Two-Hybrid β-Galactosidase Assay pGBT9-Fas (191–319AA) was transformed into HF7c using the lithium acetate method. HF7c cells were incubated in 300 ml of YPD medium at 30° C. until $OD_{600}$=0.2. The cells were centrifuged at 1,000×g for 5 min at room temperature. The harvested cells were suspended in 1.5 ml of TE/LiAc solution (10 mM Tris-HCl, 1 mM EDTA and 0.1 M lithium acetate). 0.1 μg of pGBT9-Fas (191–319AA) was added to the cell suspension together with 100 μg of salmon sperm DNA and 0.6 ml of PEG/LiAc solution (10 mM Tris-HCl, 1 mM EDTA, 0.1 M lithium acetate, and 40% PEG4000).

After incubation at 30° C. for 30 min, 700 μl of DMSO was added in the solution. After heat shock at 42° C. for 15 min, the cells were harvested and resuspended in 0.5 ml of TE buffer. The transformed cells were plated on Trp synthetic medium and incubated for 4 days at 30° C. The transformed HF7c with pGBT9-Fas IC was cultured in Trp synthetic medium and sequentially transformed with 500 μg of the placenta cDNA (Matchmaker, Clontech, CA) which fused to GAL4 DNA-activating domain vector, pGAD10. The co-transformed cells were incubated for 5 days at 30° C. on Leu⁻, Trp⁻ and His⁻ synthetic medium plates. The positive colonies were picked and restreaked on triple negative plates and assessed for β-galactosidase activity using filter assay as described by the manufacturer.

5.1.1.2 Interaction Assays

Interaction assays were performed according to the protocols suggested by the manufacturer. Briefly, the yeast transformants were transferred to the paper filters and permiabilized in liquid nitrogen then placed on another filter papers presoaked in Z buffer solution (60 mM $Na_2HPO_4$, 40 mM $NaH_2PO_4$, X mM KCl, 10 mM $MgSO_4$, 50 mM β-mercaptoethanol, and 0.33 mg/ml X-gal). The filters were incubated for up to 24 hr at 30° C. The strength of interaction was graded based on the time it required for the colony to turn blue. The interaction between SV40 T antigen and P53 usually turned blue within 30 min and was graded as +++. The interaction between the death domain of Fas and sentrin (or FADD/MORT-1) turned blue within 3 h and was graded as ++. The interaction which turned blue between 3–6 h was graded as +. The interaction which took more than 6 h to turn blue was graded as +/−.

5.1.2 Isolation of Sentrin-1

Kyte-Doolittle hydropathy plot analysis showed that sentrin-1 is composed of three hydrophilic domains. The absence of a hydrophobic leader sequence suggests that sentrin-1 is probably a cytosolic protein.

Blast search revealed that sentrin-1 is 18% identical and 48% similar to human ubiquitin (FIG. 2B). Sentrin-1 has the same degree of identity and similarity to Nedd8, which was identified using a subtraction cloning approach where Nedd2 (an ICE-like protein) was isolated (Kumar et al., 1992). In addition, sentrin-1 has a weak homology to BAG-1, which contains a short ubiquitin-like domain, binds to Bcl-2, and has an anti-death activity (Takayama et al., 1995).

Sentrin-1 is 50% identical and 74% similar to Smt3 from the yeast *Saccharomyces cerevisiae* (GenBank accession number U27233). Smt3 has the ability to suppress the conditional lethal mif2 mutation which, under non-permissive temperature, shows increased mitotic chromosome instability, sensitivity to anti-microtubule drugs, and formation of aberrant spindles that break in half during anaphase (Brown et al., 1993; Meluh and Koshland, 1995). Yeast cells lacking MIF2 arrest in early mitosis of the cell cycle (Brown et al., 1993). The homology between sentrin-1 and Smt3 suggests that these two proteins may have conserved function.

Sentrin-1 (SEQ ID NO:2) fused to the Gal4 activation-domain was used to interact with a panel of Fas/APO-1 mutants fused to the DNA-binding domain.

As shown in FIG. 1A, sentrin-1 interacted with both wild type and the Δ15 mutant of Fas/APO-1, but not with the Δ23 mutant. Furthermore, sentrin-1 did not interact with the human equivalent of the 1pr$^{cg}$ mutation, V238N (Itoh and Nagata, 1993). These particular mutants were tested because removal of the C-terminal 15 amino acids of Fas/APO-1 has been shown to enhance cell death signaling, whereas removal of the C-terminal 23 amino acids or substitution of asparagine for valine in the 238 position abolished cell death signaling (Itoh and Nagata, 1993). Since sentrin-1 only interacted with the signal-competent forms of Fas/APO-1, this interaction was considered to be functionally relevant.

Because of the homology between the death domains of Fas/APO-1 and TNFR1, the inventors tested whether sentrin-1 could interact with the death domain of TNFR1. As shown in FIG. 1A, the signal-competent forms of TNFR1, namely-wt and Δ14, but not the signal-incompetent form, Δ20, interacted with sentrin-1 (Tartaglia et al., 1993). Δ14 contains the entire TNFR1 death domain (326412AA), which appears to be necessary and sufficient for interaction with sentrin-1. The strength of interaction between sentrin-1 and Fas/APO-1/Apo-1 versus TNFR1 appeared to be similar in the yeast two-hybrid system and is comparable to that between Fas/APO-1 and FADD/MORT1. Sentrin-1, however, did not interact with the death domains of CD40 and FADD/MORT1. Thus, sentrin-1's interaction pattern is highly specific.

5.2 Example 2

Isolation of a Nucleic Acid Segment Encoding Sentrin-1 pcDNA3-Sentrin-1 was constructed by digesting the pGAD424-61ORF with BamHI and subcloned into eukaryotic expression vector pcDNA3 at the BamHI site. Proper orientation of sentrin-1 insert was confirmed by DNA sequencing. pcDNA-CrmA was constructed by inserting an EcoRI fragment containing crmA from a pUC19-crmA plasmid construct, obtained from Dr. David Pickup, into the expression vector pcDNA3.

$5 \times 10^6$ BJAB cells or $2 \times 10^6$ L929 were transfected by electroporation with 10 μg of plasmid pSV-β-galactosidase plus either an equimolar amount of pcDNA3-Sentrin-1, or pcDNA3-crmA, or pcDNA3 empty vector. For BJAB cells, electroporation was performed at 220V and 960 μF using BioRad's Gene-Pulser I®. After 10 min incubation at room temperature, cells were resuspended in 1 ml of RPMI media, transferred to tissue culture flasks containing 20 ml of RPMI media and incubated at 37° C. Forty eight h after transfection, the transfected cells were divided into five equal aliquots, transferred into 6-well plates and treated with media or anti-Fas/APO-1 (CH11, Panvera, Wis.) at a concentration of 0.25, 2.5, 25, and 250 ng/ml for 20 h. The cells were harvested from the wells, transferred to microfuge tubes, centrifuged, washed with PBS, and lysed in 250 ml of lysis buffer (1 mM DTT, 0.2% Triton X-100®, 0.1 M KPO$_4$ pH 7.8). 10 ml of the cell lysates were then analyzed in duplicate for β-galactosidase activity using Galacto-Light Plus (Tropix, Bedford, Mass.) and a luminescence counter (Packard, Meriden, Conn.) as described (Memon et al., 1995). Percent survival was calculated by substracting the chemiluminescence of antibody-treated cells from media-treated cells divided by the chemiluminescence of media-treated cells.

For L929 cells, electroporation was performed at 350V and 500 μF. The transfected cells were divided into four equal aliquots and transferred to a 6-well plate. After incubation in regular media for 48 h, TNF were added to achieve final concentration of 0.5, 5, and 50 ng/ml. After incubation for another 20 h, the non-adherent cells were gently washed away with PBS and the adherent cells were harvested from the wells for measurement of β-galactosidase activity as described above. Percent survival was calculated by subtracting the chemiluminescence in TNF-treated cells from media-treated cells divided by the chemiluminescence of media-treated cells.

Using the intracellular domain of Fas/APO-1 (191–319AA) as a bait in the yeast two-hybrid system (see materials and methods), two clones (68 and 61) were isolated from a human placenta cDNA library that interacted strongly and specifically with the bait. DNA sequencing showed that clone 68 encoded an in-frame fusion of the Gal4 activation domain to the death domain of FADD/MORT1 (05; 06).

Clone 61, however, encoded an in-frame fusion of the Gal4 activation domain to a novel protein which was named sentrin-1, after sentry, because it has a guardian function against cell death signaling.

Northern blot analysis showed sentrin-1 is expressed in all tissues, but the message level is higher in the heart, skeletal muscle, testis, ovary, and thymus FIG. 1B. The full length sentrin-1 cDNA contains a 5'-untranslated region of 135 nucleotides and encodes a novel protein of 101 amino acids (FIG. 2A). The ATG initiation codon is contained within a Kozak consensus sequence (Kozak, 1991), which is necessary for efficient translation

5.3 Example 3

Expression of Sentrin-1

*E. coli*, BL21 cells transformed with pMALc2-sentrin-1 were cultured in LB with 50 μg/ml of ampicillin at OD$_{260}$=0.5. After 2 h incubation from adding isopropyl-β-D-thiogalactopyrandoside to a final concentration 0.1 mM, the culture was harvested, washed in cold buffer (20 mM Tris-HCl, 200 mM NaCl and 1 mM EDTA) and suspended in 10 ml of buffer to which 1 mM DTT, 0.1 mM PMSF were added. Following overnight storage at −20° C., the cells were disrupted by sonication. The lysate was centrifuged for 30 min at 1,000 g and the supernatant was incubated at 4° C. for 1 hr with 500 μl of a 50% (vol./vol.) suspension of amylose resin. After centrifugation, the resin was washed four times with 10 ml of buffer.

Glutathione S-transferase (GST)-Fas/APO-1, Fas/APO-1 (V238N), TNFR1, or TNFR1 Δ20 fusion proteins were produced with the same procedure as with MBP fusion protein except for the use of Glutathione sepharose beads. After binding, fusion proteins were eluted from Glutathione sepharose beads in a elusion buffer of 120 mM NaCl, 100 mM Tris-HCl (pH 8.0), and 20 mM reduced Glutathione. The eluted fusion proteins were concentrated by Centricon-10 (Amicon, Beverly, Mass.). GST-Fas/APO-1, GST-Fas/APO-1 (V238N), GST-TNFR1, GST-TNFR1 AE20 (500 ng, each) were incubated with the resin MBP-Sentrin-1 (500 ng) in binding buffer (20 mM Tris-HCl (pH7.4), 100 mM KCl, 2.5 mM CaCl$_2$, 2.5 mM MgCl$_2$, 1 mM DTT and 0.05% NP-40™) for 12 hr at 4° C.

After incubation, resins were washed five times in 1 ml of binding buffer. The bound proteins were separated by SDS-PAGE, followed by Western blotting. The blots were probed with goat antiserum against GST (Pharmacia, Piscataway, N.J.) as a primary antibody and with alkaline phosphatase-conjugated rabbit anti-goat immunoglobulin as a secondary antibody (Jackson Laboratory, ME). The bound proteins were detected using a chemiluminescent detection kit (Tropix, Bedford, Mass.). Initial studies revealed that MBP alone could not precipitate the GST fusion proteins under the buffer conditions described above.

5.4 Example 4

In Vitro Activity of Sentrin-1

To assess whether the interaction between sentrin-1 and Fas/APO-1 or TNFR1 observed in the two-hybrid system was a direct one, an in vitro interaction assay was carried out.

MBP-Sentrin-1, a fusion protein containing the maltose-binding protein and sentrin-1, was prepared and used to precipitate a panel of Glutathione S-transferase (GST)-fusion proteins containing Fas/APO-1, Fas/APO-1 (V238N), —TNFR1, or TNFR1 Δ20. GST-fusion proteins were incubated with resin-bound MBP-Sentrin-1 in binding buffer for 12 hr at 4° C. After incubation, the resins were washed extensively and the bound proteins were separated by electrophoresis on SDS-polyacrylamide gels and transferred to PVDF membrane. The blots were probed with goat anti-GST antiserum followed by alkaline phosphatase-conjugated rabbit anti-goat immunoglobulin. As shown in FIG. 3, sentrin-1 interacted with GST-Fas/APO-1, but not GST-Fas/APO-1 (V238N); with GST-TNFR1, but not with GST-TNFR1 Δ20. Thus, the in vitro interaction results are consistent with those observed in the yeast two-hybrid system.

5.5 Example 5

Sentrin-1 Protects Against Apoptosis

After establishing the association of sentrin-1 and the death domains of Fas/APO-1 and TNFR1, the inventors proceeded to study the functional significance of this interaction in a cell-death protection assay. This assay employed the use of a cotransfected plasmid with β-galactosidase as a reporter gene. BJAB, a B lymphoma cell line which expresses a high level of Fas/APO-1 and readily undergoes apoptosis following overexpression of FADD/MORT1 or addition of anti-Fas/APO-1 antibody, was used in this transient cell death assay (Chinnaiyan et al., 1995; Tewari and Dixit, 1995). CrmA, a viral serpin inhibitor that has been shown to block apoptosis mediated by anti-Fas/APO-1 antibody, by FADD/MORT1 overexpression, or by TNF treatment (Tewari and Dixit, 1995; Enari et al., 1995), was used as a positive control. Empty vector was used as a negative control.

BJAB cells were transiently transfected with either the empty vector, with a sentrin-1 expression construct, or with a CrmA expression construct in the presence of an equimolar amount of the pSV-β-galactosidase reporter plasmid. Forty eight h after transfection, BJAB cells were treated with anti-Fas/APO-1 and cell survival was assessed twenty h later. Viable transfected cells were determined by a sensitive chemiluminescent assay (Memon et al., 1995). Consistent with previous reports in stably transfected systems (Tewari and Dixit, 1995; Enari et al., 1995), transient transfection with the CrmA expression vector significantly suppressed anti-Fas/APO-1-induced apoptosis (FIG. 4A). Sentrin-1 expression provided a similar degree of protection against anti-Fas/APO-1 induced cell death compared to CrmA (N=6).

The protective effect of sentrin-1 against TNF-induced cell death was also investigated. L929, a murine cell line highly sensitive to TNF, was used in this protection assay. 48 h after electroporation with different plasmids, L929 cells were treated with different concentrations of murine TNF. 18 h later, the non-adherent cells were washed off and the adherent cells were isolated for determination of β-galactosidase activity. As shown, CrmA is protective against TNF-induced cell death (FIG. 4B). Sentrin-1 is also protective compared to vector alone (n=5). The protective effect of human sentrin-1 is less efficient in L929, a murine cell line, compared to BJAB, a human B cell line. Taken together, the data show that sentrin-1 protects against both anti-Fas/APO-1 and TNF-mediated cell death.

5.6 Example 6

Preferential Modification of Nuclear Proteins by Sentrin-1

This example illustrates that sentrin-1 is a mammalian ubiquitin-like protein that can be conjugated to other proteins in a process analogous to ubiquitination. The C-terminus of sentrin-1 is efficiently processed which allows for subsequent protein conjugation. Furthermore, limited numbers of nuclear proteins are modified by sentrin-1 which is clearly distinct from ubiquitination. Remarkably, the presence of a sentrin-1 modified p90 appears to be a prerequisite for sentrin-1 modification of nuclear proteins to occur.

5.6.1 Materials and Methods 5.6.1.1 Cell Lines and Culture Conditions

Raji, Jurkat, HL60, SW837, and SK-N-SH were purchased from American Type Culture Collection (Rockville, Md.). BJAB and COS-M6 cells were obtained from Drs. Fred Wang and Dr. Steve Goldring of Harvard Medical School. Cells were seeded in RPMI 1640 medium or D-MEM supplemented with 10% FCS and antibiotics.

5.6.1.2 Antibodies

12CA5 (Boehringer Mannheim, Indianapolis, Ind.) and 16B12 (BAbCo, Richmond, Calif.) are mouse monoclonal antibody (mAb) to the peptide sequence YPYDVPDYA (SEQ ID NO:11) of influenza hemagglutinin (HA). The rabbit polyclonal anti-Sentrin-1 antiserum was generated by immunization with a peptide corresponding to amino acids 1–21 at the amino terminus of sentrin-1. The antiserum was incubated overnight with beads coated with MBP or MBP-Sentrin-1 (Okura et al., 1996). The pre-absorbed supernatant was used for Western blotting as described below.

5.6.1.3 Western Blotting

3 µl of total cell lysate (equivalent to $1\times10^4$ cells) was loaded on each lane of 10% or 12% polyacrylamide gel, electrophoresed, and transferred to a PVDF membrane, Immobilon P (Millipore, Bedford, Mass.). Western blotting was performed using ECL detection system (Amersham, Arlington Heights, Ill.) protocol. Horseradish peroxidase (HRP)-conjugated antibodies against mouse IgG or rabbit IgG (Santa Cruz Biotechnology, Santa Cruz, Calif.) were used as secondary antibodies.

5.6.1.4 Plasmid Construction and Transfection

To express HA-tagged proteins in COS-M6 cells, two vectors for amino terminal tagging (pcDNA3/HA-N) and carboxy terminal tagging (pcDNA3/HA-C) were constructed. HA adapter-duplexes were inserted into pcDNA3 (Invitrogen, San Diego, Calif.) for vector construction. cDNAs of sentrin-1 mutants were generated by PCR™ using appropriate primers followed by ligation with the vector, pcDNA3/HA-N or pcDNA3/HA-C. The insert sequences were confirmed by direct DNA sequencing. COS-M6 cells were transfected with LipofectAMINE (GIBCO-BRL, Gaithersburg, Md.) using the manufacturer's recommendation. Transfected cells were harvested for Western blotting or immunostaining 16 h after transfection.

5.6.1.5 Immunostaining

Imunocytochemical staining was performed by the avidin-biotin-HRP complex (ABC-HRP) method using the VECTASTAIN ABC kit system (Vector, Burlingame, Calif.) as previously described (Kamitani et al., 1991). Transfected COS-M6 cells grown on a cover slip were fixed in 3.7% paraformaldehyde solution for 20 min, and permeabilized in 0.1% Triton X-100® for 10 min at room temperature. After washing, fixed cells were incubated with anti-HA antibody (16B12), followed by the incubation with biotinylated anti-mouse IgG and with ABC reagent (avidin-biotin-HRP complex). The final enzymatic disclosing procedure was performed as reported previously (Kamitani et al., 1991).

5.6.1.6 Subcellular Fractionation

Transfected COS-M6 cells were subfractionated as follows. To prepare S100 and P100, $3\times10^7$ cells were washed with PBS, resuspended in 2 ml of hypotonic lysis buffer (5 mM Tris-HCl (pH 7.4), 2.5 mM KCl, 5 mM $MgCl_2$, 1 mM DTT, 1 mM PMSF, 1 µg/ml leupeptin, 10 µg/ml aprotinin, 1.5 µM pepstatin), and incubated on ice for 15 min to swell the cells. Cell suspension was homogenized by using a dounce homogenizer, followed by microscopic evaluation. The homogenate was centrifuged at 1,000×g for 3 min to remove nucleus and undisrupted cells. Supernatant was centrifuged at 100,000×g for 1 h. The pellet was solubilized with 200 µl of 2% SDS treating solution and used as the P100 fraction. The supernatant was concentrated with Centricon-10 (Amicon, Beverly, Mass.) up to 100 µl of the volume, mixed with 100 µl of 4% SDS treating solution, and used as S100 fraction. For the preparation of nuclear fraction, $3\times10^7$ cells were washed with PBS, resuspended in 2 ml of hypotonic lysis buffer, and incubated on ice for 15 min, followed by the dounce homogenization. The homogenate was overlaid on 5 ml of lysis buffer containing 0.5 M sucrose, and centrifuged at 3,000×g for 10 min. The pellet was solubilized with 200 µl of 2% SDS treating solution and used as nuclear fraction.

5.6.2 Results

5.6.2.1 Detection of Sentrin-1 Monomer and High Molecular Weight Bands

In the ubiquitin domain, sentrin-1 is 18% identical and 48% similar to ubiquitin. In contrast to ubiquitin, sentrin-1 contains extra 21 amino acids at the N-terminus and 4 more amino acids at the C-terminus. In order to study the expression of sentrin-1 in cells, polyclonal antiserum against the N-terminal 21 amino acids was generated and put to use in a Western blot analysis. The antiserum was pre-absorbed with either maltose-binding protein (MBP) or MBP-Sentrin-1 to demonstrate specificity of the immunoreactivity to sentrin-1. As shown in FIG. 5, an 18 kDa band specific for sentrin-1 was observed in SK-N-SH, a neuroblastoma cell line. This 18 kDa band most likely represents the sentrin-1 monomer. However, the 18 kDa band could not be clearly detected in other cell lines. This could be due to rapid turnover of the sentrin-1 monomer or rapid conjugation of sentrin-1 to other proteins (see below). In addition to the 18 kDa band, a prominent 90 kDa band (p90) and a series of high molecular weight bands were observed in all cell lines. This was not unexpected because sentrin-1 possessed the invariant Gly—Gly residues near the C-terminus which would allow it to be conjugated to other proteins in a process analogous to ubiquitination (Hershko and Ciechanover, 1992; Jentsch, 1992).

In order to study the biochemistry of sentrin-1 modification in more detail, a COS cell expression system using HA-tagged sentrin-1 mutants was utilized. Briefly, HA-tagged sentrin-1 mutant was transfected into COS cells by liposome-mediated transfection and total cell lysates were prepared 16 h after transfection for Western blot detection using either anti-HA antibody or anti-sentrin-1 antiserum. HA-tagged ubiquitin (HA-Ubiquitin) was used as a control. As shown in FIG. 6A, Western blot analysis of lysate prepared from COS cells expressing HA-Ubiquitin revealed a ladder of ubiquitin monomer, multimers, and ubiquitin-conjugated proteins. This pattern of ubiquitination has been seen previously in the yeast and in mammalian cells (Hershko and Ciechanover, 1992; Jentsch, 1992). In contrast, HA-Sentrin-1 expressing cell lysate revealed only the 18 kDa sentrin-1 monomer, p90, and higher molecular weight sentrin-1 conjugates. Thus, the COS cell transfection system yields results similar to that detected by polyclonal antiserum shown in FIG. 5. In addition, the COS cell transfection system allowed clear detection of the unconjugated monomer.

5.6.2.2 Sentrin-1 C-Terminus GLY—GLY Residues

The C-terminus of sentrin-1 has four amino acids (His-Ser-Thr-Val, SEQ ID NO:12) that follows the invariant Gly—Gly residues. It has been shown that activation of the Gly residue is critical for transfer of ubiquitin to the ubiquitin conjugating enzymes and eventually to proteins (Hershko and Ciechanover, 1992; Jentsch, 1992). In order for sentrin-1 to serve in a conjugation pathway analogous to ubiquitin, the C-terminal four amino acids have to be removed. To address the question of C-terminal processing, a sentrin-1 construct with the HA-tag attached to the C-terminus was made. When Sen-GGHSTV-HA was transfected into COS cells, sentrin-1 monomer could not be detected with anti-HA mAb, but still could be detected by anti-sentrin-1 antiserum suggesting that C-terminal HA-tag had been cleaved (FIG. 6B, lane 4). When the C-terminal four amino acids were removed (HA-Sen-GG), the expression pattern (monomer, p90, and high molecular weight bands) was similar to that of HA-Sen-GGHSTV transfectant (FIG.

6B, lane 5). Removal of the invariant Gly97 residue (HA-Sen-G) completely abolished the expression of p90 and the high molecular weight bands. Thus, the presence of the C-terminal Gly97 is essential for conjugation of sentrin-1 to other proteins.

5.6.2.3 Subcellular Localization of Sentrin-1

The subcellular localization of sentrin-1 and sentrinized proteins was determined next. COS cells were transfected with either HA-Ubiquitin or HA-Sentrin-1 cDNA-containing plasmids as described previously, fixed, permeabilized, and stained with anti-HA mAb. As shown in FIG. 7A, HA-Ubiquitin could be detected both in the cytosol and the nucleus. In contrast, HA-Sentrin-1 is mostly restricted to the nucleus. HA-Sentrin-1 transfected COS cells were then fractionated into cytosolic (S100) and nuclear fraction (Nuc.) and immunoblotted with anti-HA mAb. As shown in FIG. 7B, the high molecular weight bands were highly enriched in the nuclear fraction. p90 was mostly associated with the nuclear fraction and the sentrin-1 monomers were seen mostly in the cytosol.

5.6.3 Discussion

The inventors have shown that sentrin-1 can be conjugated to other proteins in a manner similar to the process of ubiquitination. Moreover, only a limited number of cellular proteins (p90 and the high molecular weight bands) are modified by sentrin-1. Remarkably, these sentrinized proteins appear to localized predominately to the nucleus.

Using antiserum specific for the N-terminus of sentrin-1, the inventors have shown that sentrin-1 monomer is expressed at low levels in SK-N-SH cells, but not detectable in other cell types (FIG. 5). In order to study the processing of sentrin-1 monomer, a COS cell expression system was utilized. Plasmids containing HA-tagged sentrin-1 cDNA inserts were transfected into COS cells and the tagged proteins were detected by Western blot analysis. The HA-tag was placed either in the N- or C-terminus of wild type sentrin-1 or mutant sentrin-1. As shown in FIG. 6B, the C-terminus of sentrin-1 is efficiently processed in the transfected cells. Moreover, the inventors' results clearly demonstrate the requirement of the C-terminal Gly 97 residue for the formation of p90 and high-molecular weight bands. Taken together, the processing of the C-terminus of sentrin-1 is analogous to the processing of all natural ubiquitin fusion protein by C-terminal hydrolases (Hershko and Ciechanover, 1992).

The HA-Sen-GAHSTV mutant is informative because only the sentrin-1 monomer and p90 were detected in the lysate of transfected cells (FIG. 6B). Similar results were also seen in the HA-Sen-GA mutant except that an additional band, p100, is observed. Recently it was reported that a novel ubiquitin like protein (GMP1/SUMO-1) is covalently attached to RanGAP1, a 70-kDa Ras-like GTPase required for the bidirectional transport of proteins and ribonucleoproteins across the nuclear pore complex (Matunis et al., 1996; Mahajan et al., 1997). Remarkably, GMP1/SUMO-1 is identical to sentrin-1. The inventors also have evidence for the presence of p70 (unmodified RanGAP1) and p90 (sentrinized RanGAP1) in COS cells transiently transfected with an HA-tagged RanGAP1 plasmid.

RanGAP1 is a homologue of the murine Fug1 (DeGregori et al., 1994) and Sa. cerevisiae and Sc. pome Rna1p (Atkinson et al., 1985; Melchior et al., 1993). Unmodified RanGAP1 is localized in the cytosol, but excluded from the nucleus (Hopper et al., 1990). Modification of RanGAP1 by GMP1 (sentrin-1) is essential for its translocation to the cytoplasmic fiber of the nuclear pore complex (Matunis et al., 1996). Thus, sentrinization of RanGAP1 is a crucial step in nuclear translocation and should have important implications for nucleocytoplasmic transport (Gorlich and Mattaj, 1996). A hydrolase activity associated with the nuclear pore complex which releases sentrin-1 from sentrinized RanGAP1 at the nuclear pore complex has also been reported (Matunis et al., 1996). De-sentrinization at the nuclear pore complex might-allow RanGAP1 to return to the cytosol and sentrin-1 to enter the nucleus.

Recently, two other groups have also reported the cloning of cDNA identical to sentrin-1. Shen et al., using the human RAD51 as a bait, have cloned an ubiquitin-like protein, UBL1 (Shen et al., 1996). UBL1 also interacts with RAD52, which is part of a complex that mediates repair of DNA double-strand breaks (Shen et al., 1996). Boddy et al. used PML, a protein critically involved in the pathogenesis of acute promyelocytic leukemia, in a yeast two hybrid screen and identified a novel PML-interacting clone, PIC1 (Boddy et al., 1996). It is possible that RAD51, RAD52 or PML are not themselves sentrinized but rather bind to other sentrinized proteins through non-covalent interaction. It is of interest to note that a yeast homologue of sentrin-1, smt3, is capable of correcting a conditional lethal mif2 mutation which has increased mitotic chromosome instability (Brown et al., 1993; Meluh and Koshland, 1995). This is consistent with the finding that sentrinized RanGAP1 is associated with the mitotic spindle apparatus during mitosis (Matunis et al., 1996).

5.7 Example 7

Preferential Interaction of Sentrin-1 with a Ubiquitin-Conjugating Enzyme, UBC9

Using the COS cell expression system, the present example demonstrates that sentrin-1 can be conjugated to other proteins in a manner analogous to protein ubiquitination (Example 6). Moreover, sentrinized proteins appear to reside in the nucleus. The C-terminal four amino acids of sentrin-1 were efficiently cleaved to allow the conjugation of sentrin-1 to other proteins via the conserved Gly97 residue.

Since the sentrinization pathway shares many similarities with the ubiquitination pathway, it is of interest to identify specific E2 or E3 proteins which may be involved the sentrinization pathway. Using sentrin-1 as a bait in the yeast two-hybrid screen, the inventors identified a ubiquitin-conjugating enzyme, Ubc9, which binds to sentrin-1 with high affinity. The interaction between sentrin-1 and Ubc9 is much stronger than that between ubiquitin and Ubc9 or between sentrin-1 and three other E2s. Furthermore, the conserved C-terminal Gly—Gly residues of sentrin-1 are required for the high affinity interaction suggesting that sentrin-1 could form a thiol ester bond with Ubc9. This is further substantiated by an in vitro binding assay in which a β-mercaptoethanol-sensitive sentrin-1-Ubc9 conjugate was observed. Thus, Ubc9 appears to be a key conjugating enzyme for the sentrinization pathway.

5.7.1 Materials and Methods

5.7.1.1 Yeast Strains and Plasmids

Yeast strains, SFY526 and HF7c, and the shuttle vectors pGBT9 and pGAD424 were purchased from Clontech (Palo Alto, Calif.). The bait plasmid pGBT9-sentrin-1 was constructed by inserting the full-length sentrin-1 cDNA in-frame in the BamHI site of the pGBT9 vector. Deletion mutants were produced by a polymerase chain reaction-based strategy with appropriate primer sets. These inserts contained a BamHI linker at the 5' end and a stop codon and a PstI linker at the 3' end. The PCR™ products were digested with both BamHI and PstI and then were ligated into the yeast two-hybrid vectors that had been pre-digested with the same enzymes. The full-length or truncated human Ubc9 constructs were made by PCR™ amplification with appropriate primers from a plasmid containing the UBC9 cDNA and subcloned into pGAD424. The E2 cDNAs were amplified by PCR™ from a human placenta cDNA library. The substitution mutant of Ubc9(C93S) was generated using QuikChange Site-Directed Mutagenesis kit (Stratagene, La Jolla, Calif.). The sequences of all constructs were confirmed by automated sequencing (Applied Biosystems Inc, Foster City, Calif.).

5.7.1.2 Yeast Two-Hybrid Screening

Yeast two-hybrid library screening and analysis were performed essentially as described previously (Okura et al., 1996). Briefly, the yeast strain HF7c containing the bait plasmid pGBT9-sentrin-1 was transformed with a human placenta cDNA library (from Clontech) using the lithium acetate method as described in the Clontech's Matchmaker Library Protocol. Approximately $5 \times 10^6$ transformants were selected for growth on plates lacking histidine, leucine, and tryptophan. 1His+ colonies were subsequently analyzed for β-galactosidase activity and retested for their specificity by using a panel of plasmids encoding different polypeptides fused to the Gal4 DNA binding domain (Okura et al., 1996).

5.7.1.3 Expression and Purification of GST Fusion Proteins

The full-length cDNA of UBC9 was amplified by PCR™ from a human placenta cDNA library. The PCR™ product was subcloned into pGEX-2T (Pharmacia, Piscataway, N.Y.) using BamHI and EcoRI restriction sites to generate pGEX-UBC9. *Escherichia coli* BL21 cells carrying pGEX-UBC9 or pGEX-2T were grown to saturation in 10 ml of LB containing 50 μg/ml ampicillin, transferred to 500 ml LB broth for expansion to an absorbance (600 nm) of 0.8. After the addition of isopropyl-β-D-thiogalactopyranoside (final concentration 0.1 mM), the culture was incubated at room temperature for 3 h. The cells were sonicated in lysis buffer (20 mM Tris, pH8.0; 1 mM EDTA; 100 mM; NaCl; 1% IGEPAL CA-630; 100 μg/ml egg white lysozyme) and bacterial debris was removed by centrifugation. The sonicated lysates were incubated at 4° C. for 1 h with 500 μl of a 50% slurry of Glutathione Sepharose 4B beads. After centrifugation, GST-fusion protein bound beads were washed three times with 10 ml of TENI buffer (20 mM Tris, pH8.0, 1 mM EDTA, 100 mM NaCl, and 1% IGEPAL CA-630).

5.7.1.4 In Vitro Protein Binding Assays

For in vitro expression of sentrin-1 protein, the pBS-sentrin-1 plasmid, containing the sentrin-1 cDNA insert was linearized with XbaI. Sentrin-1 protein was labeled with $^{35}$S-Met by using an in vitro transcription and translation kit (TNT T7-coupled rabbit reticulocyte lysates, Promega) according to the supplier's instruction. 10 μl of in vitro translated sentrin-1 was incubated with 50 μl of glutathione-Sepharose beads containing approximately 1 μg of GST or GST-fusion proteins for 12 h at 4° C. in the binding buffer described previously (Okura et al., 1996). After washing five times in binding buffer, the samples were divided into two equal aliquots. One aliquot was treated with SDS-loading buffer without β-mercaptoethanol, another was treated with SDS-loading buffer containing 5% β-mercaptoethanol. Finally, the samples were loaded onto a 15% SDS-polyacrylamide gel and visualized by autoradiography.

5.7.2 Results and Discussion

It was of interest to determine whether sentrin-1 utilizes a similar set of enzymes in the processing of its C terminus, in the activation of the Gly residue, and in conjugation to other proteins. For this purpose, the yeast two hybrid system was used to identify cDNA clones which encode polypeptides which are able to interact with sentrin-1. Yeast strain HF7c, which contains two Gal-4-inducible reporter genes, HIS3 and lacZ, was initially transformed with the bait plasmid pGBT9-sentrin-1 and then the resulting transformant was used as host for transformation with the placenta cDNA library. Approximately $0.5 \times 10^7$ primary library transformants were plated onto plates lacking histidine, leucine, and tryptophan. A total of 104 colonies appeared on the histidine dropout plates, 16 of which stained positive when tested for expression of β-galactosidase. To test whether sentrin-1 was required for interaction with the products of the isolated cDNAs, all of these plasmids were retransformed into the yeast strain SYP526 together with plasmids encoding other Gal4 DNA binding domain fusion proteins. All hybrid proteins were found to interact only with Gal-4-sentrin-1. Subsequent analyses indicated that one of these colonies contained an approximately 1.8 kbp insertion. Analysis of the cDNA sequence showed a single open reading frame of 158 amino acids. Comparison of the deduced amino acid sequence with GenBank revealed that the protein encoded by the newly identified cDNA is Ubc9, a human ubiquitin conjugating enzyme that is a structural and functional homologue of ScUBC9 (Yasugi and Howley, 1996; Seufert et al., 1995).

The yeast two-hybrid system was used to further assess the structural requirement of sentrin-1 and Ubc9 interaction. Various deletion mutants of either sentrin-1 or Ubc9 were constructed and tested in the yeast two-hybrid assay. As shown in FIG. 8, wild type sentrin-1 interacted strongly with Ubc9, as evidenced by a detectable color change within 45 min. This is comparable to the interaction between SV40 large T and p53 and is stronger than the FADD/MORT1 and Fas interaction (Okura et al., 1996). Deletion of the four C-terminal amino acids had minimal effect on the interaction (3+). Deletion of the N terminal 23 amino acids, sentrin-1 (24–101), reduced the interaction from 4+ to 2+. Deletion of both the N and C termini, sentrin-1 (24–97), reduced the interaction to barely detectable. Deletion of the C-terminal 31 amino acids, sentrin-1 (1–70), completely abolished the interaction. The N-terminal 23 amino acids also could not interact with Ubc9. Thus, the ubiquitin-domain of sentrin-1 is required for the interaction.

Since the ubiquitin-domain of sentrin-1 is required for the interaction, the interaction between ubiquitin and Ubc9 was also tested. As shown in FIG. 8, ubiquitin did interact with Ubc9, but the interaction was much weaker than the interaction between sentrin-1 and Ubc9. Deletion of the C-terminal 50 amino acids or the N-terminal 30 amino acids of Ubc9 also abolished these interaction. These results suggest that the N-terminal 21 amino acids of sentrin-1 enhances the interaction of sentrin-1 with Ubc9. It should be emphasized that the yeast two hybrid results should not be taken to imply that Ubc9 prefers sentrin-1 over ubiquitin. The process of ubiquitination and sentrinization could be influenced by the presence of additional proteins in vivo. However, these results clearly demonstrate that the interaction between sentrin-1 and Ubc9 is highly specific and thereby biologically significant.

Ubc9 belongs to a family of ubiquitin-conjugating proteins (Jentsch, 1992). All known E2 enzymes have a conserved domain of approximately 16 kDa called the UBC domain. This domain is at least 35% identical to all known E2s and includes a centrally located cysteine residue for ubiquitin-enzyme thiol ester formation (Jentsch, 1992). The inventors have cloned four other E2s by using PCR™ amplification from a human placenta cDNA library. These E2s were tested for their ability to interact with sentrin-1. Only UbCH5B (Jensen et al.,-1995) had a weak interaction with sentrin-1. HHR6B (Koken et al., 1991), UbCH6 (Nuber et al., 1995) and E2-EPF (Liu et al., 1992) were unable to interact with sentrin-1. These observations further demonstrate the specificity of the interaction between sentrin-1 and Ubc9 interaction.

The C-terminus of sentrin-1 is efficiently processed and Gly97 is essential for sentrinization to occur (Kamitani et al., 1997). A number of C-terminal deletion and substitution mutants were constructed and tested in the yeast two hybrid assay. As shown in FIG. 8, deletion of Gly97, or Gly96–97, or substitution of Ala—Ala for Gly—Gly, abolished the interaction of sentrin-1 with Ubc9. These results are consistent with the inventors' previous finding that Gly97 plays a critical role in the formation of sentrinized proteins. These results also suggest that a covalent linkage of sentrin-1 to Ubc9 accounts for the strong interaction between these proteins in the yeast two hybrid interaction.

To provide further evidence for the interaction between sentrin-1 and Ubc9, a GST-Ubc9 fusion protein was engineered and expressed in *E coli*. GST or GST-Ubc9 proteins were then used to precipitate in vitro transcribed and translated sentrin-1. As shown in FIG. 9, GST-Ubc9 (lane 3), but not GST (lane 2), could specifically precipitate in vitro translated sentrin-1. In lane 3, a 60 kDa band could also be visualized. This band most likely represents sentrin-1 conjugated to GST-Ubc9 via a thiol ester linkage because it disappeared when the sample was reduced with 5% β-mercaptoethanol (lane 5). In separate studies, the inventors have shown that other GST fusion proteins could not precipitate sentrin-1. Thus, it appears that sentrin-1 was activated by an E1 in the reticulocyte lysate after translation. The activated sentrin-1 then bound to GST-Ubc9 via a thiol ester linkage. To further substantiate this observation, the active site cysteine residue 93 in Ubc9, which is necessary for thiol ester formation, was mutated to serine. In FIG. 10, in vitro translated sentrin-1 could be precipitated by GST-Ubc9 (lane 3) and GST-Ubc9(C93S) (lane 4). However, the higher molecular weight band was only observed in the sample precipitated by GST-Ubc9. These results suggest that sentrin-1 could form a thiol ester linkage with Ubc9 via the conserved cysteine residue.

ScUBC9 was first reported by Seufert and his colleagues in 1995 (Seufert et al., 1995). They showed that repression of Ubc9 synthesis prevents cell cycle progression at the G2 or early M phase, causing the accumulation of largebudded cells with a single nucleus, a short spindle and replicated DNA. In ubc9 mutants both CLB5, an S-phase cyclin, and CLB2, an M-phase cyclin, are stabilized (Seufert et al., 1995). In wild type cells the CLB5 protein is unstable throughout the cell cycle, whereas CLB2 turnover occurs only at a specific cell cycle stage. Recently, there have been a number of reports demonstrating the association of Ubc9 with several biologically important proteins. Hateboer and his colleagues showed that murine Ubc9 binds to the CR2 of adenovirus E1A protein (Hateboer et al., 1996). Gottlicher and his colleagues demonstrated that human Ubc9 interacts with c-Jun and the glucocorticoid receptor (Gottlicher et al., 1996). Jiang and his colleague showed that scUbc9 interacts with cbf3p subunit of the *Saccharomyces cerevisiae* centromere DNA-binding core complex (Jiang and Koltin, 1996). Wang and his colleagues reported that human Ubc9 associates with the negative regulatory domain of the Wilms' tumor gene product (WT1) (Wang et al., 1996). Yasugi and his colleagues also showed that human Ubc9 interacts with the human papillomavirus type 16 E1 replication protein (Yasugi and Howley, 1996). Kho et al. also reported that the rat Ubc9 interacts with the helix-loop-helix E2A proteins (Kho et al., 1997). Three additional reports warrant special attention. Wright et al reported that human Ubc9 is associated with the signal-competent form of human Fas (Wright et al., 1995). In light of the inventors' finding that Fas binds to sentrin-1 (Okura et al., 1996) and sentrin-1 binds to Ubc9, these results could indicate that either Fas is a target for sentrinization or Fas is part of a novel sentrinization complex that includes sentrin-1 and Ubc9. The association of both sentrin-1 and Ubc9 with other proteins is not limited to Fas. Kovalenko and his colleagues reported that human Ubc9 interacts with human Rad51 (Kovalenko et al., 1996). Furthermore, Saitoh et al. reported that RanBP2 associates with Ubc9 and a sentrin-1-modified form of RanGAP1 (Saitoh et al., 1997). The interaction of sentrin-1 and/or Ubc9 with other proteins is listed in Table 2 to facilitate comparison. It is not clear which protein listed in Table 1 is sentrinized or ubiquitinated utilizing Ubc9 as a specific E2.

TABLE 2

PROTEINS WHICH INTERACT WITH EITHER SENTRIN-1 OR UBC9, OR BOTH

| Protein | Shown to interact with | |
|---|---|---|
| | Sentrin-1 | Ubc9 |
| Fas | + | + |
| Rad51 | + | + |
| RanBP2 | + | + |
| Adeno virus E1A | | + |
| Papilloma virus E1 | | + |
| c-jun | | + |
| Glucocorticoid receptor | | + |
| cbf3p of centromere | | + |
| E12 of E2A protein | | + |
| Wilm tumor gene product | | + |
| PML | + | |
| Rad52 | + | |
| TNFR1 | + | |
| RanGAP1* | + | |

*Covalent modification by sentrin-1

5.8 Example 8

Covalent Modification of PML by the Sentrin Family of Ubiquitin-Like Proteins

Over-expression of sentrin-1 protects cells against anti-Fas or TNF-induced cell death. The inventors have also demonstrated that sentrin-1 could form covalent conjugates with other proteins in a process analogous to protein ubiquitination (Kamitani et al., 1997a). Furthermore, the majority of the sentrinized proteins are localized to the nucleus. Remarkably, the amino acid sequences of sentrin-1 and PIC1 are identical. Boddy et al. (1996) were unable to demonstrate an in-vitro interaction between PIC1 (sentrin-1) and PML, possibly due to technical problems in their co-precipitation assay (see below).

The inventors have determined whether sentrin-1 could associate with and covalently modify PML. For this purpose, HA-epitope tagged PML (HA-PML) was expressed in COS cells and total cell lysates were analyzed by Western blotting, as previously described (Examples 5–7). Three different antibodies were employed in this analysis. As shown in FIG. 11A, a mouse anti-PML monoclonal antibody detected the 70 kDa PML (arrowhead) and a 90 kDa band (lane 2). A rabbit anti-PML antiserum detected both the 70 kDa and 90 kDa band (lane 4). There is also a weak higher molecular weight band in the lysate and several lower molecular weight bands, which are most likely degradation products of PML (lane 4). A highly sensitive anti-HA monoclonal antibody detected several bands higher than 70 kDa (lane 6). Since the predicted molecular weight of PML is only 70 kDa, the presence of these higher molecular weight bands suggest that PML could either migrate aberrantly or could be modified by other molecules, such as sentrin-1 or ubiquitin.

Next, an immunoprecipitation study was performed with COS cell lysates expressing HA-PML, as previously described (Examples 5–7) (FIG. 11B). Two different anti-HA monoclonal antibodies were employed in this study to detect HA-PML and its derivatives. The total cell lysates of the transfected COS cells contained the 70 kDa unmodified HA-PML and a series of higher molecular weight bands (lane 2). As shown in lane 4, anti-FADD antiserum (Kamitani et al., 1997c) did not precipitate any proteins from the lysate. In contrast, immunoprecipitation with anti-sentrin-1 antiserum (Kamitani et al., 1997a) precipitated two proteins that were approximately 70 and 90 kDa (lane 6). These results suggest that HA-PML could be modified by sentrin-1. However, the molecular weight of the precipitate does not match the modification pattern seen in FIG. 11A. This is most likely due to protein degradation or de-sentrinization during immunoprecipitation.

To circumvent this problem, a different system was employed, as described in the inventors' recent report demonstrating the conjugation of sentrin-1 to RanGAP1. Here, PML was tagged with RH epitope (RGSHHHHHH) (SEQ ID NO:7) at the C-terminus and expressed in COS cells. Transfected cells were lysed with 6 M Guanidine HCl to denature proteins in the lysate and to prevent any non-specific proteolysis or de-sentrinization. RH-tagged PML (PML-RH) was then precipitated with nickel-charged beads and was immunoblotted with either anti-sentrin-1 antiserum or with anti-RH monoclonal antibody. As shown in FIG. 11C, 3 distinct bands were identified in the anti-sentrin-1 and anti-RH lanes (lanes 2, 4). As a control, HA-PML could not be precipitated by nickel-charged beads and could not be detected with either anti-sentrin-1 antiserum or anti-RH antibody (lanes 1, 3). These studies suggest that PML is covalently modified by sentrin-1 at multiple sites. The inventors do not favor the possibility of modification at the single site by sentrin-1 multimers because sentrin-1 does not contain the conserved Lys48 equivalent required for multimer formation (Hershko and Ciechanover, 1992) (see FIG. 12). This notion is further supported by the observation that RanGAP1 is modified by a single molecule of sentrin-1/GMP1/SUMO1 (Kamitani et al., 1997b; Mahajan et al., 1997; Matunis et al., 1996).

Sentrin-1 belongs to a family of ubiquitin-like proteins (see FIG. 12). Sentrin homologues have been reported from *A. thaliana* to *H. sapiens*, suggesting that sentrin-1 is an evolutionary conserved protein that may perform unique functions in cellular metabolism. Further analysis of the database revealed two additional human cDNA sequences that are highly homologous to sentrin-1 (Mannen et al., 1996; Lapenta et al., 1997). This is of interest because there is only one sentrin homologue reported for all of the non-mammalian genera and species. While original publications by the inventors referred to the protein as "sentrin", the inventors have now renamed the protein "sentrin-1" and the other two sequences as sentrin-2 (T08096/X99585) and sentrin-3 (X99584). It is not known whether sentrin-2 or sentrin-3 could form covalent conjugates with other proteins.

Since sentrin-1 could covalently modify PML, it is of interest to determine whether sentrin-2 or sentrin-3 could also be used as PML modifiers. For this purpose, HA-tag was placed at the N-termini of sentrin-1, sentrin-2, and sentrin-3 and expressed in COS cells as previously described (Kamitani et al., 1997a). RanGAP1 was used as a positive control because RanGAP1 is covalently modified by sentrin-1 or SUMO-1/GMP1 (Kamitani et al., 1997a; Mahajan et al., 1997; Matunis et al., 1996). It is not known, however, whether RanGAP1 could be modified by sentrin-2 or sentrin-3. HA-tagged sentrin family members were co-expressed with RH-RanGAP1 in COS cells. Total cell lysates were incubated with nickel-charged beads to precipitate RH-RanGAP1 and its derivatives. As shown in FIG. 13A, sentrin-1, sentrin-2, or sentrin-3 could covalently modify RanGAP1 (lane 4, 5, 6). This is specific because neither Rad51 (lane 1), ubiquitin (lane 2), nor NEDD8 (lane 3) could modify RanGAP1. The purified RH-RanGAP1 derivatives were also detected in a separate Western blot analysis utilizing anti-RH monoclonal antibody (lanes 7–12). As shown, both the unmodified RanGAP1 and sentrinized RanGAP1 were detected in all samples. It should be noted that p90 in lanes 7–9 was derived from RanGAP1 modified by native sentrin in COS cells. This is further supported by the observation of a 90 kDa doublet in the HA-sentrin-1, 2, or 3 transfected sample (lanes 10–12). The upper band of the doublet is most likely RanGAP1 modified by HA-sentrin and the lower band is most likely RanGAP1 modified by native sentrin (lanes 10–12). It should be noted that a single 90 kDa band was observed in cells expressing HA-tagged sentrin-1 (lane 4–6), suggesting that RanGAP1 is modified by one sentrin-1 molecule. These studies also provide the first evidence that RanGAP1 could be covalently modified by all sentrin family members. This modification is highly specific because neither NEDD8 nor ubiquitin could form a covalent linkage with RanGAP1.

A similar approach was applied to RH-tagged PML. As shown in FIG. 13B, sentrin-1, sentrin-2, or sentrin-3 could covalently modify PML (lanes 4–6). Furthermore, three sentrinized PML bands were observed (lanes 4–6). It appears that sentrin-2 and sentrin-3 are more efficient in modifying PML than sentrin-1. This could also be due to the relative abundance of the expression of sentrin-2 or sentrin-3 (see below). Again, Ub and NEDD8 could not form any stable conjugate with PML. The precipitated RH-PML derivatives were also detected in a separate Western blot analysis utilizing anti-RH monoclonal antibody (lanes 8–12). As shown, unmodified PML was detected in all samples (lanes 8–12). Thus, the inability of ubiquitin or NEDD8 to form stable conjugate with PML is not due to insufficient expression of PML in the transfected COS cells. The higher molecular weight conjugates in lanes 8 and 9 are due to conjugation of PML by native sentrin present in COS cells.

To further confirm that PML is covalently modified by sentrin, the inventors constructed mutants in which the conserved Gly residue required for the formation of isopeptide bond (marked by a closed triangle in FIG. 12) and its adjacent C-terminal amino acids have been deleted (Kamitani et al., 1997a). As shown in FIG. 13C, the native sentrins could all form stable conjugates when expressed in COS cells (lanes 2, 4, 6). In contrast, the deletion mutants were only expressed as monomers and could not form high molecular weight conjugates (lanes 3, 5, 7). These studies also demonstrated that sentrin-2 and sentrin-3 monomers were expressed more abundantly in the transfected COS cells and could form more conjugates. These HA-tagged sentrins were used in a co-expression study with RH-tagged PML (FIG. 13D). As shown, both sentrin-1 and sentrin-2 could form stable conjugates with PML (lanes 1 and 3), whereas the deletion mutants could not modify PML as expected (lanes 2 and 4). The expression of PML-RH and its derivatives were confirmed by immunoblotting with anti-RH antibody, shown in lanes 5–8. Again, PML-RH could be modified by native sentrin (lanes 6 and 8).

The predicated molecular weight of PML is approximately 70 kDa. Chang and his colleagues have reported that the PML protein migrates at about 90 kDa during SDS-PAGE probably due to its acidic nature contributed by the proline rich domain (Mu et al., 1994; Le and Chang, 1996). In view of these results, the 90 kDa band observed in these reports is most likely due to modification of PML by sentrin. There is abundant de-sentrinizing activity in the cell lysates that could contribute to the difficulty in demonstrating that PML is covalently modified by sentrin. PML, after RanGAP1, is a second target for the sentrinization pathway. Remarkably, all of the sentrin family members could form a covalent linkage with PML via the conserved Gly residue. These results also demonstrate the difference in target specificity between the sentrinization pathway and the ubiquitination pathway because neither ubiquitin nor NEDD8 could modify PML. The inventors' recent finding of a preferential interaction between sentrin-1 and Ubc9 further supports the distinction between the ubiquitination and sentrinization pathways. Thus, it appears that the sentrinization pathway has unique conjugating enzyme and target substrates.

5.9 Example 9

Sentrin-2 and Sentrin-3 Sequences 5.9.1 DNA Sequence of Sentrin-2 (SEQ ID NO:3)

```
CGGCACGAGGGTGCTGCTTGTGTGCTCGTTTGGTGCGGACCTGGTACCTC
TTYTTGTGAAGCGGCAGCTGAGGAGACTCCGGCGCTCGCCATGGCCGACG
AAAAGCCCAAGGAAGGAGTCAAGACTGAGAACAACGATCATATTAATTTG
AAGGTGGCGGGGCAGGATGGTTCTGTGGTGCAGTTTAAGATTAAGAGGCA
TACACCACTTAGTAAACTAATGAAAGCCTATTGTGAACGACAGGGATTGT
CAATGAGGCAGATCAGATTCCGATTTGACGGGCAACCAATCAATGAAACA
GACACACCTGCACAGTTGGAAATGGAGGATGAAGATACAATTGATGTGTT
CCAACAGCAGACGGGAGGTGTCTACTGAAAAGGGAACCTGCTTCTTTACT
CCAGAACTCTGTTCTTTAAAGACCAAGATTACATTCTCAATTAGAAAACT
GCAATTTGGTTCCACCACATCCTGACTACTACCGTATAGTTTTCTCTATT
CTTTCATTTCCCCCTTCCCCATTCCTTTATTGTACATAAAGTAACTGGTA
TATGTGCACAAGCATATTGCATTTTTTTTTTTTAACTAAACAGCCAAT
GGTATGTTTTGATTGACATCCAAGTGGAGACGGGGATGGGGAAAAATACT
GATTCTGTGGAAAATACCCCCCTTTCTCCCATTAGTGGNCATGCTCCATT
```

-continued
```
CAGCCCCTTAAACCTTTATAATCCCAGGTAAGGTAATTTNGCCCNCACCGG

TTTTACCCAAAAAAAAAAAAACTT
```

5.9.2 Amino Acid Sequence of Sentrin-2 (SEQ ID NO:4)

```
MADEKPKEGVKTENNDHINLKVAGQDGSVVQFKIKRHTPLSKLMKAY

CERQGLSMRQIRFRFDGQPINETDTPAQLEMEDEDTIDVFQQQTGGVY
```

5.9.3 Nucleic Acid Sequence of Sentrin-3 (SEQ ID NO:5)

```
TTCGGCACAGGCGGGAGANCGGCGGGGCCGAAGCGTGAACTCGCCCGCTC
CGGCTTGCTTCCCCCGCGCCGCCTCCCCGCGCCGCTCGGAAGCCATGTCC
GAGGAGAAGCCCAAGGAGGGTGTGAAGACAGAGAATGACCACATCAACCT
GAAGGTGGCCGGGCAGGACGGCTCCGTGGTGCAGTTCAAGATCAAGAGGC
ACACGTCGCTGAGCAAGCTGATGAAGGCCTACTGCGAGAGGCAGGGCTTG
TCAATGAGGCAGATCAGATTCAGGTTCGACGGGCAGCCAATCAATGAAAC
TGACACTCCAGCACAGCTGAGAATGGAGGACGAGGACACCATCGACGTGT
TCCAGCAGCAGACGGGAGGTGTGCCGGAGAGCAGCCTGGCAGGGCACAGT
TTCTAGAGGGCCCGTCCCCAGCCCGGGCCGTCCATCCTCGCATTGCTGTT
GAATGGTGAGCACGTGACCATGCCGACCACAAAGGTGTCTGCGGAAACTC
GAGGACATTCACCACGATGATTTTCCTCTCTTTGATGTACTTCAAGTGCA
ACTCAAAACTATATCTGCAGGGATGAATCTGTAACTTAAATTGGGCCAAT
CAGAATTGTTATCTTTGTTCAGGTAAAATGAGTTGCAAGATATTGTGGGT
ACTTTTGTGTGCTCATTTGTGTTTTCCCCCCCTCCTACAACATTTTTTTA
ACCCCAAAATTATAGCCTGAATGTTCGCTTTTAGTCTGGCCAGGGATCTG
ACTCCTGAGTTGGTTGCCTCTCCCCTGCTCACTCCAGTCACATAGAGAAT
TGGTGTTTCCCGCAGTGGGGATTGCAGCTGTTGGACAGGTATTGGGGGCA
AGGTTGGTAGGGAGGACAGACTGTCACTTGCTGTTACAGGCACAGGTGAT
TAAAATGCTAAATATTGCAAATTTAAGCTTTGTCAGTATATGGAAAAGTT
GAAGGGAAAATACTGGAATGCTTCTTCAAAGGTTAAAAAATAACCGAGTC
TTTTGGTAATTTGACCCCACGTGCTCTCTGGCCCTCAAGCATGTAACCTC
GGGGTCTGAGGCCCAGGACCCACCCCCCTGCCACCCCTCCCACCCCACTC
CCTGCTCAGTACCTGGCGTTGGTACACAGGCAAGGATTGGCACAACCAAA
ATTGGCCTTTTTCTCCCTCTTAATATTGAAGAAATTCCCACATTTCTCAT
TTGGTAATGGTGTTGTGGCCTCAGATTTCTTCTAGTATTTGCTTCTGATG
AATGATTATGGTCTATACATAAAAAGTAAGACTAAGTATTGCTGAATTT
GCAGTTATGTTGTCGTGTATAAGAGCTACTTCCAAGTGTGGTTACAAATG
AACCCATGGAATGATGACTTCATGTTCTTCTCGTGGGTTTGTGCCGTGCT
GCTTTCCAAATAGGTATTGAATTTATGCATTAGTCTGGTGATTTCAGTTC
TGTGAAATATTTTGGGATCTATACCAATTAAACATTTTCATAGTTCTGCC
TATTGTCCTTCCCTGAGGCTCCATTGCTGCTTGGTGGCCATTCTCTGCCT
```

-continued

```
TTTTACAGTCACCTGAACAATGACCCATCATCTCTTGCTTGCTTGAAATC

TTGCTGAAATGTTCTCATTTCCTGTTTGCTGTATGGGCTCGGGTGGGATG

TTTGTTGGCTCTGTTGTGTTTATTCACCAATTTGTACATTATTTGTTGTC

CTTTACTACTGTAAACAGTAAATATAGTTTGGT
```

5.9.4 Amino Acid Sequence of Sentrin-3 (SEQ ID NO:6)

```
MSEEKPKEGVKTENDHINLKVAGQDGSVVQFKIKRHTSLSKLMKAYCERQ

GLSMRQIRFRFDGQPINETDTPAQLRMEDEDTIDVFQQQTGGVPESSLAG

HSF
```

6.0 REFERENCES

The following references, to the extent that they provide exemplary procedural or other details supplementary to those set forth herein, are specifically incorporated herein by reference.

U.S. Pat. No. 4,196,265, issued Apr. 1, 1980.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,769,061, issued Sep. 6, 1988.
U.S. Pat. No. 4,965,188, issued Oct. 23, 1990.
U.S. Pat. No. 4,940,835, issued Jul. 10, 1990.
U.S. Pat. No. 4,971,908, issued Nov. 20, 1990.
U.S. Pat. No. 5,176,995, issued-Jan. 5, 1993.
U.S. Pat. No. 5,384,253, issued Jan. 24, 1995.
Altschul, Gish, Miller, Myers, and Lipman, "Basic local alignment search tool," *J. Mol. Biol.*, 215:403, 1990.
Atkinson, Dunst, Hopper, *Mol. Cell. Biol.*, 5:907–915, 1985.
Ausubel et al., "Use of *Arabidopsis thaliana* defense-related mutants to dissect the plant response to pathogens," *Proc. Natl. Acad. Sci. USA*, 92(10):4189–4196, 1995.
Bauer et al., "*Salmonella typhimurium* contains an anion-selective outer membrane porin induced by phosphate starvation," *J. Bacteriol.*, 161(2):813–816, 1985.
Boddy, M. N., Howe, K., Etkin, L. D., Solomon, E. and Freemont, P. S., "PIC 1, a novel ubiquitin-like protein which interacts with the PML component of a multiprotein complex that is disrupted in acute promyelocytic leukemia", *Oncogene*, 13:971–982, 1996.
Boldin, Goncharov, Goltsev, and Wallach, "Involvement of MACH, a novel MORT1/FADD-interacting protease, in Fas/APO-1-and TNF-Receptor-induced cell death," *Cell*, 85:803, 1996.
Boldin, Varfolomeev, Pancer, Mett, Camonis, and Wallach, "A novel protein that interacts with the death domain of Fas/APO1 contains a sequence motif related to the death domain," *J. Biol. Chem.*, 270:7795, 1995.
Brown, Goetsch, and Hartwell, "MIF2 is required for mitotic spindle integrity during anaphase spindle elongation in *Saccharomyces cerevisiae*," *J. Cell Biol.*, 123:387, 1993.
Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.
Cenciaelli, Wilhelm, Guo, Weissman, *J. Biol. Chem.*, 271: 8709–8713, 1995.
Chinnaiyan, O'Rourke, Tewari, and Dixit, "FADD, a novel death domain-containing protein, interacts with the death domain of Fas and initiates apoptosis," *Cell*, 81:505, 1995.
Chinnaiyan, Tepper, Seldin, O'Rourke, Kischkel, Hellbardt, Krammer, Peter, and Dixit, "FADD/MORT1 is a common mediator of CD95 (Fas/APO-1) and tumor necrosis factor receptor-induced apoptosis," *J. Biol. Chem.*, 271:4961, 1996.
Chu, Niu, and Williams, "A Fas-associated protein factor, FAF1, potentiates Fas-mediated apoptosis," *Proc. Natl. Acad. Sci. USA*, 92:11894, 1995.
Clapp, D. W., "Somatic gene therapy into hematopoietic cells. Current status and future implications," *Clin. Perinatol.*, 20(1):155–168, 1993.
Clem, and Miller, "Control of programmed cell death by the baculovirus genes p 35 and iap," *Mol. Cell. Biol.*, 14:5212, 1994.
Coux, Tanaka, and Goldberg, *Annu. Rev. Biochem.*, 65:801–847, 1996.
Craik et al., "Redesigning trypsin: alteration of substrate specificity," *Science*, 228(4697):291–297, 1985.
Curiel, D. T., Agarwal, S., Wagner, E., and Cotten, M., "Adenovirus enhancement of transferrin-polylysine-mediated gene delivery," *Proc. Natl. Acad. Sci. USA*, 88(19): 8850–8854, 1991.
Curiel, D. T., Wagner, E., and Cotten, M., Birnstiel, M. L., Agarwal, S., Li, C. M., Loechel, S., and Hu, P. C. high-efficiency gene transfer mediated by adenovirus coupled to DNA-polylysine complexes," *Hum. Gen. Ther.*, 3(2):147–154, 1992.
Darnay, Reddy, and Aggarwal, "Identification of a protein kinase associated with cytoplasmic domain of the p60 tumor necrosis factor receptor," *J. Biol. Chem.*, 269: 20299, 1994.
Darnay, Singh, Chaurvedi, and Aggarwal, "The p60 tumor necrosis factor (TNF) receptor-associated kinase (TRAK) binds residues 34–397 within the cytoplasmic domain involved in TNF signaling," *J. Biol. Chem.*, 270:14867, 1995.
de The et al., *Cell*, 66:675–684, 1991.
DeGregori, Russ, von Melchner, Rayburn, Priyaranjan, Jenkins, Copeland, Ruley, *Genes Dev.*, 8:265–276, 1994.
Dyck et al., *Cell*, 76:333–343, 1994.
Eglitis, M. A., and Anderson, W. F., "Retroviral vectors for introduction of genes into mammalian cells," *Biotechniques*, 6(7):608–614, 1988.
Eglitis, M. A., Kantoff, P. W., Kohn, D. B., Karson, E., Moen, R. C., Lothrop, C. D., Blaese, R. M., and Anderson, W. F., "Retroviral-mediated gene transfer into hemopoietic cells," *Avd. Exp. Med. Biol*, 241:19–27, 1988.
Enari, Hug, and Nagata, "Involvement of an ICE-like protease in Fas-mediated apoptosis," *Nature*, 375:78, 1995.
Finley, Sadis, Monia, Boucher, Ecker, Crook, Chau; "Inhibition of proteolysis and cell cycle progression in a multiubiquitination-deficient yeast mutant," *Mol Cell. Biol.*, 14:5501–5509, 1994.
Fromm, M., Taylor, L. P., and Walbot, V., "Expression of genes transferred into monocot and dicot plant cells by electroporation," *Proc. Natl. Acad. Sci USA* 82(17):5824–5828, 1985.
Gefter et al., *Somat. Cell Genet.*, 3:231–236, 1977.
Gorlich and Mattaj, *Science*, 271:513–1544, 1996.
Gottlicher, Heck, Doucas, Wade, Kullmann, Cato, Evans, Herrlich, *Steroids*, 61:257–262, 1996.

Graham, F. L., and van der Eb, A. J., "Transformation of rat cells by DNA of human adenovirus 5," Virology 54(2): 536–539, 1973.

Griffiths et al., "Hybrid human immunodeficiency virus Gag particles as an antigen carrier system: induction of cytotoxic T-cell and humoral responses by a Gag:V3 fusion," J. Virol., 67(6):3191–3198, 1993.

Haas, Ahrens, Bright, Ankel, J. Biol. Chem., 262:11315–11323, 1987

Hateboer, Hijmans, Nooij, Schlenker, Jentsch, Bernards, J. Biol. Chem., 271:25906–25911, 1996.

Hershko and Ciechanover, Annu. Rev. Biochem., 61:761–807, 1992.

Hiller, Finger, Schweiger, Wolf, Science, 273:1725–1728, 1996.

Hochstrasser, Cell, 84:813–815, 1996.

Hochstrasser, Curr. Op. Cell Biol., 7:215–233, 1995.

Hodgins, Ellison, Ellison, J. Biol. Chem., 268:8807–8812, 1992.

Hopkin, J. NIH Research, 9:36–42, 1997.

Hopper, Traglia, Dunst, J. Cell Biol., 111:309–321, 1990.

Hsu, Xiong, and Goeddel, "The TNF receptor 1-associated protein TRADD signals cell death and NF-kB activation," Cell, 81:495, 1995.

Hsu, Shu, Pan, and Goeddel, "TRADD-TRAF2 and TRADD-FADD interactions define two distinct TNF receptor 1 signal transduction pathways," Cell, 84:299, 1996a.

Hsu, Huang, Shu, Baichwal, and Goeddel, "TNF-dependent recruitment of the protein kinase RIP to the TNF receptor-1," Immunity, 4:387, 1996b.

Itoh and Nagata, "A novel protein domain required for apoptosis," J. Biol. Chem., 268:10932, 1993.

Itoh, Yonehara, Ishii, Yonehara, Mizushima, Sameshima, Hase, Seto, and Nagata, "The polypeptide encoded by the cDNA for human cell surface antigen Fas can mediate apoptosis," Cell, 66:233, 1991.

Jameson and Wolf, "The Antigenic Index: A Novel Algorithm for Predicting Antigenic Determinants," Compu. Appl. Biosci., 4(1):181–6, 1988.

Jensen, Bates, Yang, Vierstra, Weissman, J. Biol. Chem., 270:30408–30414, 1995.

Jentsch, Ann. Rev. Genet., 26:179–207, 1992.

Jiang and Koltin, Mol. Gen. Genet., 251:153–160, 1996.

Johnston, S. A., and Tang, D. C., "Gene gun transfection of animal cells and genetic immunization," Methods Cell. Biol., 43(A):353–365, 1994.

Kakizuka et al., Cell, 66:663–674, 1991.

Kamitani, Nguyen, Yeh, J. Biol. Chem., 272:14001–14004, 1997a.

Kamitani, Katsumi, Nguyen, Yeh, J. Biol. Chem., 272:28557–28562, 1997b.

Kamitani, Nguyen, Yeh, J. Biol. Chem., 272:22307–22314, 1997c. Kamitani, Suzuki, Yano, Clin. Immunol. and Immunopath., 58:217–235, 1991.

Kastner et al., EMBO J, 11:629–642, 1992.

Kho, Huggins, Endege, Hsieh, Lee, Haber, J. Biol. Chem., 272:3845–3851, 1997.

Kischkel, Hellbardt, Behrmann, Germer, Pawlita, Krammer, and Peter, "Cytotoxicity-dependent APO-1 (FAS/CD95)-associated proteins form a death-inducing signaling complex (DISC) with the receptor," EMBO J., 14:5579, 1995.

Kohler and Milstein, Nature, 256:495497, 1975.

Kohler and Milstein, Eur. J. Immunol., 6:511–519, 1976.

Koken, Reynolds, Jaspers-Dekker, Prakash, Prakash, Bootsma, Hoeijmakers, "Dhr6, a Drosophila homolog of the yeast DNA repair gene RAD6," Proc. Natl. Acad. Sci. USA, 88:8865–8869, 1991.

Kovalenko, Plug, Haaf, Gonda, Ashley, Ward, Radding, Golum, Proc. Natl. Acad. Sci USA, 93:2958–2963, 1996.

Kozak, "An analysis of 5'-noncoding sequences from 699 vertebrate messenger RNAs," J. Biol. Chem., 266:19867, 1991.

Kuby, J., "Immunology" 2nd Edition. W.H. Freeman & Company, New York, 1994.

Kumar, Tomooka, and Noda, "Identification of a set of genes with developmentally down-regulated expression in the mouse brain," Biochem. Biophy. Res. Com., 185:1155, 1992.

Kyte, J., and Doolittle, R. F., A simple method for displaying the hydropathic character of a protein," J. Mol. Biol., 157(1):105–132, 1982.

Lapenta, Genomics, 40:362–266, 1997.

Larson et al., Am. J. Med., 76:827–841, 1984.

Le and Chang, J. Biol. Chem., 271:130–135, 1996.

Liston, Roy, Tamai, Lefebvre, Baird, Cherton-Horvat, Farahani, McLean, Ikeda, Mackenzie, and Korneluk, "Suppression of apoptosis in mammalian cells by NAIP and a related family of IAP genes," Nature, 379:349, 1996.

Liu, Diaz, Haas, Giudice, J. Biol. Chem., 267:15829–15835, 1992.

Liu, Mu, Chang, J. Exp. Med., 181:1965–1972, 1995.

Lu, L., Xiao, M., Clapp, D. W., Li, Z. H., and Broxmeyer, H. E., "High efficiency retroviral mediated gene transducion into single isolated immature and replatable CD34 (3+) hematopoietic stem/progenitor cells from human umbilical cord blood," J. Exp. Med., 178(6):2089–2096, 1993.

Mahajan, Delphin, Guan, Gerace, Melchior, Cell, 88:97–107, 1997.

Maloy et al., "Microbial Genetics" 2nd Edition. Jones and Barlett Publishers, Boston, 1994.

Mannen, Tseng, Cho, Li, Biochem. Biophy. Res. Comm., 222:178–180, 1996.

Matunis, Coutavas, Blobel, J. Cell Biol., 135:1457–1470, 1996.

Melchior, Weber, Gerke, Mol. Biol. Cell, 4:569–581, 1993.

Meluh and Koshland, "Evidence that the MiF2 gene of Saccharomyces cerevisiae encodes a centromere protein with homology to the mammalian centromere protein CENP-C," Mol. Biol. Cell, 6:793, 1995.

Memon, Petrak, Moreno, and Zacharchuk, "A simple assay for examining the effect of transiently expressed genes on programmed cell-death," J. Immunol. Methods, 180:15, 1995.

Mu, Chin, Liu, Lozano, Chang, Mol. Cell. Biol., 14:6858–6867, 1994.

Murray, Cell, 81:149–152, 1995.

Muzio, Chinnaiyan, Kischkel, O'Rourke, Shevchenko, Ni, Scaffidi, Bretz, Zhang, Gentz, Mann, Krammer, Peter, and Dixit, "FLICE, novel FADD homologous ICE/CED-3-like protease, is recruited to the CD95 (Fas/APO-1) death-inducing signaling complex," Cell, 85:817, 1996.

Nuber, Schwartz, Kaiser, Schneider, Scheffner, "Cloning of human ubiquitin-conjugating enzymes UbCH6 and UbCH7 (E2-F1) and characterization of their interaction with E6-AP and RSP5," J. Biol. Chem., 271:2795–2800, 1995.

Okura, Gong, Kamitani, Wada, Okura, Wei, Chang, Yeh, J. Immunol., 157:4277–4281, 1996.

Oltvai and Korsmeyer, "Checkpoints of dueling dimers foil death wishes," *Cell,* 79:189, 1994.
Osuna et al., "Microbial systems and directed evolution of protein activities," *Crit. Rev. Microbiol.,* 20(2):107–116, 1994.
Prokop, A., and Bajpai, R. K. "Recombinant DNA Technology I" *Ann. N.Y. Acad. Sci.,* vol. 646, 1991.
Rock, Gramm, Rothstein, Clark, Stein, Dick, Hwang, Goldberg, *Cell,* 78:761–771, 1994.
Saltoh, Pu, R., Cavenagh, Dasso, *Proc. Natl. Acad. Sci. USA.,* 94:3736–3741, 1997.
Sambrook, J. et al., "Molecular Cloning: A Laboratory Manual," Cold Spring Harbor Laboratory, Cold Spring Harbor, N.Y., 1989.
Sato, Irie, Kitada, and Reed, "FAP-1: A protein tyrosine phosphatase that associates with Fas," *Science,* 268:411, 1995.
Segal, I. H., "Biochemical Calculations" 2nd Edition. John Wiley & Sons, New York, 1976.
Seufert, Futcher, Jentsch, *Nature,* 373:78–81, 1995.
Shen, Pardington-Purtymun, Comeaux, Moyzis, Chen, *Genomics,* 36:271–279, 1996.
Smith, Farrah, and Goodwin "The TNF receptor superfamily of cellular and viral proteins: activation, costimulation, and death," *Cell,* 76:959, 1994.
Stanger, Leder, Lee, Kim, and Seed, "RIP: a novel protein containing a death domain that interacts with Fas/APO-1 (CD95) in yeast and causes cell death," *Cell,* 81:513, 1995.
Takayama, Sato, Krajewski, Kochel, Irie, Millan, and Reed, "Cloning and functional analysis of BAG-1: a novel Bcl-2-binding protein with anti-cell death activity," *Cell,* 80:279, 1995.
Tartaglia, Ayres, Wong, and Goeddel, "A novel domain within the 55 kd TNF receptor signals cell death," *Cell,* 74:845, 1993.
Tewari, and Dixit, "Fas- and TNF-induced apoptosis is inhibited by the poxvirus crmA gene product," *J. Biol. Chem.,* 270:3255, 1995.
Vito, Lacana, and D'Adamio, "Interfering with apoptosis: $Ca^{2+}$-binding protein ALG-2 and Alzheimer's disease gene ALG-3," Science, 271:521, 1996.
Wagner, E., Zatloukal, K., Cotten, M., Kirlappos, H., Mechtler, K., Curiel, D. T., and Birnstiel, M. L., "Coupling of adenovirus to transferrin-polylysine/DNA complexes greatly enhances receptor-mediated gene delivery and expression of transfected genes," *Proc. Natl. Acad. Sci USA,* 89(13):6099–6103, 1992.
Wang, Qui, Seufert, Taguchi, Testa, Whitmore, Callen, Welsh, Shenk, Deuel, 1996 *J. Biol. Chem.,* 271:24811–24816, 1996.
Weis et al., *Cell,* 76:345–356, 1994.
Wilkinson, *Ann. Rev. Nutrition,* 15:161–189, 1995.
Wolf et al., "An Integrated Family of Amino Acid Sequence Analysis Programs," *Compu. Appl. Biosci.,* 4(1):187–91, 1988.
Wong, T. E., and Neumann, E., "Electric field mediated gene transfer," *Biochim. Biophys. Res. Commun.,* 107(2):584–587, 1982.
Wright, Futcher, Geha, *J. Biol. Chem.,* 271:31037–31043, 1995.
Yasugi and Howley, *Nucl. Acids Res.,* 24.2005–2010, 1996.
Zatloukal, L., Wagner, E., Cotten, M., Phillips, S., Plank, C., Steinlein, P., Curiel, D. T., and Birnstiel, M. L., "Transferrinfection: a highly efficient way to express gene constructs in eukaryotic cells," *Ann. N.Y. Acad. Sci.,* 660: 136–153, 1992.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of inhibiting apoptosis in a cell comprising providing, in vitro, the cell with a nucleic acid segment encoding a polypeptide comprising SEQ ID NO:2, wherein a Fas and/or TNFR1 mediated apoptosis pathway is inhibited in the cell.

2. The method of claim 1, wherein the nucleic acid segment is operatively linked to a promoter that expresses the nucleic acid in the cell to provide the polypeptide.

3. The method of claim 2, wherein the nucleic acid segment is comprised within a vector.

4. A method of inhibiting apoptosis in a cell comprising providing, in vitro, the cell with a nucleic acid segment comprising at least SEQ ID NO:1, wherein a Fas and/or TNFR1 mediated apoptosis pathway is inhibited in the cell.

5. The method of claim 4, wherein the nucleic acid segment is operatively linked to a promoter that expresses the nucleic acid in the cell to provide the polypeptide.

6. The method of claim 5, wherein the nucleic acid segment is comprised within a vector.

* * * * *